US011253620B2

United States Patent
Golkowski et al.

(10) Patent No.: US 11,253,620 B2
(45) Date of Patent: Feb. 22, 2022

(54) STERILIZATION, DISINFECTION, SANITIZATION, DECONTAMINATION, AND THERAPEUTIC DEVICES, SYSTEMS, AND METHODS

(71) Applicant: STERIFRE MEDICAL, INC., Kirkland, WA (US)

(72) Inventors: Czeslaw Golkowski, Ithaca, NY (US); Rick Shea, Seattle, WA (US); Jonathan W. Greene, Ithaca, NY (US); Mark Golkowski, Denver, CO (US); Anya Golkowski, Ithaca, NY (US); Tom Steffie, Ithaca, NY (US)

(73) Assignee: Sterifre Medical, Inc., Kirkland, WA (US)

( * ) Notice: Subject to any disclaimer, the term of this patent is extended or adjusted under 35 U.S.C. 154(b) by 0 days.

(21) Appl. No.: 16/309,064

(22) PCT Filed: Jun. 15, 2017

(86) PCT No.: PCT/US2017/037762
§ 371 (c)(1),
(2) Date: Dec. 11, 2018

(87) PCT Pub. No.: WO2017/218832
PCT Pub. Date: Dec. 21, 2017

(65) Prior Publication Data
US 2019/0314535 A1    Oct. 17, 2019

Related U.S. Application Data

(60) Provisional application No. 62/351,873, filed on Jun. 17, 2016, provisional application No. 62/351,872, (Continued)

(51) Int. Cl.
*A61L 2/00*    (2006.01)
*A61L 9/00*    (2006.01)
(Continued)

(52) U.S. Cl.
CPC ............... *A61L 2/14* (2013.01); *A61L 2/0094* (2013.01); *A61L 2/208* (2013.01); *A61L 2/24* (2013.01);
(Continued)

(58) Field of Classification Search
CPC ........ A61L 2/00; A61L 2/0082; A61L 2/0094; A61L 2/14; A61L 2/20; A61L 2/202; A61L 2/208; A61L 2202/11
(Continued)

(56) References Cited

U.S. PATENT DOCUMENTS

| 4,863,688 A | 9/1989 | Schmidt et al. |
| 4,992,247 A | 2/1991 | Foti |

(Continued)

FOREIGN PATENT DOCUMENTS

| CA | 2735739 | 1/2011 |
| CA | 2767726 | 4/2011 |

(Continued)

OTHER PUBLICATIONS

International Search Report and Written For PCT Application No. PCT/US18/57404, dated Jan. 11, 2019 in 13 pages.

(Continued)

*Primary Examiner* — Monzer R Chorbaji
(74) *Attorney, Agent, or Firm* — Knobbe Martens Olson and Bear, LLP

(57) ABSTRACT

A sterilization, disinfection, sanitization, or decontamination system having a chamber defining a region, and a generator for creating a free radical effluent with reactive oxygen, nitrogen, and other species and/or a vaporizer. A closed loop circulating system without a free-radical destroyer is provided for supplying the mixture of free radicals from the generator mixed with the hydrogen peroxide solution in the form of the effluent to the chamber. The system is used in (Continued)

sterilizing, disinfecting, sanitizing, or decontaminating items in the chamber or room and, with a wound chamber, in treating wounds on a body. The wound chamber may be designed to maintain separation from wounds being treated. Various embodiments can control moisture to reduce or avoid unwanted condensation. Some embodiments can be incorporated into an appliance having a closed space, such as a washing machine. Some embodiments may include a residual coating device that deposits a bactericidal coating on sterilized items.

25 Claims, 31 Drawing Sheets

Related U.S. Application Data filed on Jun. 17, 2016, provisional application No. 62/424,319, filed on Nov. 18, 2016.

(51) Int. Cl.
| | | |
|---|---|---|
| *A62B 7/08* | (2006.01) | |
| *A61L 2/14* | (2006.01) | |
| *A61L 2/20* | (2006.01) | |
| *A61L 2/24* | (2006.01) | |
| *A61L 2/26* | (2006.01) | |

(52) U.S. Cl.
CPC .......... *A61L 2/007* (2013.01); *A61L 2/26* (2013.01); *A61L 2202/11* (2013.01); *A61L 2202/122* (2013.01); *A61L 2202/14* (2013.01); *A61L 2202/24* (2013.01)

(58) Field of Classification Search
USPC ......... 422/28, 121, 123, 295, 298–299, 305, 422/307
See application file for complete search history.

(56) References Cited

U.S. PATENT DOCUMENTS

| | | | |
|---|---|---|---|
| 5,087,418 A | 2/1992 | Jacob | |
| 5,173,258 A | 12/1992 | Childers | |
| 5,209,411 A | 5/1993 | Dineley et al. | |
| 5,445,792 A | 8/1995 | Rickloff et al. | |
| 5,508,009 A | 4/1996 | Rickloff et al. | |
| 5,534,221 A | 7/1996 | Hillebrenner et al. | |
| 5,578,280 A | 11/1996 | Kazi et al. | |
| 5,779,973 A | 7/1998 | Edwards et al. | |
| 5,792,435 A | 8/1998 | Mueller et al. | |
| 6,073,627 A | 6/2000 | Sunnen | |
| 6,077,480 A | 6/2000 | Edwards et al. | |
| 6,113,851 A | 9/2000 | Soloshenko et al. | |
| 6,156,267 A | 12/2000 | Pai et al. | |
| 6,187,266 B1 | 2/2001 | Lin et al. | |
| 6,329,628 B1 | 12/2001 | Kuo et al. | |
| 7,091,441 B1 | 8/2006 | Kuo | |
| 7,186,374 B2 | 3/2007 | Zelina et al. | |
| 7,621,985 B1 | 11/2009 | Kuo | |
| 7,777,151 B2 | 8/2010 | Kuo | |
| 7,803,315 B2 | 9/2010 | McDonnell et al. | |
| 7,880,887 B2 | 2/2011 | Olson et al. | |
| 8,115,135 B2 | 2/2012 | Kuo | |
| D656,622 S | 3/2012 | Gasser et al. | |
| 8,153,078 B2 | 4/2012 | Bacik et al. | |
| 8,221,679 B2 | 7/2012 | Golkowski | |
| 8,444,919 B2 | 5/2013 | Erickson | |
| 8,551,399 B2 | 10/2013 | Shannon et al. | |
| 8,591,807 B2 | 11/2013 | Berentsveig et al. | |
| 8,591,808 B2 | 11/2013 | Berentsveig et al. | |
| 8,636,951 B2 | 1/2014 | Shannon et al. | |
| 8,658,089 B2 | 2/2014 | Berentsveig et al. | |
| 8,668,882 B2 | 3/2014 | Berentsveig | |
| 8,758,681 B2 | 6/2014 | Golkowski | |
| 8,927,896 B2 | 1/2015 | Kuo | |
| 8,974,737 B2 | 3/2015 | Erickson | |
| 8,977,115 B2 | 3/2015 | Penman, Jr. | |
| 8,992,829 B2 | 3/2015 | Shannon et al. | |
| 9,010,574 B2 | 4/2015 | Gasser et al. | |
| 9,027,385 B2 | 5/2015 | Hingley et al. | |
| 9,050,385 B2 | 6/2015 | Weinberger et al. | |
| 9,138,005 B2 | 9/2015 | Berentsveig et al. | |
| 9,192,164 B2 | 11/2015 | Berentsveig et al. | |
| 9,226,495 B2 | 1/2016 | Berentsveig et al. | |
| 9,241,491 B2 | 1/2016 | Berentsveig et al. | |
| 9,333,275 B2 | 5/2016 | Berentsveig | |
| 9,849,204 B2 | 12/2017 | Taggart | |
| RE47,582 E | 8/2019 | Golkowski | |
| 2002/0068028 A1 | 6/2002 | Hight, III | |
| 2005/0063882 A1 | 3/2005 | Centanni et al. | |
| 2005/0129571 A1 | 6/2005 | Centanni | |
| 2005/0260097 A1 | 11/2005 | Williams et al. | |
| 2006/0027539 A1 | 2/2006 | Golkowski | |
| 2007/0221582 A1 | 9/2007 | Holland et al. | |
| 2007/0274858 A1 | 11/2007 | Childers et al. | |
| 2008/0014113 A1 | 1/2008 | Centanni | |
| 2008/0267819 A1 | 10/2008 | Bacik et al. | |
| 2012/0277662 A1* | 11/2012 | Golkowski | ............... A61L 2/00 604/24 |
| 2014/0105783 A1 | 4/2014 | Levsen et al. | |
| 2017/0304476 A1 | 10/2017 | Taggart et al. | |

FOREIGN PATENT DOCUMENTS

| | | | |
|---|---|---|---|
| EP | 0298694 | 1/1989 | |
| EP | 0774263 | 5/1997 | |
| EP | 0906125 | 4/2004 | |
| EP | 1557181 | 7/2005 | |
| EP | 2525838 | 7/2011 | |
| GB | 2371986 | 8/2002 | |
| JP | 2002-360672 | 12/2002 | |
| JP | 2006-205085 | 8/2006 | |
| JP | 2014-023596 | 2/2014 | |
| KR | 10-0782040 | 12/2007 | |
| KR | WO 2011/149188 | * 12/2011 | ............... A61L 2/20 |
| WO | WO 1988/004939 | 7/1988 | |
| WO | WO 1991/005573 | 5/1991 | |
| WO | WO 1997/047331 | 12/1997 | |
| WO | WO 2009/005252 | 1/2009 | |
| WO | WO2011/003179 | 1/2011 | |
| WO | WO2011/085466 | 7/2011 | |
| WO | WO 2011/149188 | 12/2011 | |
| WO | WO 2014/123280 | 8/2014 | |
| WO | WO 2016/064288 | 4/2016 | |
| WO | WO 2017/218832 | 12/2017 | |
| WO | WO 2019/084203 | 5/2019 | |

OTHER PUBLICATIONS

"Ellie. The first ever digital UV sterlizing pod" available at https://www.indiegogo.com/projects/ellie-the-first-ever-digital-uv-sterlizing-pod-baby-technology--2, retrieved from internet Apr. 6, 2017.
Attri et al. "Generation mechanism of hydroxyl radical species and its lifetime prediction during the plasma-initiated ultraviolet (UV) photolysis." Scientific Reports 5, Article No. 9332 (2015).
PCT/US2017/037762 PCT Search Report and Written opinion dated Nov. 20, 2017 in 21 pages.
Sadowitz, Benjamin et al., A Novel Non-Thermal Plasma/Free radical Sterilization System for Burn Wound Disinfection, Burn Poster EAST 2013 Compatibility Mode, University of Colorado Denver, Anschutz Medical Campus, College of Engineering and Applied Science in 1 page.
Advance Sterilization Products, Amendment Sterrad ® 50 Sterilizer K981625, dated Jan. 5, 1999 in 6 pages.
Plasmapp, Fast Low-Temerature Sterilization, downloaded from www.plasmapp.co.kr on Jul. 4, 2019 in 14 pages.

* cited by examiner

STERILIZATION, DISINFECTION, SANITIZATION, DECONTAMINATION, AND THERAPEUTIC DEVICES, SYSTEMS, AND METHODS

RELATED CASES

This application is a National Phase Application of PCT International Application No. PCT/US2017/037762, filed Jun. 15, 2017, which claims the benefit of US Provisional Patent Application Nos. 62/351,873, filed Jun. 17, 2016; 62/351,872, filed Jun. 17, 2016; and 62/424,319, filed Nov. 18, 2016. The entirety of each of these applications is incorporated by reference herein.

BACKGROUND

Technical Field

Several embodiments of the present disclosure relate generally to the art of generating atmospheres having sterilizing, disinfecting, sanitizing, decontaminating, and/or therapeutic aspects, and more particularly to sterilization, disinfection, sanitization, and/or decontamination of therapeutic devices, as well as related systems and methods.

Description of the Related Art

Sterilization, disinfection, sanitization, and decontamination methods are used in a broad range of applications, and have used an equally broad range of sterilization, disinfection, sanitization, and decontamination agents. The term "sterilization" generally refers to the inactivation of biocontamination, especially on inanimate objects. The term "disinfection" generally refers to the inactivation of organisms considered pathogenic. Although the term "sterilization" may be used in describing certain embodiments herein, it would be appreciated that such embodiments can also be used for disinfection, sanitization, and/or other types of decontamination, e.g., as provided with their regulatory definitions.

Sterilization is also important in the wound space. Existing wound therapy includes a standard procedure of care for treatment for chronic wounds, those that last longer than 30 days, that starts with physical debridement. This mechanical process, which involves resection of nonviable cells from abscessed tissues, ensures complete removal of bacterial biofilms that inhibit the healing process. Depending on the severity and longevity of the wound, patients may require antibiotic therapy, either through intravenous or oral applications. Beyond debridement and antibiotics, other treatments have been developed including Negative Pressure Wound Therapy (NPWT), Hyperbaric Oxygen Therapy (HOT), Biological Dressings (BD), and Hydrogels. Negative Pressure Wound Therapy, also known as vacuum assisted wound therapy, is a noninvasive wound closure system that uses controlled, localized sub-atmospheric (negative) pressure to promote healing. Pressure is maintained continuously or intermittently via a pump to a sterile, latex free polyurethane or polyvinyl alcohol foam dressing. Hyperbaric Oxygen Therapy, another active treatment, relies on patients sitting in a pressurized chamber of pure oxygen to increase their blood oxygen levels. Biological dressings, such as allogeneic bi-layers, are cultured from skin equivalents to create a living dressing to aid in chronic wound treatment. Hydrogels, such as Becaplermin, contain platelet derived growth factors that theoretically promote wound healing.

It is known that pulsed or silent electric discharge in air or other gases produces non-thermal plasma. Non-thermal plasma processing involves producing plasma in which the majority of the electrical energy goes into the excitation of electrons. These plasmas are characterized by electrons with kinetic energies much higher than those of the ions or molecules. The electrons in these plasmas are short-lived under atmospheric pressure; instead they undergo collisions with the preponderant gas molecules. The electron impact on gas molecules causes dissociation and ionization of these molecules, which creates a mix of reactive species, in the form of free radicals, reactive oxygen and nitrogen species, ions, and secondary electrons. These reactive species cause unique and diverse chemical reactions to occur, even at relatively low temperatures. These chemical reactions are utilized in low temperature decontamination and sterilization technologies. While there are certain non-thermal plasma devices for wound treatment (or disinfection, sterilization, etc. of devices and objects), prior to the embodiments disclosed herein, all suffered from various therapeutic and practical limitations. First, all of these devices require interaction between the plasma and the wound (or object); that is, since the electric discharge takes place directly on the tissue, the treated tissue itself plays the role of an electrode. This makes the application of non-thermal plasma exquisitely sensitive to small movements or changes in geometry. This adds significant complexity to the treatment and requires the provider to have specialized training to maintain the proper tolerances. Other limitations include the inability to cover large surface areas in a short period of time and equipment that has a large environmental footprint and requires a high upfront cost. Additionally, current commercialized non-thermal plasma devices have a requirement for significant provider training and time to administer treatment including one on one provider to patient care.

It is also known to use vaporized hydrogen peroxide (VHP) for sterilization. Known methods of sterilization with VHP include open loop systems, in which the VHP is applied to the items to be sterilized and then exhausted, and closed loop systems, where sterilizing vapors are recirculated.

In a known closed loop system, a carrier gas, such as air, is dried and heated prior to flowing past a vaporizer. A hydrogen peroxide aqueous solution is introduced into the vaporizer and which enables this solution to be vaporized. The resulting vapor is then combined with the carrier gas and introduced into a sterilization chamber of varying size, shape, and material. A blower exhausts the carrier gas from the sterilization chamber and recirculates the carrier gas to the vaporizer where additional VHP is added. Between the sterilization chamber and the vaporizer, the recirculating carrier gas passes through a catalytic destroyer (where any remaining VHP is eliminated from the carrier gas), a dryer, a filter and a heater.

United States Patent Application Publication No: US 2005/0129571 A1 by Centanni discloses a closed loop sterilization system. The purpose of using the closed loop is the increase of the free radical concentration in the circulating effluent. Centanni teaches that there should be a VHP (vapor hydrogen peroxide) destroyer employed in the loop. Centanni teaches that the ozone is mixed with the hydrogen peroxide vapor and the vapor is produced by injecting hydrogen peroxide water solution on a hot plate and thus evaporating it.

SUMMARY

As disclosed herein, a variety of items or surfaces may require processing in order to reduce the bioburden and decrease risk of infections. For example, critical items (such as surgical instruments, which contact sterile tissue), semi-critical items (such as endoscopes, which contact mucous membranes), and noncritical items (such as stethoscopes, which contact only intact skin) require various types of treatment, for example sterilization, high-level disinfection, and low-level disinfection, respectively. The present disclosure provides for various systems, devices and methods for disinfecting/sanitizing various items (e.g., medical devices or electronics) and surfaces (e.g., workspaces, patient rooms, organic material, including but not limited to patient wounds).

Various systems, devices, and methods are provided for herein in order to accomplish disinfection of one or more items, surfaces etc. Additionally, in several embodiments the systems, devices and methods are configured to allow low or high level disinfection. In still additional embodiments, the systems, devices and methods are configured to allows sterilization.

For example, provided for herein in several embodiments, is a system for high-level disinfection of at least one item, comprising a first unit comprising a disinfectant generator, a second unit comprising a chamber for containing an item or items to be disinfected and configured for at least temporarily fluidic communication with the first unit and at least one conduit in fluidic communication with the first unit and the second unit, wherein the conduit is configured to convey the disinfecting effluent from the first unit to the second unit. In several embodiments, the disinfectant generator is configured to generate a disinfecting effluent capable of destruction of vegetative microorganisms, mycobacterium, small or nonlipid viruses, medium or lipid viruses, fungal spores, and bacterial spores on the at least one item.

In several embodiments, the disinfectant generator comprises a free radical generator. Depending on the embodiment, the free radical generator generates one or more of types of free radical, such as ozone, superoxide, singlet oxygen, peroxide, hydroxyl radicals, nitric oxide, hydrogen peroxide, nitrous oxide, nitrogen dioxide, or peroxynitrite. In several embodiments, the free radical generator is configured to generate more than one type of free radical. In several embodiments, multiple free radical generators are included in the system, either of different free radical generating capacities, or capable of operating together to generate more than one type of free radical. In several embodiments, the free radical generator also comprises a reservoir of disinfectant media. In several embodiments, the reservoir is in fluid communication with a vaporizer unit, wherein the vaporizer unit is configured to generate a vapor of the disinfectant media. Some embodiments involve generation of a mist of disinfectant media. In several embodiments, the free radical generator comprises a gas distribution unit, wherein the gas distribution unit is in fluidic communication with the free radical generator and the reservoir of disinfectant media. In several embodiments, the gas distribution unit conveys a gas (e.g., recycled effluent or atmospheric gas) from at least one outlet of the gas distribution unit to an inlet of the free radical generator and to the reservoir of disinfectant media or the vaporizer unit.

In several embodiments, the chamber of the second unit comprises a sealed and enclosed area in which the item or items to be disinfected may be placed. In several embodiments, the chamber comprises a first portion and a second portion configured to reversibly and interact with one another to form a sealed and enclosed area. In several embodiments, there is provided an insert configured to be placed within the sealed and enclosed area (be it a unitary or multipart chamber), the insert configured to contain the at least one item to be disinfected. There is also, in several embodiments, at least one seal on the chamber that is configured to allow entry of the disinfecting effluent into the sealed and enclosed area. Some embodiments also employ that seal to allow an egress of disinfecting effluent. In several embodiments, the at least one seal is configured to maintain the sealed and enclosed area as sealed upon cessation of the temporarily fluidic communication with the first unit. Thus, in such embodiment, the chamber acts as a self-contained environment and transport/storage unit for the item(s).

In several embodiments, the system further comprises a controller unit, wherein the controller unit is configured to control the activation of the first unit and the conveyance of the disinfecting effluent from the first unit to the second unit.

In several embodiments, the disinfectant generator comprises a vaporizer that is configured to generate a vapor or mist of the disinfectant media. In some embodiments, the disinfectant media is atomized or otherwise suspended in a gaseous medium to be conveyed to the chamber. In several embodiments, the disinfectant media may be in a powder format (e.g., analogous to powder coating). In several embodiments, the vaporizer comprises a wicking material disposed within the disinfectant media and positioned to have at least a portion of the gas distributed by the gas distribution unit across or through the wicking material. In such embodiments, the flow of gas across or through the wick facilitates the formation of the vapor or mist of disinfectant media. In several embodiments, the vaporizer comprises a bubbler configuration wherein at least a portion of the gas from the gas distribution unit it bubbled into the disinfectant media to generate the vapor. Depending on the embodiment, the disinfectant media comprises a liquid and the vaporizer comprises a float sensor configured to regulate the level of the disinfectant media.

In several embodiments, the gas distribution unit comprises at a first and a second conduit, wherein the first conduit is in fluid communication with the free radical generator and wherein the second conduit is in fluid communication with the vaporizer unit.

In several embodiments, the system includes at least one conduit exiting the free radical generator and at least one conduit exiting the vaporizer unit, wherein the conduit from the free radical generator and the conduit from the vaporizer unit enter the second unit comprising the chamber. In several embodiments, the conduit from the free radical generator and the conduit from the vaporizer unit are integrated into a single conduit that enters the second unit comprising the chamber (e.g., they are joint at a point prior to entering the chamber). In alternative embodiments, the chamber receives a separate inflow of free radicals and vaporized disinfectant media, which are mixed together in the chamber based on gas flow patterns within the chamber. In several embodiments, the chamber further comprises at least one conduit exiting the chamber, wherein the at least one conduit is fluidically connected with the disinfectant generator. In several such embodiments, the at least one conduit fluidically connected with the disinfectant generator recycles disinfectant effluent from the chamber back to the disinfectant generator. In such embodiments, there is potential for recycling disinfectant effluent that may still be "live"—in other words has the ability to continue to disinfect/sterilize an item. This leads to higher efficiency, in several embodiments, as the plasma generator and vaporizer can be adjusted in a tailored fashion to prevent generation of excess free radicals and/or disinfectant/sterilant.

In several embodiments, the second unit further comprises an additional conduit that fluidically connects an interior of the chamber with an exterior environment. In several embodiments, the additional conduit comprises one or more of a filter, a free radical destroyer and a blower.

In several embodiments, the first portion of the second unit comprises an inlet and an outlet configured to receive into the chamber and allow to exit the chamber the disinfectant effluent generated by the disinfectant generator.

In several embodiments, the system is configured to operate in an open-loop mode, wherein the system is configured to allow atmospheric gas to enter the chamber.

In several embodiments, the system is further configured to operate in a closed-loop mode following the open-loop mode, wherein the closed loop mode restricts gas flow into and out of the chamber to gas comprising the disinfectant effluent generated by the disinfectant generator.

In several embodiments where the chamber is formed from multiple parts (e.g., a first and a second, though additional multi-part chambers are provided for as well), the first part and the second part of the second unit are at least partially joined with one another. In several embodiments, the insert of the second unit is configured to receive and contain the at least one item based at least in part on a dimension or shape of the at least one item.

Depending on the embodiment, a variety of different items or surfaces can be treated (e.g., sterilized or disinfected). For example, in several embodiments the at least one item to be disinfected comprises an internal lumen and the second unit and the insert are configured to convey disinfectant effluent through the internal lumen. In several embodiments, the second unit is configured to convey disinfectant effluent around an exterior surface of the at least one item. In still additional embodiments, the second unit is configured to allow disinfection of a plurality of items, each of the plurality of items comprising an internal lumen. In several embodiments, the second unit is configured to store the at least one item until a subsequent use of the at least one item. Such embodiments, may involve second units that are configured to stack or nest with at least one additional second unit. In several embodiments, the second unit is substantially rigid, while in other embodiments, the second unit is flexible. In several embodiments, the insert is configured to contain a plurality of items of particular shapes and sizes, and wherein the insert is configured with a specific receiving area for each of the plurality of items.

In several embodiments, the system includes an additional conduit fluidically communicating with an exterior environment and an interior of the chamber. In several embodiments, that additional conduit further comprises one or more of a valve to control gas flow from the environment to the interior of the chamber, a filter, and a heater element. In such embodiments, the conduit can be used to allow a pre-treatment gas into the chamber, e.g., to dry and heat the chamber prior to initiating a sterilization or disinfection cycle.

In several embodiments, the free radical generator is a cold plasma generator that generates ozone. In several embodiments, the reservoir of disinfectant media comprises a liquid or solid source of hydrogen peroxide.

Several embodiments provided for herein are particularly advantages for treating a variety of types of items or surfaces, as in several embodiments, the system operates at a pressure not significantly different from an ambient environmental pressure. In some embodiments, the system operates at a pressure between about 600 mm Hg and 800 mm Hg. In several embodiments, the system operates at or around an ambient temperature, for example in several embodiments, the system operates at a temperature ranging from about 15 degrees Celsius to about 50 degrees Celsius. In some embodiments, the system operates at a humidity within an interior of the chamber of between about 20% and 90% relative humidity. Such embodiments advantageously allow for the optional use of the system to achieve high-level disinfection (or sterilization) of electronic devices. In some embodiments, the system further comprises at least one desiccant depot configured to assist in maintaining the humidity.

In several embodiments, the system allows for high-level disinfection to be achieved in a cycle time of between about 120 seconds to about 10 minutes. In some embodiments, sterilization can be achieved in times ranging from about 5 to about 20 minutes.

There are also provided for herein various methods for disinfecting (or sterilizing) at least one item, comprising placing the at least one item in the insert of a system disclosed herein and activating the system to expose the at least one item to the disinfectant effluent for an amount of time sufficient to achieve high-level disinfection of the at least one item.

In several embodiments, a method for disinfecting at least one item comprises placing the at least one item an insert configured to contain the at least one item, placing the insert in a chamber that forms a sealed and enclosed area around in the insert and the at least one item, activating a disinfectant generator, wherein the disinfectant generator comprises a free radical generator and a reservoir of disinfectant media in fluid communication with a vaporizer unit.

In several embodiments, the disinfectant generator is configured to generate a disinfecting effluent capable of destruction of vegetative microorganisms, mycobacterium, small or nonlipid viruses, medium or lipid viruses, fungal spores, and bacterial spores on the at least one item. In several embodiments, the activation of the disinfectant generator causes disinfecting effluent to enter the chamber and disinfect the at least one item. Similar methods are employed, in several embodiments, to sterilize an item (or items) and/or a surface or wound.

In several embodiments, the activation of the system also activates a gas distribution unit that conveys the disinfecting effluent to move from the disinfectant generator to the chamber. In several embodiments, activation of the system first results in the system operating in an open-loop mode where the chamber is open to receive atmospheric gases followed by a closed-loop mode where the chamber is open to receive only disinfecting effluent. In such embodiments, the open-loop mode is configured to heat and dry the chamber and the at least one item within the chamber. In some embodiments, the open-loop mode is configured to dry the chamber by heat and/or dry air and the at least one item within the chamber. Not all embodiments employ the open loop configuration, some embodiments operate only on a closed-loop method. In several embodiments, the methods employ disinfecting effluent comprising vaporized hydrogen peroxide and free radicals. In some embodiments, the interior of the chamber does not experience a pressure significantly different from an ambient environmental pressure. In several embodiments, the interior of the chamber is heated or cooled to a temperature ranging from about 15 degrees Celsius to about 50 degrees Celsius. In several embodiments, the interior of the chamber is maintained at a humidity of between about 20% and 90% relative humidity. In several embodiments, the methods allow for high-level disinfection to be achieved in a cycle time of between about 120 seconds to about 10 minutes. As discussed above, in several embodiments, the methods disclosed herein allow for sterilization to be achieved in cycle times ranging from about 5 to about 20 minutes.

There is also provided for herein a system for treating at least one item, whether organic or inorganic, or surface, comprising a first unit comprising a disinfectant generator, wherein the disinfectant generator comprises a free radical generator, wherein the free radical generator generates free radicals, a vaporizer unit in fluidic communication with a reservoir of disinfectant media, wherein the vaporizer unit is configured to generate a vapor of the disinfectant media, a gas distribution unit, wherein a gas from at least one outlet of the gas distribution unit to an inlet of the free radical generator and to the reservoir of disinfectant media or the vaporizer unit, wherein the disinfectant generator is configured to generate an effluent capable low-level disinfection, high-level disinfection or sanitization of the at least one item, a second unit comprising a chamber for containing an item or items to be treated, wherein the chamber is configured to form a sealed and enclosed area which can receive the at least one item, and at least one conduit in fluidic communication with the first unit and the second unit, wherein the conduit is configured to convey the disinfecting effluent from the first unit to the second unit.

Depending on the embodiment, the system can be configured for high-level disinfection of the at least one item. Alternatively, the system can be configured for sanitization of the at least one item. In some embodiments, the system is configured for treatment of a plurality of items, each of the plurality of items having an internal lumen. In several embodiments, the system further comprises an insert configured to be placed within the sealed and enclosed area, the insert configured to contain the at least one item to be treated. In several embodiments, the system is configured for treatment of an organic surface. In some such embodiments, the organic surface is a food item. In several embodiments, the organic surface is a wound (e.g., an open wound). In several embodiments, the chamber is flexible, optionally customizable, and configured to enclose the wound.

Further provided for herein is a sterilization, disinfection, sanitization, or decontamination system comprising a sterilant source that generates sterilant, a chamber configured to contain an item to be sterilized, disinfected, sanitized, or decontaminated and to receive the sterilant from the sterilant source, a flow generator configured to circulate the sterilant from the sterilant source to the chamber in a closed-loop such that the sterilant sterilizes, disinfects, sanitizes, or decontaminates the item in the chamber; and a residual coating source that generates a bactericidal coating, wherein the flow generator is configured to circulate the bactericidal from the residual coating source to the chamber in a closed-loop such that the bactericidal coating is deposited on the item in the chamber.

In several embodiments, the bactericidal coating comprises silver. In several embodiments, the bactericidal coating comprises copper. In some embodiments, combinations of copper and silver are used. In several embodiments, the bactericidal coating comprises a sacrificial layer. In several embodiments, the system is configured to deposit the bactericidal coating on the item in the chamber after the flow generator circulates the sterilant.

In several embodiments, the sterilant source comprises a plasma generator configured to generate free radicals and wherein the sterilant comprises the free radicals. Depending on the embodiment, the sterilant source is optionally places within the chamber, while in some embodiments, the sterilant source is outside the chamber.

In several embodiments, the sterilant source comprises an evaporator configured to receive hydrogen peroxide and generate hydrogen peroxide vapor and wherein the sterilant comprises the hydrogen peroxide vapor.

In some embodiments, the system is configured to deliver sterilant to a wound on a subject, wherein the wound is at least partially surrounded by a drape or patch that creates a dead space between the drape or patch and the wound, wherein the sterilant flows through the dead space. In some such embodiments, the sterilant is delivered at a negative pressure. In several embodiments, the sterilant comprises reactive oxygen and/or nitrogen species (RONS) and vaporized hydrogen peroxide (VHP).

Additionally provided for herein, in several embodiments, is a sterilization, disinfection, sanitization, or decontamination system comprising an evaporator configured to receive a level of liquid agent at a first location, generate a vapor from the liquid agent, and release the vapor at a second location, a chamber configured to contain an item to be sterilized, disinfected, sanitized, or decontaminated and to receive the vapor from the evaporator; and a flow generator configured to circulate the vapor from the chamber to the evaporator in a closed-loop such that the vapor sterilizes, disinfects, sanitizes, or decontaminates the item in the chamber, wherein the evaporator comprises a wicking material disposed between the first location and the second location, the wicking material configured to absorb and encourage evaporation of the liquid agent, and wherein based at least in part on the level of the liquid agent, the evaporator is configured to achieve a condensation level at or below a threshold level at the second location.

In several embodiments, the threshold level is at or below a saturation level of the vapor such that there is substantially no condensation at the second location. In several embodiments, the relative humidity is optionally monitored and actively controlled during the sterilization cycle. In several embodiments, the system also includes a measuring device configured to measure the level of liquid agent, wherein based at least in part on the measured level, the evaporator is configured to adjust the level of liquid agent at the first location. For example, in one embodiment, the measuring device is a switch float.

In several embodiments, the evaporator further comprises a vibration element configured to create a mist of the liquid agent at or near the first location. In some such embodiments, the vibration element comprises a piezoelectric vibration element. In several embodiments, the evaporator is configured to generate the vapor at or near ambient temperature. In such embodiments, the ambient temperature is approximately room temperature and/or environmental humidity in the location of the system. In several embodiments, the evaporator further comprises a drain operable to drain the liquid agent from the evaporator.

In several embodiments, the system can also include a plasma generator configured to generate free radicals to be mixed with the vapor to sterilize, disinfect, sanitize, or decontaminate the item.

Still additional embodiments provide for a sterilization, disinfection, sanitization, or decontamination system comprising a vapor generator configured to generate vapor, a chamber configured to contain an item to be sterilized, disinfected, sanitized, or decontaminated and to receive the vapor from the vapor generator, a flow generator configured to circulate the vapor from the chamber to the vapor generator in a closed-loop such that the vapor sterilizes, disinfects, sanitizes, or decontaminates the item in the chamber, an air input coupled with the chamber and configured to allow dry air into the chamber, an exhaust coupled with the chamber and configured to remove existing air from the chamber, a sensor disposed in the chamber and configured to sense a level of at least one of humidity, pressure, and temperature within the chamber; and a controller in data communication with the sensor and configured to receive the sensed level from the sensor, wherein based at least in part on a difference between the sensed level within the chamber and external the chamber, the controller is configured transmit instructions either to the exhaust to remove at least a portion of the existing air from the chamber or to the air input to allow dry air into the chamber such that a condensation level in the chamber is at or below a threshold level.

In several embodiments, the threshold level is such that there is substantially no condensation in the chamber. In several embodiments, after the exhaust removes at least a portion of the existing air from the chamber, the air input in response allows dry air into the chamber. In several embodiments, the air input allows dry air into the chamber, the exhaust in response removes at least a portion of the existing air from the chamber. In some embodiments, the system also includes a sensor configured to sense whether the chamber is open, wherein the controller is further configured to execute instructions in order to, in response to determining with the sensor that the chamber is open, transmit instructions to the vapor generator to shut down and to the exhaust to remove the existing air from the chamber. In several embodiments, the vapor generator comprises an evaporator or a plasma generator.

Still additional systems are provided for herein, such as a sterilization, disinfection, sanitization, or decontamination system, comprising an effluent generator configured to generate effluent, wherein the effluent generator comprises a plasma generator, a chamber configured to contain an item to be sterilized, disinfected, sanitized, or decontaminated, the chamber comprising an input configured to receive the effluent from the effluent generator, a flow generator configured to circulate the effluent from the chamber to the effluent generator in a closed-loop, and a dryer disposed in a path of the closed-loop between the flow generator and the plasma generator. In several embodiments, the system includes a sensor disposed in the chamber and configured to sense a level of at least one of humidity, pressure, and temperature within the chamber and a controller in data communication with the sensor and configured to receive the sensed level from the sensor. In several embodiments, based at least in part on a difference between the sensed level within the chamber and external the chamber, the controller is configured transmit instructions to the dryer to dry at least a portion of the effluent entering the plasma generator such that a condensation level at the input of the chamber is at or below a threshold level.

In several embodiments, the threshold level is set at a level such that there is substantially no condensation in the chamber. In several embodiments, the path of the closed-loop between the flow generator and the plasma generator comprises a first branch and a second branch, wherein the dryer is disposed in the first branch and comprises a dry valve such that when the dry valve is opened, at least a portion of the effluent enters the dryer. In several embodiments, the system also includes a plasma valve in the second branch such that when the plasma valve is closed, the plasma valve blocks the effluent from entering the plasma generator through the second branch. In one embodiment, the effluent generator comprises an evaporator.

Also provided for herein is a chamber for sterilizing, disinfecting, sanitizing, or decontaminating one or more wounds on a patient, the chamber comprising an intake port configured to receive gaseous effluent from a effluent generator, an exhaust configured to return the gaseous effluent in the chamber to the effluent generator. an inflatable structure configured to be inflated by the gaseous effluent such that the inflatable structure does not come into contact with the one or more wounds on the patient and such that the gaseous effluent can circulate within the inflatable structure, and a sealing device that substantially seals the inflatable structure to the patient and thereby substantially containing the gaseous effluent within the inflatable structure. In several embodiments, the chamber includes an access port that enables a user to access the one or more wounds while the chamber is fitted to the patient. In several embodiments, the sealing device comprises a cuff and wherein the inflatable structure is configured to fit over at least a portion of the patient's arm or leg. In several embodiments, the cuff comprises latex.

There is additionally provided for a sterilization, disinfection, sanitization, or decontamination system for an appliance having a chamber with a closed space, the system comprising an effluent generator configured to generate effluent, wherein the effluent generator comprises at least one of: an evaporator and a plasma generator, a flow generator configured to circulate the effluent in a closed loop between the chamber and the effluent generator; and a Free Radical Destroyer (FRD) to remove free radicals from the effluent before it is discharged into the environment or into the room at the end of the cycle. In one embodiment, the plasma generator comprises an ozone generator. In one embodiment, the evaporator comprises a hydrogen peroxide evaporator. In one embodiment the appliance is a washing machine, dryer, microwave, dishwasher or other appliance with an enclosed chamber. In several embodiments, the system is used for room sterilization and wherein the system further comprises an effluent generator configured to generate effluent of varied humidity. In one embodiment, the effluent generator is placed in the room. In an alternative embodiment, the effluent generator is placed outside of the room and delivers the circulating sterilant to the room through input and output conduit.

The present disclosure provides various embodiments of devices, systems, and methods which can generate atmospheres having sterilizing, disinfecting, sanitizing, decontaminating, and/or therapeutic aspects. In several embodiments, the generated atmospheres undergo a relatively gentle process that is compatible with all materials (e.g., natural and manmade), live tissue, and electronics. In some embodiments, the generated atmospheres are produced with a "green" process, e.g., utilizing relatively low power consumption and producing non-toxic products and by-products. In some embodiments the sterilizing, disinfecting, sanitizing, decontaminating and/or therapeutic procedure is used as a singular therapy. In some embodiments the sterilizing, disinfecting, sanitizing, decontaminating and/or therapeutic procedure is used in conjunction with active and/or passive wound treatment modalities. These treatment modalities can include, but are not limited to, debridement, biological dressing(s), hydrogels, negative pressure wound therapy, and other treatment modalities. In some embodiments, one or more of these modalities are integrated with the sterilizing, disinfecting, sanitizing, decontaminating devices and/or therapeutic procedures as disclosed herein.

In several embodiments, a combination of reactive oxygen and/or nitrogen species (RONS) and vaporized hydrogen peroxide (VHP) provides significant and unexpected advantages over alternative technologies. In several embodiments, a RONS and VHP combination is eco-friendly because no harsh chemicals are used in the process and there are no residuals post processing from the sterilant. Another advantage of the RONS and VHP combination technology is flexible treatment coverage. For example, in wound healing, using patches, boots, sleeves, arm cuffs (and the like) of various sizes. This enables treatment to be administered to a range of areas, e.g., from small to whole body doses (in the case of treating burn victims). Furthermore, the treatment process is streamlined because sterilant circulates continuously across the wounded area without requiring provider supervision once a patch, boot, or arm cuff is applied. One embodiment of the RONS and VHP combination device is lightweight (e.g., 15 pounds or less) allowing it to be used for units that are portable (e.g., mounted on a pole or other mobile furniture). Additionally, some embodiments of the RONS and VHP combination technology have a reasonably low cost of goods that allow greater access and widespread use of the technology (e.g., a medical facility can employ multiple devices, which reduces risk of patient to patient (or provider) infection.

The present disclosure provides various embodiments of devices, systems and methods for sterilization, disinfection, sanitization, and/or decontamination of, for example, patient to patient, patient to caregiver, caregiver to patient, caregiver to caregiver, other personnel that are employed by or visit health care facilities, regulated and unregulated medical devices, medical equipment, heat and/or moisture sensitive devices or items, and in particular interior and/or exterior surfaces of small diameter or sensitive medical equipment. Some embodiments of the present disclosure relate to use in the veterinary field including devices, systems and methods for sterilization, disinfection, sanitization, and/or decontamination of, for example, a veterinarian treating an animal patient. As described above, in several embodiments, the variations in size of the device are advantageous in the veterinary space, given the wide range of animal sizes. In several embodiments, the devices and methods disclosed herein are useful for animal shelters, in order to limit spread of infection or disease for animals not having received normal veterinary care. Various embodiments may also be used outside healthcare facilities in a variety of industrial and consumer applications.

In several embodiments, there are provided systems and devices for delivering gaseous mixture of hydrogen peroxide vapor and cold plasma effluent (sterilant) under therapeutic parameters to reduce a targeted infection in a subject. Certain embodiments include devices and systems for delivering pressurized sterilant (or lower than atmospheric pressure or intermittent pressures) to reduce bioburden and promote healing in the wounds of a subject having one or more health conditions, including, but not limited to, skin and soft tissue infections (SSTIs), sepsis, localized infection, and/or osteomyelitis. Some embodiments disclosed herein relate to reducing pathogenic infections in soft tissue of a subject in order to promote wound healing in persistent or chronic wounds.

Several embodiments of the present disclosure provide a gaseous sterilant delivery device for delivering an ambient/pressurized/under-pressurized sterilant to a subject. In some embodiments, the device includes a source of sterilant functionally coupled to a subject interface unit, optionally a gas flow regulator that measures flow rate of the sterilant and optionally a gas pressure regulator that measures pressure of the sterilant as the sterilant is delivered through the subject interface unit to the subject, wherein the sterilant treats an infection in or on the subject.

In several such embodiments, the pressure of the sterilant delivered to the subject is from about 0.05 ATM to about 2.0 ATM, in particular about 0.15 ATM to about 1.0 ATM, and any values in between. In additional embodiments, the pressure ranges from about 0.05 ATM to about 0.10 ATM, about 0.10 ATM to about 0.15 ATM, about 0.15 ATM to about 0.20 ATM, about 0.20 ATM to about 0.25 ATM, about 0.25 ATM to about 0.50 ATM, about 0.50 ATM to about 0.75 ATM, about 0.75 ATM to about 1.0 ATM, about 1.0 ATM to about 1.5 ATM, about 1.5 ATM to about 1.75 ATM, about 1.75 ATM to about 2.0 ATM, and any pressure in between, including endpoints. In some other embodiments, the sterilant is delivered at ambient pressure.

In several embodiments, wherein the under-pressure of the sterilant delivered to the subject is from about −10 mm Hg to about −300 mm Hg, in particular about −10 mmHg to about −180 mmHg, and any values in between. For example, in some embodiments, the under-pressure ranges from about −10 mmHg to about −20 mmHg, −20 mmHg to about −30 mmHg, −30 mmHg to about −50 mmHg, −50 mmHg to about −70 mmHg, −70 mmHg to about −100 mmHg, −100 mmHg to about −120 mmHg, −120 mmHg to about −150 mmHg, −150 mmHg to about −180 mmHg, −180 mmHg to about −200 mmHg, −200 mmHg to about −250 mmHg, −250 mmHg to about −300 mmHg, and any pressure in between, including endpoints.

Several embodiments of the present disclosure also provide strict control of relative humidity (RH) delivered to the subject. RH of the circulating sterilant can vary during the sterilizing cycle according to the preprogrammed levels. Several embodiments disclosed herein include a relative humidity sensor.

In several embodiments, the humidity of the sterilant delivered to the subject in some parts of the cycle, especially during the beginning of the cycle, vary from about 20% to about 90%, and any values in between. In some embodiments, the humidity during the beginning of the cycle varies from about 20% to about 30%.

Several embodiments disclosed herein also include sterilization with UV light. In some embodiments the sterilization system further includes a UV light source in a chamber. In some embodiments, a UV light shelf is used to sterilize the bottom of an object placed directly on it.

Several embodiments disclosed herein also include one or more $N_2O$, $NO$, $NO_2$ sensors.

Several embodiments disclosed herein also include one or more oxygen and/or ozone, $H_2O_2$ sensors.

Several embodiments disclosed herein also include a gas flushing mechanism to reduce the incidence of or prevent a subject from being exposed to the sterilant when the subject interface unit is removed.

Several embodiments disclosed herein also include a subject interface unit that includes an attachment mechanism for maintaining a seal on the subject (or an area of a subject's appendage) while the sterilant gas is being delivered.

Several embodiments disclosed herein also include treating the infection in the subject that includes reducing bioburden in a wound located on the subject.

Several embodiments disclosed herein also include treating the infection in the subject by reducing one or more symptom(s) associated with the infection.

Several embodiments disclosed herein also include treating the subject by reducing the risk of developing an infection of one or more pathogenic organisms in the subject by pre-exposing them to the sterilant prior to onset of an infection at a wound site. In accordance with these embodiments, a subject can be treated with the sterilant upon presentation of a new wound.

Several embodiments disclosed herein also include treating infections that include an area of the subject's body infected by at least one pathogen selected from the group consisting of a bacterium, a virus, a fungus, a parasite, a protozoan, and an antibiotic resistant bacterium, or a combination thereof.

In several embodiments, the infection is a lesion, including, but not limited to, a surgical wound, a trauma wound, a burn, an abscess, an actinic keratosis, a keloid, a scar, skin cancer or a combination thereof.

The present disclosure also provides various embodiments of gaseous sterilization, disinfection, sanitization, and/or decontamination that can be carried out, optionally without a vacuum, at atmospheric pressure, and/or at room temperature. Some embodiments can also be carried out at slight negative pressure (e.g., as a safety precaution), slight positive pressure, and/or temperatures above or below room temperature.

The present disclosure also provides various embodiments of devices, systems, and methods for reducing or removing the build-up of mold, bacteria, bio film, and other pathogens which may arise in appliances such as dishwashers, dryers, and/or washing machines, particularly front loading washing machines and in a fruit and vegetable containment compartments of refrigerators.

The present disclosure also provides various embodiments of consumer product applications for sterilization, disinfection, sanitization, and/or decontamination. Examples of such use can include cosmetics (e.g. make up applicators), eyewear, dental products, toothbrushes, home use products for a medical condition (e.g., CPAP masks), infant care products, and pet care products. In general, the present disclosure applies to various industries that include but are not limited to, health care, sports medicine, veterinary care, dental care, agriculture, food processing, research, packaging, pharmaceuticals, home health, day care, senior care, private and public services, and military/emergency field care.

The present disclosure provides various embodiments of devices, systems, and methods for sterilization, disinfection, sanitization, and/or decontamination of food processing facilities and equipment. The provided disclosure can provide devices, system, and methods for those working with foods and in contact with potential bacteria (e.g., Salmonella, E. coli). Various embodiments involve the COP (clean out of place) step of food processing. The COP process involves cleaning, disinfecting, and decontaminating food processing equipment that has been disassembled for cleaning. Embodiments include, but are not limited to, the disinfecting and sanitizing of fittings, clamps, product handling utensils, tank vents, pump rotors, impellers, casings, and hoses. Various embodiments involve the CIP (clean in place) step of food processing. The CIP process involves cleaning the interior surfaces of food process equipment. Embodiments include, but are not limited to, the cleaning, disinfecting, and decontaminating tanks, pipes, and pumps. Various food processing embodiments involve cleaning, disinfecting, and decontaminating food contact surfaces including, but not limited to, fillers, mixers, conveyors, equipment, pipelines, tanks, vats, evaporators, and pasteurizers. Various food processing embodiments involve cleaning, disinfecting, and decontaminating non-food contact surfaces including, but not limited to, floors, walls, tables, chairs, benches, drains, troughs, and drip pans. In some embodiments the hard, non-porous, outside surface of airtight sealed packages containing food or other products are sanitized. The present disclosure provides various embodiments of devices, systems, and methods for use in sports medicine. In some non-limiting embodiments, the following items can be sterilized, disinfected, sanitized, or decontaminated: orthopedic fixtures, orthotics, ultrasound machines, and surgical implant parts.

Various advantageous embodiments of devices, systems, and methods described herein can be used without a vacuum, at constant atmospheric pressure (or slight negative or positive pressure), and/or at ambient temperature. In certain embodiments, a substantially continuous flow of sterilizing, disinfecting, sanitizing, and/or decontaminating vapor provided in a closed loop manner (optionally) without exhausting the vapor (e.g., a single cycle of continuous flow) can allow for relatively fast and efficient sterilization, disinfection, sanitization, and/or decontamination. In some embodiments, free radicals (e.g., reactive oxygen and nitrogen species—RONS) are generated using a plasma generator and/or a vaporizer to produce highly bactericidal yet non-toxic and/or gentle gaseous effluent. The effluent (e.g., reactive species and vaporized hydrogen peroxide) passes through a chamber, and then is recirculated in a closed loop system. In additional embodiments, the advantageous sterilizing, disinfecting, sanitizing, and/or decontaminating effects can be achieved in an open system. The chamber can be in the form of a movable chamber (e.g., a rotating tumbler) to sterilize, disinfect, sanitize, and/or decontaminate items like surgical masks or fabrics or medical waste, or in the form of a stationary chamber for more solid items. In several embodiments, the chamber can comprise a flexible bag or other compliant container that can encompass items of irregular shapes (or shapes that are otherwise less desirable for a dedicated type of chamber (e.g., a limb of an animal with a wound, a long catheter, etc.). In some embodiments, the chamber can comprise an entire room or a whole commercial or residential building. In some embodiments inside the chamber there is a container of custom size and shape based on the device or devices to be placed inside the container for sterilization, disinfection, sanitation, and/or decontamination. A blower may be provided inside the chamber to create turbulence. Various embodiments can be operated at room temperature so that heat sensitive materials (e.g., plastics, food, and/or live tissue) can be sterilized, disinfected, sanitized, and/or decontaminated. In several embodiments, a modest temperature increase is affected, but with temperatures remaining low enough to avoid damage to the items to be sterilized, disinfected, sanitized, and/or decontaminated. Furthermore, in some embodiments, the environment within the chamber (e.g., temperature) may be self-regulated or controlled (e.g., heated or cooled) to a condition different than the ambient conditions. In addition, the level of moisture within the chamber can be self-regulated (e.g., maintained at equilibrium) or controlled so that moisture sensitive items (e.g., electronics) can be sterilized, disinfected, sanitized, and/or decontaminated.

Various embodiments can also self-regulate and/or control moisture to reduce or avoid unwanted condensation. For example, a vaporizer or an evaporator may have a design configured to output vaporized hydrogen peroxide or other sterilizing, disinfecting, sanitizing, and/or decontaminating agent at or below the saturation level for the pressure in the chamber. By outputting the vaporized agent at such pressure levels, the evaporator can reduce or eliminate condensation of the agent at the output of the evaporator and thus also on the walls of the chamber and/or items in the chamber.

Additional devices, systems, and methods for self-regulating or controlling moisture to reduce or avoid condensation may include the regulated or controlled addition and removal of air and/or the use of a dryer in the closed-loop system to reduce the vapor saturation level of circulating effluent to desired levels.

For those embodiments used in conjunction with pre-heating and drying the items to be sterilized, disinfected, sanitized, and/or decontaminated, an input conduit equipped with a valve, heater and filter can supply fresh air to the system and an exhaust blower with an upstream filter and a free radical neutralizer can be used to remove moisture and active radicals from the system. The exhaust blower may be operated at a low speed mode during sterilization, disinfection, sanitization, and/or decontamination to create a negative-pressure condition in the chamber (e.g., approximately 1 to 2 cm of $H_2O$ lower than ambient pressure).

In several embodiments, a multi-output flow generator can be used to apportion flow in the closed loop, and also to provide multiple outlets to sterilize, disinfect, sanitize, and/or decontaminate multiple items or to feed multiple chambers. In several embodiments, tubing can be utilized to deliver sterilizing, disinfecting, sanitizing, and/or decontaminating vapor to lumens of medical and/or dental devices, particularly those with a small inner diameter and/or sensitive materials that would not be compliant with higher temperature, higher humidity, and/or pressure sterilization approaches.

Certain embodiments described herein can also be used with a wound chamber to aid healing by providing effluent to a wound. For example, a wound chamber may be used that maintains space around the patient's body and avoids/minimizes touching the wound. The wound chamber may include one or more rib structures, a multi-chamber design, or other features that provide structural support to maintain separation from the patient's wound. Therapeutic vapor may be contained within the wound chamber at a positive pressure, which may help maintain separation from the wound, or negative pressure, which may help prevent the vapor from escaping the chamber into the atmosphere. The wound chamber may include one or more access features such as ports, zippers, snaps, Velcro®, etc. that enable users of the chamber to access the wound. The wound chamber may be sealed to the patient using any suitable mechanisms, which may include a flexible cuff, tape, Velcro®, straps, or other mechanical implementations. The wound chamber may include and input line to deliver the vapor and an output line to enable recirculation of the vapor back through the effluent generator in a closed loop system. Additionally the chamber may include line connected to a vacuum pump. In some cases where it is beneficial for wound healing process to increase the pressure in the wound relative to the ambient pressure, additional line maybe connected to a pressure pump that would increase the pressure in the wound chamber. In general, it may be desirable to form the wound chamber out of biocompatible materials such as latex or suitable plastics. In some instances, a Tyvek® bag may be used.

The disclosure also presents a method of sterilizing, disinfecting, sanitizing, and/or decontaminating items using the above-described apparatus. The method includes placing the items in the chamber, pre-heating and drying them in an open-loop, disinfecting using a closed loop circulating system to supply bactericidal free radicals generated by an electric discharge with free radicals in antimicrobial liquid to the chamber, then flushing and drying the system in an open-loop.

Various embodiments can be self-contained allowing for portability and/or adaptation to relatively large scale commercial applications and/or to sterilize, disinfect, sanitize, and/or decontaminate facilities such as operating rooms, hospital rooms or entire buildings.

Some embodiments described herein can also be used for reducing or removing the build-up of mold, bacteria, biofilm, and other pathogens which may arise in appliances having closed spaces such as dishwashers, clothes dryers, and/or washing machines, particularly front loading washing machines and refrigerators.

DETAILED DESCRIPTION

General

Figure 1A:
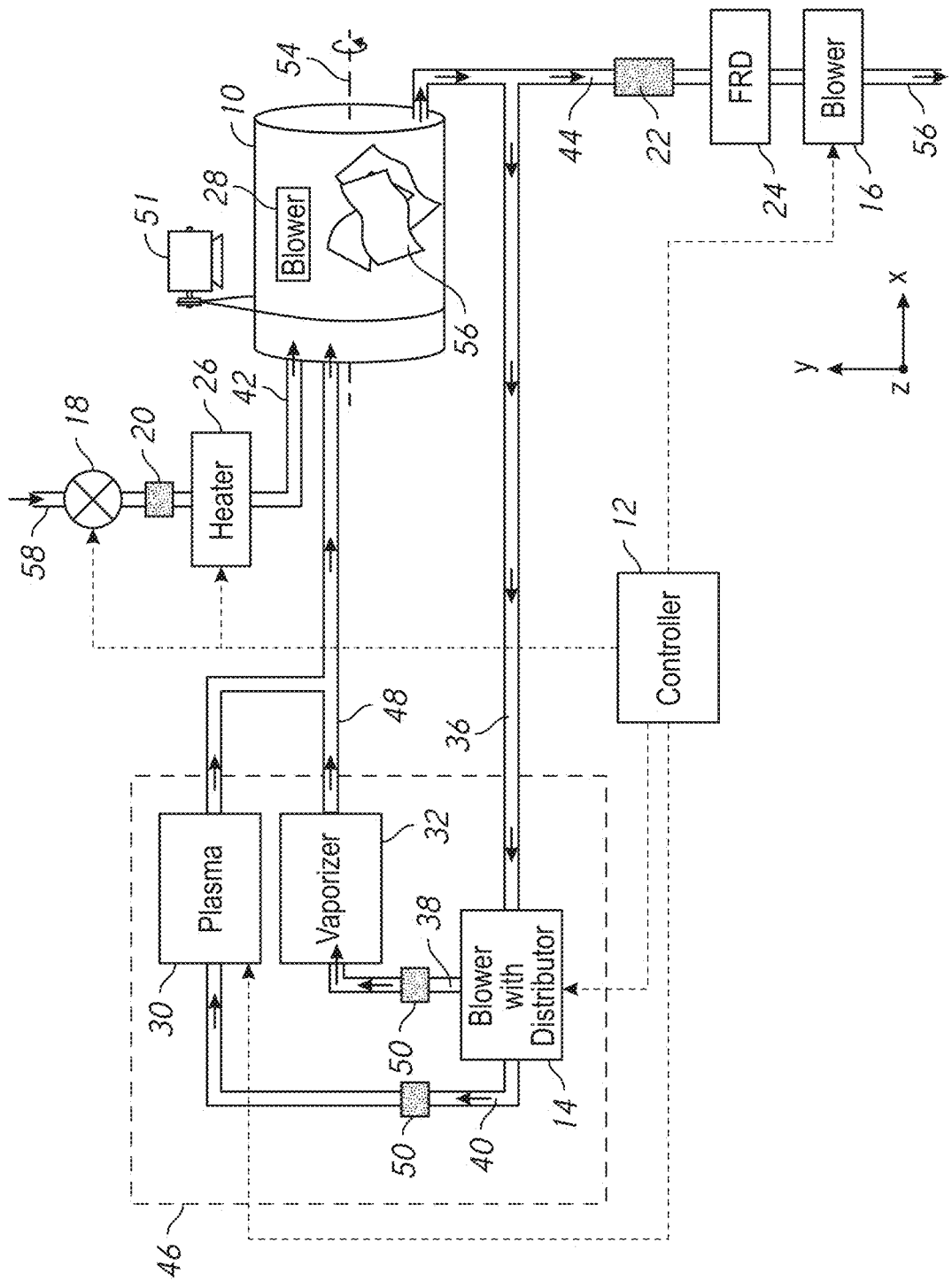
FIG. 1A shows a block diagram of a first embodiment of the disclosure with a tumbler-type chamber.

As discussed in greater detail herein the present application provides for various systems, devices, and related methods for sterilizing, disinfecting, sanitizing, and/or decontaminating a variety of items, ranging from surgical equipment or other medical devices to electronic equipment, as well as services, rooms, and other items including, but not limited to soft goods, foods, and related manufacturing equipment. A general overview will be provided, with additional detail related to each of the components of such systems and devices provided below. As mentioned above, the term "sterilization" shall be appreciated to not only encompass the removal of all or substantially all microorganisms and or other pathogens from an object or surface but shall also encompass (unless otherwise specified) disinfection, sanitizing, and decontamination.

In several embodiments, there is provided a system for sterilization that comprises a free radical generator, a vaporizer, and a chamber that encloses or otherwise contains items to be sterilized. In some embodiments, these components are directly connected to one another, e.g., are a unitary device. However, in several embodiments a variety of conduits connect the respective portions of the system together in a combination of one way, or two-way, fluidic connections between the various components.

In several embodiments, the system additionally comprises a controller element. The controller element serves to integrate and coordinate the function of the various components of the system for example cycle duration, amount of free radicals generated and introduced into the chamber and the like.

Several embodiments further comprise a flow distributor. In several embodiments, the flow distributor is fluidically connected with the free radical generator in the vaporizer. As discussed below, the free radical generator in the vaporizer can be positioned in parallel with respect to one another, or in series, with either the vaporizer or the free radical generator occupying the first position in the series, depending on the embodiment. In several embodiments, the flow distributor is fluidically connected with the free radical generator and/or the vaporizer by way of one or more conduits. Depending on the embodiment, one or both of the conduits can also comprise a filter element that functions to remove particulate matter and/or other materials from the gas being passed from the flow distributor to the free radical generator and/or vaporizer. Various embodiments employ different types of filters, such as charcoal filters, HEPA filters, and the like, as discussed in more detail below.

A fluidic connection is also provided, in several embodiments between the free radical generator into the vaporizer and the chamber. In other words, these conduits convey either independently or in a joined format, the effluent is generated from the free radical generator and/or vaporizer. In several embodiments a first conduit delivers the free radicals to the chamber and a second conduit delivers vaporized sterilant to the chamber. However, in other embodiments, two independent conduits meet at a junction point such that the flow of free radicals and vaporized sterilant are combined prior to, or concurrent with, entry into the chamber. In several embodiments either the controller and/or the flow distributor adjust the relative distribution of free radicals and vaporized sterilant that are combined and subsequently pass into the sterilization chamber. In some embodiments, the combination of the free radical generator, sterilant vaporizer, and flow distributor (as well as their respective fluidic conduit connections) are collectively referred to herein as the effluent generator.

In several embodiments an outlet conduit exits the sterilant chamber and provides a flow pathway for access sterilant to return to the flow distributor of the effluent generator. In several embodiments this allows recycling of unspent sterilant/free radicals and allows for a more efficient sterilization process as efficacious concentrations of sterilant can be reached within the chamber more quickly.

In some embodiments, the exit/recycling conduit leaving the sterilant chamber is bifurcated and provides an outflow pathway to the external environment. In several embodiments this conduit further comprises one or more of a filter element, a free radical destroyer, and/or on additional blower/exhaust fan. In several embodiments this additional bifurcated pathway functions when the system is operating in an open loop configuration, which is discussed in more detail below. In such embodiments remaining particulate matter that has exited the sterilant chamber, and optionally, the free radical destroyer eliminates any remaining free radicals that may have exited the chamber. The additional blower/exhaust fan serves to regulate the flow of gases along this additional bifurcated exit pathway. In some embodiments of an open loop operation, prior to the initiation of the sterilization cycle the sterilant chamber is purged and the gaseous contents of the chamber are exited to the environment through this additional bifurcated pathway, having been safely filtered with free radicals destroyed, such that the output to the environment is functionally inert.

In several embodiments, an additional environmental inlet pathway is provided that allows external environmental air to enter the system. In several embodiments this inlets has an independent entrance into the sterilization chamber. In several embodiments the inlet conduit comprises one or more of a valve (e.g., a purge valve), a filter elements, and a heater element. In some embodiments, this inlet pathway allows environmental air to be filtered, pass through the heater element, and enter the interior of the sterilization chamber, serving to warm, and dehumidifier a the interior of the sterilization chamber. In several embodiments this environmental air, after having heated and dried the interior of the sterilization chamber, exits to the environment, via the bifurcated outflow pathway briefly described above. Thereafter, in several embodiments the purge valve can be closed and the additional blower exhaust fan can be disengaged, thereby allowing sterilization system to operate in a closed loop fashion—in other words, free radicals and vaporized sterilant from the effluent generator enter the interior compartment of the sterilization chamber, exit the interior of the sterilization chamber and are recycled via conduit back to the effluent generator via the flow distributor, that is controlled by the controller element.

Figure 16:
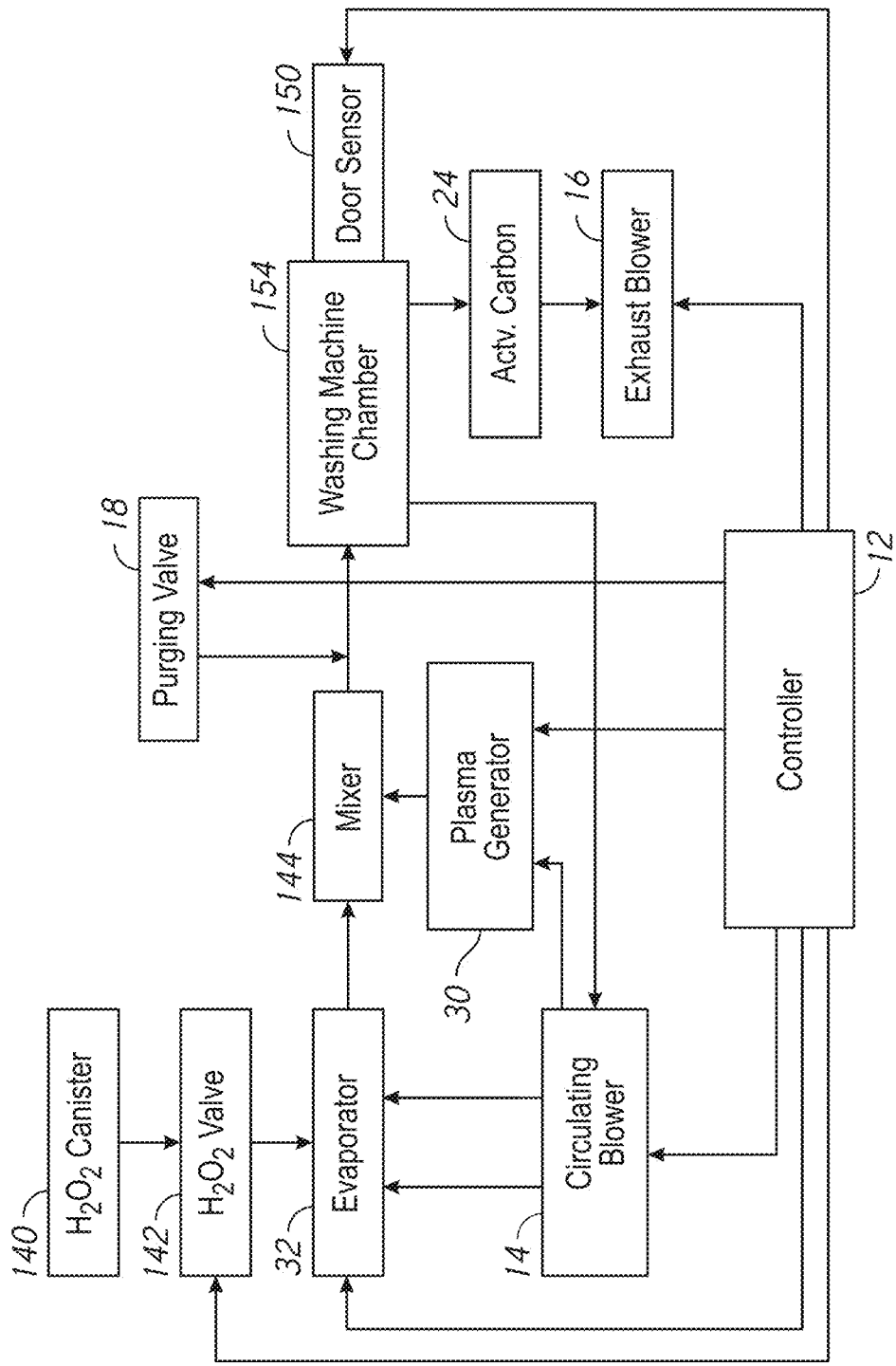
FIG. 16 shows a block diagram of an example embodiment incorporated into a washing machine.
Figure 17:
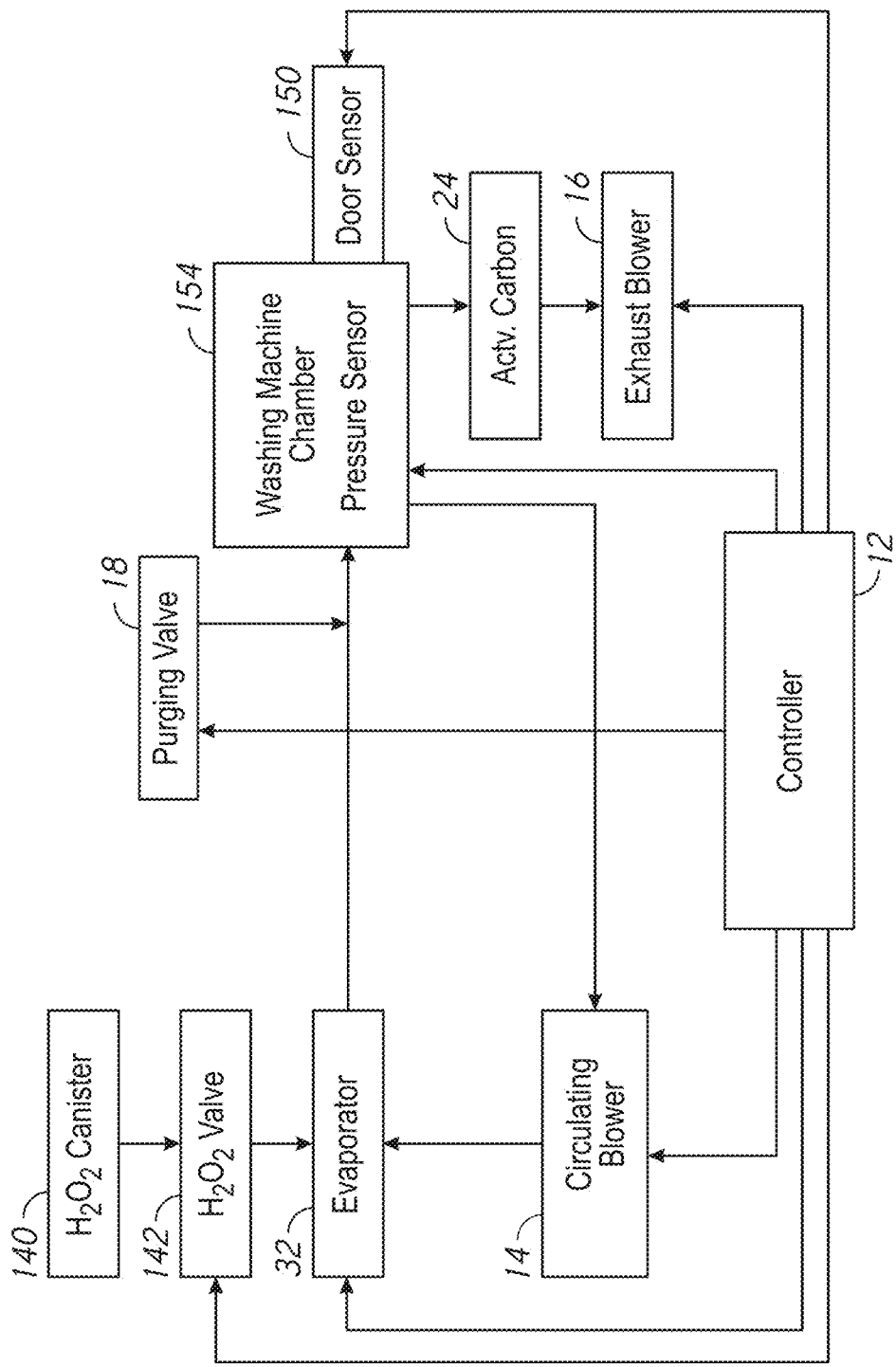
FIG. 17 shows a block diagram of another example embodiment incorporated into a washing machine.
Figure 18:
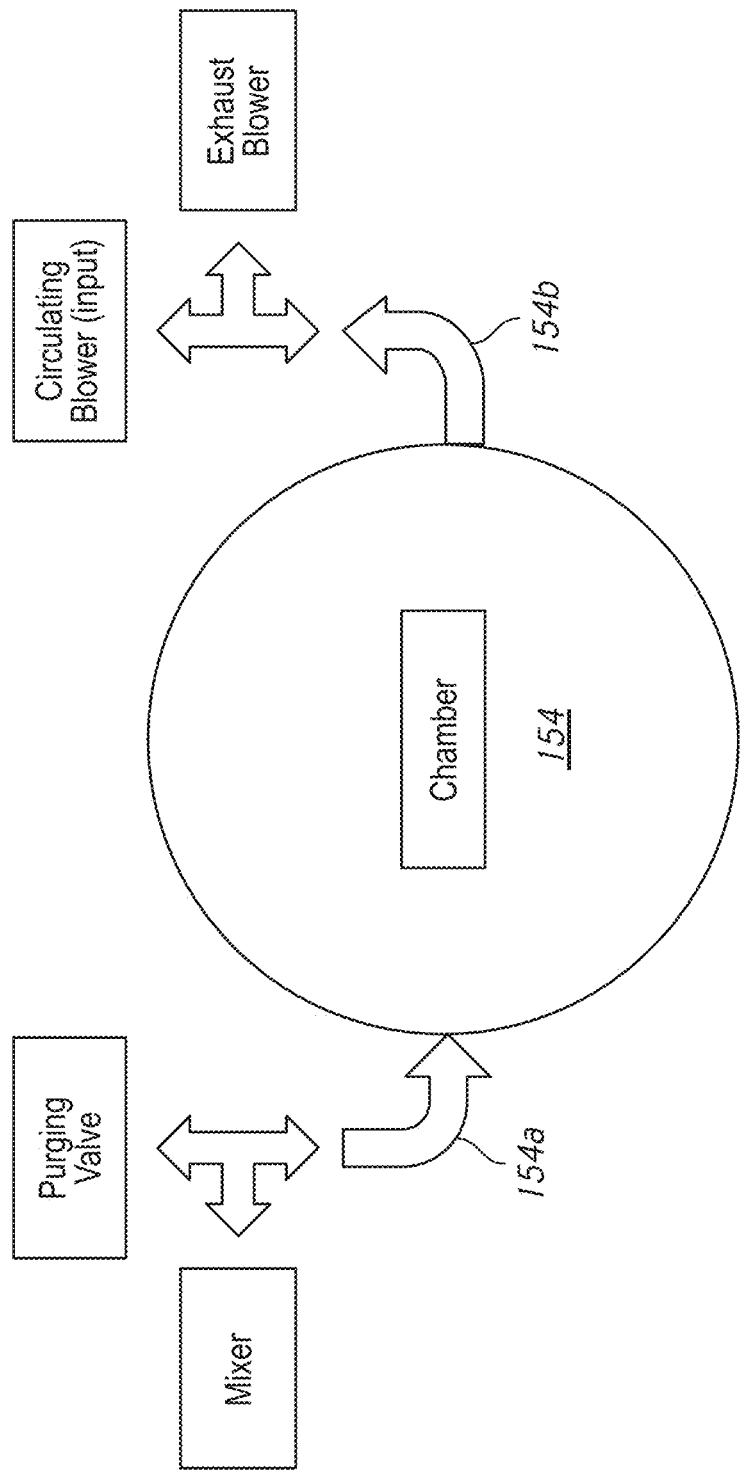
FIG. 18 shows the input and output of a washing machine chamber of some embodiments.
Figure 19:
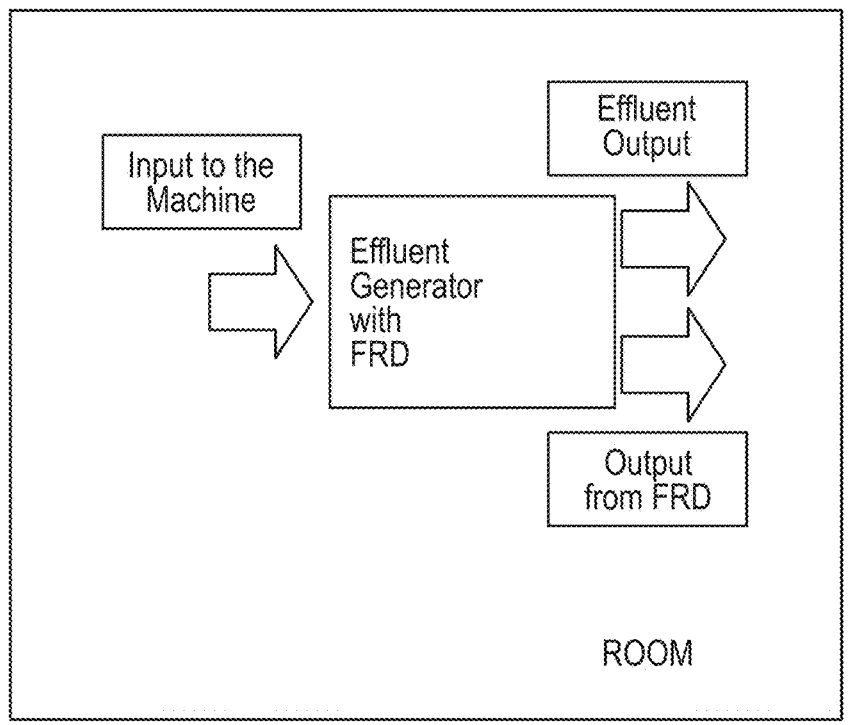
FIG. 19 shows a block diagram of an example embodiment where the sterilant is delivered to the room from an effluent generator with a Free Radical Destroyer (FRD) located in the room.
Figure 20:
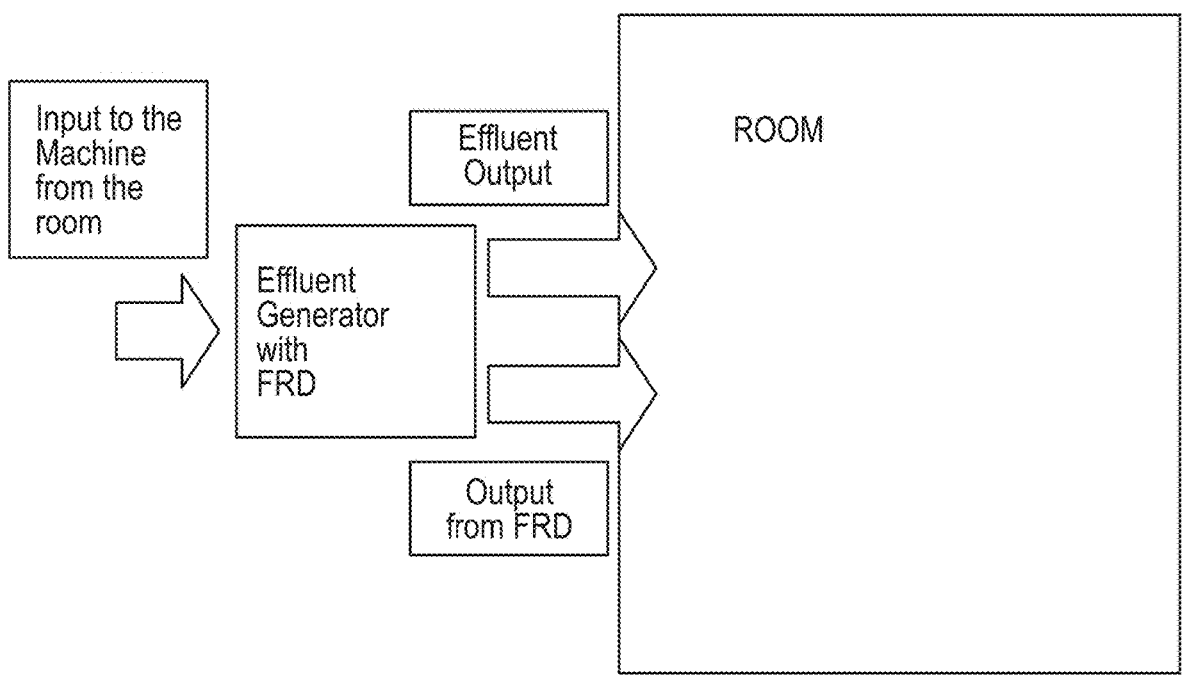
FIG. 20 shows a block diagram of an example embodiment where the sterilant is delivered to the room from an effluent generator with a Free Radical Destroyer (FRD) through the conduits, input and output, connected to the device that is outside of the room.

FIGS. 1 through 2 and 4 through 7 show block diagrams of a sterilization system, illustrating various embodiments of the present disclosure that use a sterilization chamber. FIGS. 10 to 12 and 14 to 15 show additional embodiments using a wound chamber. FIGS. 16 to 18 show further embodiments incorporated into a washing machine, though it shall be appreciated that these embodiments are readily adaptable, based on the disclosure provided herein, to other appliance types. It shall also be appreciated that various embodiments described herein may apply to healthcare (e.g. acute care settings, point of care settings, and/or long term care setting), industrial, and/or consumer applications. Various embodiments described herein may also apply to an entire room or a commercial or residential building. Although the term "sterilize," "sterilant," "sterilization," etc. may be used in describing certain embodiments herein, it would be appreciated that such embodiments can also be used for disinfection, sanitization, and/or decontamination.

In the detailed description below, it will be understood that those parts of the disclosure that are in common between the various figures are given the same reference number in each figure, and will not be separately discussed in the detailed description of each figure.

Broadly stated, in several embodiments, the sterilization systems disclosed herein utilize a combination of broad mixture of free radicals (e.g., reactive oxygen and nitrogen species) used in sterilizing and decontamination devices to sterilize items placed in the sterilization chamber, or over which the wound chamber is placed. Various embodiments can be self-contained, small, light-weight, and portable. In some instances, some embodiments can be battery operated or powered by hand. In other examples, some embodiments can be scaled to larger volume.

Sterilization Chambers

Depending on the embodiment, the sterilization chambers for use with the systems, devices, and methods disclosed herein can vary in their dimensions and other features. Regardless, in several embodiments, the sterilization chamber is configured to receive sterilant and the item to be sterilized. Depending on the embodiment, the sterilization chamber can be stationary or movable. Whether stationary or movable, chambers can optionally be encased in a housing that also includes one or more additional components of the sterilization system (e.g., plasma generator, controller, etc.). In several embodiments, the chamber comprises a tumbler-type chamber, which, in operation, is rotated around an axis. For example, in several embodiments, the chamber is rotated about a longitudinal axis, while in additional embodiments, it is rotated around a lateral axis or a vertical axis. In still additional embodiments, the chamber can be moved about more than one axis simultaneously. Likewise, in additional embodiments, the chamber may be movable, but need not rotate in any particular passion, for example the chamber may simply oscillate, vibrate, shake, or otherwise move in a pattern of predetermined or random motions such the contents inside the sterilization chamber are likewise moved.

It shall be appreciated from the disclosure herein, the dimensions of the sterilization chamber are readily adjustable for any particular application or method of sterilizing. For example, the size and shape of the chamber can be adjusted for such embodiments wherein small medical devices are sterilized, while in other embodiments the chamber (or chambers) can be scaled up in size in order to sterilize larger items, large quantities of items, or a plurality of items to be sterilized simultaneously. Thus, the sterilization chamber provided for herein can be any geometric shape and can vary in dimension depending on the intended use of the sterilization system. With respect to dimensions, the sterilization chambers may have a volume ranging from about 50 L to about 10,000 L. For example, the sterilization chambers may have a volume ranging from about 50 L to about 100 L, about 100 L to about 250 L, about 250 L to about 500 L, about 500 L to about 1000 L, about 1000 L to about 2500 L, about 2500 L to about 5000 L, about 5000 L to about 7500 L, about 7500 L to about 10,000 L, and any chamber volume in between those listed, including endpoints.

As shall be appreciated from the disclosure provided herein, in several embodiments the sterilization chamber is an existing enclosure separate from the sterilization system, and the sterilization system is attached to, or otherwise fluidically connected with, the existing separate enclosure such that the interior of the existing separate enclosure can be exposed sterilant, thereby allowing sterilization of all of the surfaces and/or objects present within the existing separate enclosure. For example, in several embodiments the sterilization chamber is in fact a hospital room (e.g., a patient room), a storage room for equipment, or another room or enclosure that contains objects or surfaces to be sterilized.

In other embodiments, the chamber can be custom shaped to fit objects of a particular size or shape. In several embodiments, the chamber is unitary with the remainder of the system, while in some embodiments, the chamber is a separate, modular piece of the system. In several embodiments, the chamber comprises a disposable unit. In some such embodiments, a disposable chamber can be single use, while some embodiments comprise a multi-use chamber. Optionally included in such multi-use formats are indicators for the life-cycle of the chamber, for example indicating a number of cycles remaining before replacement is recommended.

As discussed in more detail below, in several embodiments, the chamber further contains an internal container of custom size and shape based on the device or devices to be sterilized, disinfected, sanitized, and/or decontaminated inside the container. In several such embodiments, the chamber comprises one or more adaptor that is integrated or attached to the container and serves as a conduit to deliver sterilant to and/or from the container. In some embodiments, a self-sealing value or material is used to ensure the objects inside the container remain disinfected or sterilized. For example, in several embodiments, a self-sealing membrane that is configured to be punctured is used. In several embodiments, a duck bill valve is used, wherein the valve is predisposed to be in a closed position.

In several embodiments, the system optionally comprises a fixed chamber (e.g. integrated or otherwise operably connected with a controller unit and/or blower/distributor—in essence, a one piece or minimal piece type system). In several embodiments employing a fixed chamber, the conduit plumbing, discussed in more detail below, is directly into and out of the chamber. Advantageously, such a chamber size provides a significant degree of volume within the sterilization/disinfection chamber vis-à-vis the overall size of the system. Additionally, such an approach, in several embodiments, provides enhanced consistency of airflow within the chamber, thereby providing for highly consistent and efficacious sterilization/disinfection of a variety of different types and shapes of devices.

In additional embodiments, the chamber is optionally removable from the remainder of the system. While several embodiments of such an approach does require additional connectors between the removable chamber and the effluent generator, or other components of the system, a removable chamber approach advantageously allows for a very compact size of the system when not in use (e.g., the chamber can be removed, stored separately, folded or otherwise compacted/disassembled). Additionally, such an approach is advantageous because a plurality of chambers of different sizes can be provided for in a single system, thereby allowing a corresponding chamber size to be used with an item to be sterilized/disinfected of a certain size. Such an approach improves overall efficiency of sterilant/disinfectant use, so that an appropriate amount of sterilant/disinfectant is provided for a device of a given size.

In several embodiments, the systems provided for herein can be mounted or utilized in a variety of different formats. For example in several embodiments the system can be a countertop unit. Alternatively, an undercounter, undercabinet, or wall mounted unit can be provided for, to enhance space savings and retain workable benchtop space in a given environment. In additional embodiments, the system can be a freestanding system, in several embodiments dimensioned to fit next to an existing countertop or cabinet. In several embodiments, such a freestanding system can be dimensioned to be relatively tall, relatively deep, and relatively narrow, thereby optimizing its ability and capacity for sterilization/disinfection while reducing its overall footprint. Depending on the embodiment, or the requirements of a given workspace, such an approach could utilize systems that are less than, equal to, or greater than a given countertop height. Systems provided for herein may also be height adjustable and/or portable (e.g. small enough to be moved from one site to another, or provided on a rolling cart or other mobile accessory). The systems disclosed herein, depending on the embodiment may be front loading, top loading, or loaded by any other approach (e.g., by sliding a container comprising items to be sterilized/disinfected into the sterilizing/disinfectant chamber). Additionally, depending on the embodiment, the systems provided for herein may be self-contained with respect to their conduit plumbing. However, in several embodiments the systems are hard-plumbed, such that the various conduits external to the system (e.g. output to the environment, air input, heater/dryer, and optionally sterilant/disinfectant source) are provided by a pre-existing infrastructure.

In several embodiments, a plurality of items are sterilized or disinfected simultaneously. While in some embodiments, this involves simply placing the plurality of items within the chamber, in additional embodiments, specialized apparatuses are used. For example, in several embodiments, there is provided a specialized apparatus for disinfecting or sterilizing the exterior of a plurality of devices while simultaneously disinfecting or sterilizing a lumen of each of the devices.

For example, in several embodiments, the sterilization/disinfection systems disclosed herein comprise an endoscope rack or manifold that sterilizes and disinfects endoscopes and similar devices, including other lumen containing devices. For example the endoscope rack can be used with scopes related to the following fields, gastroenterology, endoscopic ultrasound scopes, pulmonology, ENT (ear, nose, and throat), speech, and urology. Additionally, in some embodiments scopes with working channels such as for biopsy or suction can be used with the endoscope rack. Advantageously, in several embodiments, the endoscope unit (a term that encompasses units to sterilize/disinfect other lumen containing devices) allows the endoscopes or other devices to remain within the unit (either in a bulk section or in individual sections, and maintain sterility while inside the unit. In several embodiments, the unit may optionally further comprise an adapter configured to fluidically connect with a blower that conveys sterile or disinfected air into the working channel of the endoscope until it is dry. In several embodiments, the conveyed air is heated and/or dehumidified. In several embodiments the drying process ranges from about 5 to about 120 seconds, including about 5 to about 10 seconds, about 10 to about 20 second, about 20 to about 30 seconds, about 30 to about 60 seconds, about 60 to about 90 seconds, about 90 to about 120 second, and any time therebetween, including endpoints. In several embodiments, the systems disclosed herein comprise the dryer as a separate compartment from the chamber. However, in several embodiments, the chamber serves to store the devices during disinfection/sterilization and also during the drying process (if included). Moreover, the chamber may also serve as a storage area. In some embodiments, the endoscope or other device is placed within a separate compartment, optionally flexible, that creates a barrier between the device and the environment, such that the sterility/disinfected state will be maintained even after being removed from the chamber. Such embodiments advantageously allow the sterilized/disinfected devices to be stored and/or transported to a site of next use while maintaining the sterility/disinfected state.

In some embodiments, the chamber, including any sub-chambers or containers, are configured for continuous circulation of the effluent. In several embodiments, this includes continuous circulation through the lumen(s) of any lumen-containing devices.

The material that makes up the inner wall of the chamber can vary depending on the embodiment. In several embodiments, the chamber comprises a non-conductive, non-corrosive, or otherwise non-reactive material, such that the inner wall of the chamber does not react with the sterilant. Suitable materials include, but are not limited to, glass, plastics, polymers, metals, stainless steel (e.g., 304 or 316 stainless), ABS plastic, aluminum, bronze, carbon graphite, cast iron, ceramic (AL203), ceramic magnet, CPVC, EPDM, epoxy, Hastelloy-C®, Kel-F®, LDPE, natural rubber, NORYL®, nylon, polycarbonate, polypropylene, PPS (Ryton®), PTFE (Teflon®), PVC, PVDF (Kynar®), silicone, Titanium, Tygon®, Viton® or combinations thereof. Moreover, in several embodiments, the inner wall of the chamber may be made of a first material while other layers, including insulating or other layers may be other materials.

Effluent Generator

As discussed in greater detail below, several embodiments involve the use of a sterilant that is generated by an effluent generator. In several embodiments, the effluent generator is a sub-unit of a larger system that comprises at least one of a plasma generator (e.g., a free radical generator), a vaporizer (e.g., a unit that generates a vapor of a sterilant, such as hydrogen peroxide, a blower/distributor, and associated conduits to fluidically connect such components. In some embodiments, the effluent generator comprises all of those components, though in other embodiments only a portion of those are included in the effluent generator. In the latter embodiments, the other components may be housed elsewhere in the system or are integrated into the system externally (e.g., a system may be coupled to an existing blower at a site where sterilization/decontamination is to occur).

Plasma or Free Radical Generator

In several embodiments, the systems disclosed herein comprise a plasma or free radical supply unit. In several embodiments, a cold plasma generator such as a plasma electric free radical generator is used. In several embodiments, an ozone generator is used. In several embodiments, a dielectric barrier discharge system is used. The plasma free radical generator 30 can be any kind of dielectric barrier discharge device, electrical corona device, a glow discharge device, or a microwave generator. One non-limiting example of a device which can be used within the teachings of the disclosure is an ozone generator such as, for example, ozone generator cell SY-G20 manufactured by Longma Industrial Zone, Bao'an District, Shenzhen, 518108, P.R.C. Depending on the embodiment, any other type of system that generates free radicals may be used, for example a system or device that produces sufficient energy to break bonds, such as covalent bonds, for example through hemolytic bond cleavage. Additional embodiments, employ free radical generators that operate via silent corona discharge to split $O_2$ to create single oxygen atoms, which then interact with $O_2$ to form $O_3$ (ozone). Other embodiments employ ultraviolet radiation to split $O_2$ to create single oxygen atoms.

Vaporizer

In several embodiments, a vaporizer is included in the effluent generator. Depending on the embodiment, the vaporizer contains a liquid sterilizing agent, or a solid agent that is at least partially converted to a liquid during a sterilization cycle. In several embodiments, a liquid sterilizing agent such as hydrogen peroxide solution is used. The gas entering the vaporizer (e.g., either from an external source or recycled from the chamber), comes into contact with the solution, is vaporized (e.g., evaporation, boiling, sublimation, etc.) to produce an effluent comprising reactive oxygen species (e.g., bactericidal effluent). While certain embodiments are described with particular reference to hydrogen peroxide as the sterilizing/disinfecting agent, it will be appreciated that the system is also applicable to other solutions and/or pure liquids, such as peracetic acid, formalin solution, aldehydes such as formaldehyde, propriolactone, chlorine dioxide, and the like.

In several embodiments, the vaporizer comprises a "bubbler" or "aerator" or other "evaporator" element, in which the gas passes through a container of liquid to yield a vapor. In other embodiments, the vaporizer comprises plates or wicks that hold or are soaked with sterilant and over which the gas passes. In several embodiments, an electronic device or other motorized device (e.g., a shaker, vibration plate, or piezoelectric element) is used to assist in the vaporization of the sterilant/disinfectant. Various configurations of vaporizers can be employed, depending on the embodiment. FIGS. 1B-1D, described in more detail below, depict various embodiments of evaporator elements that are employed in certain embodiments of the vaporizer. For example, in several embodiments, the evaporator comprises a plurality of tubes with a wicking material disposed between the tubes. In several embodiments, a portion of the wick rests in a pool of sterilant/disinfectant. In several embodiments, there is a float element (optionally coupled to a sensor) that regulates the amount of sterilant/disinfectant in the pool at a given time. The sterilant/disinfectant is wicked up the wicking element and gas is passed across the wicking element or bubbled through the wicking element to yield evaporation, misting, and generally formation of a sterilant/disinfectant vapor. In several embodiments, the wicking material is baffled in order to enhance the surface area of the wick and increase the efficiency of sterilant/disinfectant vapor formation. In several embodiments, interwoven layers of wicking material are used, for example a first layer or layers in contact with the sterilant/disinfectant pool that are interwoven with a second layer or layer not in contact with the sterilant/disinfectant, wherein the interwoven section allows transfer of sterilant/disinfectant wicked into the first layer to the second layer. Depending on the embodiment, evaporation/vaporization can optionally occur passively (e.g., without heat) by the flow of air through the wet wicking material, though in several embodiments a heating source is used.

In several embodiments, the sterilant is provided in a quantity sufficient for a single sterilization/decontamination cycle. However, in several embodiments, a multi-run cartridge or container of sterilant is provided. In some embodiments, the sterilant (e.g., hydrogen peroxide) concentration can be from about 30% to about 60% concentration, e.g., about 30%, about 35%, about 40%, about 45%, about 50%, about 55%, or about 60% concentration. In some examples, the hydrogen peroxide vapor concentration can be from about 100 ppm to about 10,000 ppm or any ranges in between such as about 100 ppm to about 600 ppm, about 500 ppm to about 2500 ppm, about 1000 ppm to about 4000 ppm, about 1500 ppm to about 5000 ppm, about 2500 ppm to about 6000 ppm. At the end of the sterilization cycle, the final hydrogen peroxide vapor concentration can be about 600 ppm or less (e.g., about 550 ppm or less, about 525 ppm or less, about 500 ppm or less, about 475 ppm or less, about 450 ppm or less, about 425 ppm or less, or about 400 ppm or less) in some embodiments. In several embodiments, the vaporizer is dried or otherwise treated upon exhaustion of the sterilant.

Blower

In several embodiments, a blower or air distribution unit is used to convey gases through the plasma generator and/or vaporizer. In several embodiments, this unit also provides sufficient motive force to push the sterilant/disinfectant effluent into the sterilization chamber. Depending on the embodiment, the blower/flow generator comprises a pump, such as a circulating pump, a positive displacement pump, or an air conveyor, a fan, or a blower optionally integrated with a flow distributor. In embodiments comprising a flow distributor, the distributor is configured to convey a desired percentage of air/sterilant to either the plasma generator or vaporizer (e.g., the blower can be a controllable-speed blower, though optionally in several embodiments, the blower is a single-speed blower). As discussed in more detail below, the ratio of air/sterilant conveyed to the plasma generator and vaporizer is variable, depending on the embodiment. In several embodiments, the variation in flow is fixed prior to a sterilization/decontamination cycle. In additional embodiments, the variation in flow is dynamic during a cycle, for example, adjusting the flow between the plasma generator and the vaporizer depending on the amount of free radicals or hydrogen peroxide vapor being recycled from the chamber.

In several embodiments, the blower with the flow distributor recycles effluent from the chamber (e.g., via one or more conduits) and distributes it into the plasma generator and/or vaporizer. In several embodiments, a filter (or filters) is used in-line between the blower and the plasma generator and/or vaporizer. Distribution can vary with each cycle, or within a cycle. For example, in several embodiments, effluent that is recycled is sent 30:70 to the plasma generator and vaporizer, respectively. Other proportions are used, in several embodiments, such as 10:90, 20:80, 40:60, 50:50, 60:40, 70:30, 80:20, 90:10 or any distribution therebetween. In several embodiments, the recycling advantageous allows for the optimized use of the sterilant/free radicals in the effluent, replacing or rejuvenating the required component only when needed. In several embodiments, sensors in the chamber, the conduit, the blower or other location are used to sense the amount of free radical and/or sterilant and report the amount or concentration to a controller module, which thereafter signals the blower/distributor to adjust flow accordingly. Moreover, in several embodiments, this approach allows the system to reach an optimal concentration of sterilant in a reduced amount of time, thereby decreasing cycle times.

Conduits for Gaseous Communication

Also provided for herein in several embodiments are a series of conduits that are configured to convey gases and/or sterilant/disinfectant between the various components of the sterilizing/disinfecting systems. For example, in several embodiments, there is at least one conduit within the effluent generator that carries gas (which may comprise recycled sterilant/disinfectant) from the blower/distributor to the plasma generator and/or the vaporizer. The number of conduits depends, at least in part in some embodiments, on the configuration of the components of the effluent generator. For example, a single conduit may be used in embodiments wherein the plasma generator and the vaporizer are in series. In other embodiments where the plasma generator and vaporizer are in parallel, multiple conduits may be used. Likewise, depending on the embodiment, the number of exiting the plasma generator and/or the vaporizer is dependent, at least in part, on whether these components are in series or in parallel.

As with the chamber materials described above, in several embodiments, the conduit(s) comprises a non-conductive, non-corrosive, or otherwise non-reactive material, such that the conduit(s) does not react with the steriliant/disinfectant. Suitable materials include, but are not limited to, glass, plastics, polymers, metals, stainless steel (e.g., 304 or 316 stainless), ABS plastic, aluminum, bronze, carbon graphite, cast iron, ceramic (AL203), ceramic magnet, CPVC, EPDM, epoxy, Hastelloy-C®, Kel-F®, LDPE, natural rubber, NORYL®, nylon, polycarbonate, polypropylene, PPS (Ryton®), PTFE (Teflon®), PVC, PVDF (Kynar®), silicone, Titanium, Tygon®, Viton® or combinations thereof.

In several embodiments, the conduit(s) comprise one or more filters that function to eliminate particulate or other matter from an incoming and/or recirculating gas stream within the sterilization/disinfection system. A variety of filter types can be used, depending on the embodiment. For example, in several embodiments, a HEPA filter is used. In some embodiments, ionic filters, carbon filters, UV filters, cellulose filters, silica based filters or the like are used, either alone or in combination.

In addition to conduit to conduct gases through the system components, several embodiments one or more valves are used to regulate flow through the system. For example, the sterilization/disinfection system may comprise one or more pressure valves that regulate flow into/out of the chamber (or other components of the system). Depending on the embodiment, valves that are open to the environment may also be present. For example, in one embodiment, a valve to the environment is configured to open and allow environmental air to pass into an optional heater and/or filter, and then pass into the chamber at the start of a sterilization/disinfection cycle, in order to pre-heat and/or dry the chamber. In additional embodiments, the system may also valve that regulates flow through a conduit that runs from the chamber to the external environment and serves to vent the chamber to the environment at the end of a sterilization/disinfection cycle. In several embodiments, the valve is preceded by one or more of a filter (e.g., a HEPA filter) and a free radical destroyer. In such embodiments, the exit conduit is configured to deactivate/destroy any remaining sterilant/disinfectant effluent prior to it exiting the system to the environment. In several embodiments, valves of the system are independent of a control system and self-regulating (e.g., operating based on a pressure, temperature or other type of threshold), while in other embodiments, the valve(s) are regulated by a controller unit.

Controller

In some embodiments there is a controller unit that interacts with and/or controls or regulates the operation of one or more of the plasma generator, the evaporator, the hydrogen peroxide cartridge, blowers/fans, valves (if any) as well as the electronics and control boards for the system. In some embodiments, the controller unit is dimensioned to be wall or counter mounted. In several embodiments, the controller is integral with, or contained within the effluent generator or the chamber. In some embodiments, the control unit receives information, either from a user or automatically (such as by an identifier on an object to be sterilized/disinfected or a carrier for such object) that is used to determine an appropriate sterilization cycle (e.g., time, concentration of sterilant/disinfectant, pressure change, humidity control, etc.). As discussed in more detail below, the controller comprises one or more special-purpose computing devices that is hard-wired or programmed to regulate the operation of the sterilization/disinfection system.

Heater/Dryer

As discussed herein, in several embodiments, the sterilizing/disinfecting system includes at least one heater and/or dryer. By way of example, a dryer may be a desiccant dryer or a dehumidifier utilizing a refrigeration system. Depending on the embodiment, a heater may be used to preheat the conduits and/or the chamber in order to provide for a dry and warmed environment into which items to be sterilized/disinfected are introduced (e.g., the chamber). In several embodiments, this approach reduces and/or eliminates condensation that could form in or on an item that is sterilized/disinfected, which could provide a potential future source or site of contamination, for example during storage of the item until next use. See, for example FIGS. 1F and 1G that illustrate additional non-limiting examples of embodiments configured to help maintain desired vapor saturation levels to reduce or avoid undesired condensation. As discussed above, in several embodiments, the controller interacts with and regulates the dryer and/or heater to maintain desired humidity levels in the chamber and thereby avoid undesired condensation.

Sensors

As mentioned briefly above, in several embodiments, one or more sensors are used to monitor various aspects of the components and/or performance of the sterilization/disinfection systems. For example, sensors may be used to monitor and/or regulate the amount of sterilant/disinfectant that is moved into the chamber, the concentration of sterilant/disinfectant in the chamber at a given point (or points) in the cycle, control or regulate destruction/release of sterilant/disinfectant from the chamber to the atmosphere, control or regulate recycling of sterilant/disinfectant to the effluent generator, control or regulate distribution of gas flow (which may include recycled sterilant/disinfectant) between the plasma generator and the vaporizer, as well as a variety of other parameters, including but not limited to temperature, pressure, humidity, cycle duration, etc. It shall be appreciated that such sensors can be used in any component of the system individually, or can be used to monitor the system as a whole (e.g., providing a plurality of types of data to the controller, which integrates the data and adjusts the system as needed).

Accessories

Indicators

A variety of accessories are provided for herein that are operatively interactive with the sterilizing/disinfecting systems disclosed here. For example, quality control and/or regulatory compliance indicators (e.g., disposable after every cycle, semi-disposable for use after a number of cycles, or non-disposable) may be incorporated in many embodiments. Such indicators may include chemical indicators (e.g., those that visually confirm that the indicator (which is to be placed in the chamber or in a package or carrier for a device to be sterilized/disinfected) has been exposed to a selected degree (e.g., amount/concentration) of sterilant/disinfectant to achieve the desired effect. Biological indicators may also be used, such as a positive control strip or container that comprises a known quantity of a type of biological organism that is desirably eliminated by the sterilization/disinfection system. This indicator can demonstrate visually (or otherwise) that the biological organisms have been rendered inert or killed by the sterilization/disinfection process. The indicators can optionally be used directly in the chamber, affixed to an item to be sterilized/disinfected, or in a container or vessel that contains an item to be sterilized/disinfected. In several embodiments automated or electronic sensors are used. Thus, in several embodiments, such chemical and/or biological indicators have a quality control function that ensures that a given sterilization/disinfection cycle has run to a required degree of efficacy.

Residual Coating Apparatus

In several embodiments, there is also provided an additional apparatus, or component of the system, that comprises a residual coating deposition device, wherein such a device functions to deposit a residual coating on an item or items in the chamber. In several embodiments, the residual coating that is bactericidal and may optionally be sacrificial in nature (e.g., removable after potential contamination). In several embodiments, the residual coating material has bactericidal properties such as silver, copper, or a combination of bactericidal materials. In several embodiments, the residual coating is biocompatible with human subjects and is preferably used on items that come into contact with patients or other persons (e.g., surgical tools, endoscopes, dental products, infant care products, etc.). Prior to deposition the residual coating material may be in the form of a gas, a liquid, a solid agent that is converted into a liquid during the coating cycle, or other suitable material.

Item Containers

In several embodiments, as discussed in more detail herein, various custom containers are provided for. In several embodiments, the containers are custom sized for an item (or items) to be sterilized/disinfected. In several embodiments, the containers provide a customized insert or relief to house the item (items), for example to protect the item from impact or other forces that could damage the item. In some embodiments, the containers are hard shell or otherwise rigid. In additional embodiments, the containers are flexible and configured to conform to the general shape of the item. In still additional embodiments, the containers are flexible, but provided in a "sized to fit" format. In some embodiments, the containers are configured to be stackable, able to be hung, or otherwise configured for easy and compact storage. As discussed herein, in several embodiments, the containers are configured to allow the item to be stored within the container until its next use, thereby maintaining the sterile/disinfected item and surrounding environment. In several embodiments, the containers are configured to allow sterilization/disinfection of items comprising a lumen (or lumens). In several embodiments, the container is configured to provide a sterilant/disinfectant not only the exterior surfaces of the item, but also to internal lumens. In several embodiments, the containers comprises a dedicated inlet/outlet for sterilizing/disinfecting the external surfaces of the item, and a second (or more) dedicated inlet/outlet for sterilizing/disinfecting the internal, luminal surfaces of the item. In several embodiments, customized containers are particularly useful because they allow sterilization/disinfection of large (e.g. long) items that using other approaches would require the items to be stretched out to all or substantially all of their longitudinal links. In contrast, the custom containers provided for in several embodiments allow a large item to be sterilized/disinfected in a compact footprint, thereby reducing the surface area/volume of space required for a system to accomplish that sterilization, reducing waste (e.g. excessively large packaging) and facilitating storage of sterilized/disinfected items until their next use, even when storage space may be limited. In several embodiments, the container comprises an identifier that enables the user of the system to determine and initiate a sterilization/disinfection cycle that is optimal for the item to be sterilized/disinfected.

Organizational Units and System Carriers/Carts

In several embodiments, the systems and devices disclosed herein also optionally comprise one or more organizational unit in order is system carrier or cart. In several embodiments for example, the system further comprises one or more trays, drawers, or dividers that are configured to carry, house, or otherwise store various accessories routinely used with the system. For example in several embodiments the system may further comprise an organizational unit that houses a plurality of different types of sterilization/disinfection indicators, such as the indicator strips discussed above. In additional embodiments, the system may comprise one or more accessory units that are configured to assist in integrating the sterilization/disinfection system into the environment in which it is used. For example, considerations that may impact the ultimate footprint, and design of the a system for a given use include, but are not limited to the available space for the units in a certain environment, the available space for storage of consumables (such as hydrogen peroxide cartridges, sterilization/disinfection containers, and storage of sterilized/disinfected items). Workflow, either current or anticipated, is also a consideration in determining a configuration of the sterilization/disinfection system for a certain environment of use. Additionally, the safety of users and/or patients is an additional consideration. The systems, devices, and methods disclosed herein are amenable to use in a variety of settings, including point-of-care locations, acute care settings, long-term care settings, or other commercial environments (production or processing plants, large healthcare facilities, medical waste facilities and the like).

Implementation Parameters

As discussed in more detail below, the systems, devices, and methods disclosed herein enable the user to disinfect (either high-level or low level disinfection, depending on the device) and/or sterilize certain items, such as medical devices, electronic devices, surfaces, processing equipment, foodstuff, and wounds). Certain implementation procedures are described generally below with additional detail provided elsewhere in the present disclosure. It shall be appreciated that these implementation mechanisms are readily combinable, and variable, to adjust for a particular item, surface, or wound to be treated in an effective fashion (e.g. tailored amount of sterilant/disinfectant, tailored time, tailored pressure, etc.) and that they can be readily combined by one of ordinary skill in the art, based on the disclosure provided herein to achieve efficacious sterilization/disinfection.

According to several embodiments, the disclosed devices, systems, and methods, are configured to reduce bioburden on an object or surface (e.g., the number of bacteria or other microorganism, fungus, etc. on a surface that has not been sterilized). In some examples, bioburden testing, also known as microbial limit testing, can be used in products or components used in the pharmaceutical or medical field to evaluate microbial levels during processing and handling or after a sterilization/disinfection cycle.

Bioburden can be a significant source of morbidity or mortality. For example, hospitalized patients (e.g. patients in an intensive care unit) may be fitted with devices for insertion into the body. As an example, a hospitalized patient can be fitted with endotracheal tubes to facilitate respiration. Such an endotracheal tube may remain in place within a patient for an extended period of time (e.g. up to 14 days). Biofilm contamination of endotracheal tubes within an intubated patient can lead to an increased rate of infection (e.g. pneumonia).

In other examples, occurrences of catheter related blood stream infection can increase as a result of the use of invasive medical devices including intravascular catheters. Such infections are one of the most common types of bloodstream infection. Several factors relating to the pathogenesis of catheter related blood stream infection have been identified. For example, the skin and hub are the most common sources of colonization of percutaneous vascular catheters. The organisms can migrate from the skin to the insertion site along the intercutaneous segment, eventually reaching the intravascular segment of the tip. As well, the hub can be a major source of colonization of the catheter lumen, which leads to bloodstream infections through luminal colonization of the intravascular segment. The catheter surface can be another factor relating to the pathogenesis of catheter related blood stream infection. Organisms that adhere to the catheter surface can maintain themselves by producing an "extracellular slime," a substance rich in exopolysaccharides, often referred to as fibrous glycocalyx or microbial biofilm. Microorganisms can bind to the surface of host proteins, such as fibrin and fibronectin, to produce biofilm.

In other examples, the prevention of colonization of bacterial and fungal organisms on the surfaces of orthopedic implants has frequently required the use of antimicrobial agents, such as antibiotics, bound to the surface of such devices. The goal of such attempts has been to produce a sufficient bacteriostatic or bactericidal action to prevent colonization. Various methods have previously been employed to coat the surfaces of medical devices with an antibiotic.

As will be discussed in more detail below, the disclosed devices, systems, and methods can be configured to reduce the bioburden of medical devices through sterilization. In addition to the use on medical devices, the disclosed devices, systems, and methods can be used to reduce the presence of bacteria and fungal organisms in other settings that require sterilization. For example, this can include, but not be limited to, hospital settings, settings where food is processed, prepared, or served, settings where individuals with a compromised or decreased immune system live or have access to, environments with a high rate of bacteria buildup (e.g. bathrooms, daycare centers, public transportation, etc.).

Sterilant/Disinfectant

In several embodiments, a liquid sterilizing/disinfecting agent, or a solid agent that is at least partially converted to a liquid during a sterilization/disinfection cycle is used. In several embodiments, a liquid sterilizing/disinfecting agent such as hydrogen peroxide solution is used. In several embodiments described herein are done so with particular reference to hydrogen peroxide as the sterilizing/disinfecting agent, it will be appreciated that the system is also applicable to other solutions and/or pure liquids, such as peracetic acid, formalin solution, aldehydes such as formaldehyde, propriolactone, chlorine dioxide, and the like.

As discussed in more detail below, in several embodiments, varied concentrations of the sterilizing/disinfecting agent are provided, with different amounts being utilized, depending on the type of sterilization/decontamination cycle. Concentrations can range, in several embodiments, from about 30% to about 60% concentration, e.g., about 30%, about 35%, about 40%, about 45%, about 50%, about 55%, or about 60% concentration. In some examples, the hydrogen peroxide (or other agent) vapor concentration can be from about 100 ppm to about 10,000 ppm or any ranges in between such as about 100 ppm to about 600 ppm, about 500 ppm to about 2500 ppm, about 1000 ppm to about 4000 ppm, about 1500 ppm to about 5000 ppm, about 2500 ppm to about 6000 ppm.

Operating Pressures

In some embodiments, the vapor pressure of the sterilant/disinfectant is maintained at or below the saturation level in the sterilization chamber (e.g., for the pressure and/or temperature inside of chamber). In several embodiments, this approach reduces or eliminates condensation buildup on the items being sterilized, on the walls of the chamber, and on other components exposed to the sterilant/disinfectant, such as hoses and fittings described herein.

In some embodiments, the disclosed devices, systems, and methods can be operated at an ambient pressure, e.g., a pressure approximately equivalent to the atmospheric pressure in a given location (e.g., sea level vs. mountain). Depending on the embodiment, the pressures employed in the systems and devices disclosed herein range from about 600 mm mercury (mm Hg) to about 800 mm Hg, including about 600 to about 610, about 610 to about 620, about 620 to about 630, about 630 to about 640, about 640 to about 650 about 650 to about 660, about 660 to about 670 about 670 to about 680, about 680 to about 690, about 690 to about 700, about 700 to about 710, about 710 to about 720, about 720 to about 730, about 730 to about 740, about 740 to about 750, about 750 to about 760, about 760 to about 770, about 770 to about 780, about 780 to about 790, about 790 to about 800, and any pressure therebetween, including endpoints. In some embodiments, the ambient pressure can be pre-programmed and/or adjustable by a user. This can allow the disclosed device, system, and method to be adaptable for a variety of different items to be sterilized. Moreover, in several embodiments, the relatively ambient pressure can be adjusted as needed to further reduce the potential for condensation formation within the chamber and/or on/in devices to be sterilized/disinfected. Additionally, while various embodiments can be utilized in approximate room pressures, in some instances, varying the speeds of blowers/distributors, conduit size/valve position, allows for use of slight negative or positive pressure. In some embodiments, a slight negative pressure may advantageously keep the effluent within the system as a safety precaution. In some embodiments, the pressure may be approximately 1 to 2 cm of $H_2O$ lower than ambient pressure.

Open and Closed Systems

In some embodiments, the disclosed devices, systems, and methods operate in a closed loop. In a closed loop system, the system does not rely on matter exchange external to the system. As such, in a closed loop sterilization system, sterilization/disinfection vapors can be recirculated. In several embodiments, this increases the efficiency of the system as the recycled vapors still provide potential sterilization/disinfection effects.

For example, as discussed herein, in a closed loop system, a carrier gas, such as air, is dried and heated prior to flowing past a vaporizer. A hydrogen peroxide aqueous solution can be introduced into the vaporizer and enables the solution to be vaporized. The resulting vapor is then combined with the carrier gas and introduced into a sterilization chamber of varying size, shape, and material. A blower can exhaust the carrier gas from the sterilization chamber and recirculate the carrier gas to the vaporizer where additional vaporized hydrogen peroxide is added.

In addition to the closed loop system, an open loop system is also provided in several embodiments, to provide free air venting. In an open loop system, the system is configured to allow gases to be vented into the external environment. For example, in an open loop system, various portions of the system can be vented before, after, or during sterilization. In some embodiments, before sterilization is conducted in the sterilant chamber, all gases can be purged and the gaseous contents of the chamber are purged to the environment.

As well, in an open loop system, various portions of the system can be configured to allow air to enter the system. In some embodiments, the open loop system can include inlets to allow independent entrance into the system. For example, each of the inlets can comprise one or more valves that provide for selective flow of air into the open loop system. In some embodiments, the open loop system can include a filter element that filters environmental air and allow it to pass into the system.

In one embodiment, an open loop system is for the purpose of pre-heating (optionally) and drying the chamber 10 before and after the circulation of bactericidal effluent through the closed loop system. The open loop system uses a flow generator (e.g., an exhaust pump, an air conveyor, a fan, or a blower), exhausting to atmosphere to draw air from an air input through an input (and an optional heater). The input air may optionally be filtered by filter In one embodiment of open-loop operation, the output of the chamber is drawn out by a blower and passes through a conduit and a free radical destroyer. In several embodiments, the open loop approach is implemented initially, such that the chamber, and items within the chamber, can be dried and pre-heated before implementing closed loop operation. Likewise, after sterilization/disinfection, an open loop operation can be reinstated, depending on the embodiment.

Humidity

In several embodiments, moisture control/humidity regulation (e.g., self-regulation or control) is important to reduce or avoid unwanted condensation. Without control, in some contexts, moisture deposition can cause adverse effects on the articles being sterilized/disinfected. As one example, when electronic devices are being sterilized, excessive condensation could potentially create electrical shorts and otherwise damage the electronic devices. Similarly, residual condensation on a device can reduce the efficacy of sterilization/disinfection, or provide a "safe harbor" for future growth of microorganisms or mold during storage.

In some embodiments, a desiccant or other chemical composition that is designed to absorb moisture is provided for use in conjunction with the system. In some embodiments, the desiccant is provided within the conduits leading into, or exiting, a sterilization/disinfection chamber. In such embodiments the desiccant functions analogously to a filter for particulate matter, however serves to remove moisture from the gases entering or exiting the sterilization/disinfection chamber. In additional embodiments a desiccant reservoir is provided within the sterilization chamber to aid in controlling the relative moisture content within the chamber before, during, or after a sterilization/disinfection cycle. In several embodiments, a target humidity level is recommended for a given type of device to be sterilized/disinfected or the degree to which a device, or surface, is to be sterilized are disinfected. In several embodiments the target relative humidity range is between about 10% to about 50% including about 10% to about 15%, about 15% to about 20%, about 20% to about 25%, about 25% to about 30%, about 30% to about 35%, about 35% to about 40%, about 40% to about 45%, about 45% to about 50%, and any relative humidity between those listed, including endpoints. In additional embodiments greater degrees of humidity can be provided for within the sterilization chamber, in combination with a heating and/or drying cycle within the sterilization/disinfection protocol.

Temperature

As described herein, various embodiments may be operated at ambient conditions (e.g., room temperature). However, some embodiments allow for controlled or automatic regulation of the temperature in the chamber. In several embodiments, lower ambient temperatures slow the sterilization process, which may be advantageous in several embodiments. Likewise, in several embodiments, a higher ambient temperature accelerates the process. Therefore, depending on the embodiment, temperatures can range from about 50° F. to about 120° F., including about 50 to about 60° F., about 60 to about 70° F., about 70 to about 80° F., about 80 to about 90° F., about 90 to about 100° F., about 100° F. to about 110° F., about 110° F. to about 120° F. It shall likewise be appreciated that temperatures can vary depending on the device, object, or surface (including the wound) to be sterilized/disinfected in order to provide an optimal balance of efficacy of sterilization/disinfection versus the possibility for damage to an object (e.g. electronic devices) or pain to a subject (a patient with a wound).

Activation/Cycle Time

Depending on the embodiment, the systems and devices disclosed herein can be programmed to run various types of cycles. For example, cycles designed for sterilization, high level disinfection, or low level disinfection may vary in duration—e.g., sterilization having a longer cycle time as compared to high level disinfection, which has a longer cycle time than low level disinfection. In several embodiments, the systems provided for herein also are configured to run a maintenance cycle, for example a short cycle during an extended storage. For devices that have previously been subject to sterilization/disinfection.

In some embodiments, the disclosed devices, systems, and methods can be configured to include a programmable activation time. In some examples, the activation time can be customizable and/or controlled by a user. This can allow the disclosed devices, systems, and methods to be configurable to different types of devices to be sterilized. As well, depending on the item to be sterilized, activation time can be adjusted to allow for more thorough processing.

It shall be appreciated that cycle times are readily adjustable by a given user for a given context, but generally speaking can vary between about 60 seconds and about 20 minutes, including about 60 seconds to about 90 seconds, about 90 seconds to about 120 seconds, about two minutes to about four minutes, about four minutes to about six minutes, about six minutes to about eight minutes, about eight minutes to about 10 minutes, about 10 minutes to about 15 minutes, about 15 minutes to about 20 minutes, about 20 minutes to about 30 minutes, and any time between those listed, including endpoints. Additionally, multiple cycles, or repeats, can be run on any given device or surface to be sterilized/disinfected, should additional sterilization disinfection be required Unit Level Sterilization In some embodiments, the disclosed devices, systems, and methods can be configured to provide sterilization to a plurality of individual units. For example, the system can include structures to allow for sterilization of individual and/or separate components of an item. In some embodiments, the disclosed devices, systems, and methods, can allow for the sterilization of small or hard-to-reach areas such as lumens, folds, crevices, etc. A unit level sterilization can provide for more thorough sterilization as well as lower costs.

Residue Free

In some embodiments, the disclosed devices, systems, and methods provide a sterilization/disinfection method that is residue free (also disclosed elsewhere herein are embodiments wherein a layer is deposited purposefully). In several embodiments, a residue free sterilant/disinfectant is configured to eliminate the risk of carry-over of chemical residue to patients and also to reduce the cost of chemical disposal. In some embodiments, residue free sterilant/disinfectant also ensures that no separate water rinse or post-cleaning step is required to remove excess sterilant/disinfectant from the item or surface being treated.

In addition to removing remaining sterilant chemical from the item being sterilized, the disclosed devices, systems, and methods can also ensure that the item being sterilized will dry to a clean, bright, shiny appearance with no spotting, streaking, or film residue. This can save significant time any money and can improve the appearance of the sterilized item.

Setting/Application

All of the disclosed devices, systems, and methods to provide sterilization can be used in acute care, point of care, long term care, or commercial settings. As well, the disclosed devices, systems, and methods can be used to prevent and control infection. In some embodiments, the disclosed devices, systems, and methods are configured to sterilize and/or disinfect instruments and devices. In some examples, the disclosed are configured to provide systems and methods for general sterilization and disinfection.

Sterilization Chamber with Both Plasma and Vapor.

Figure 1B:
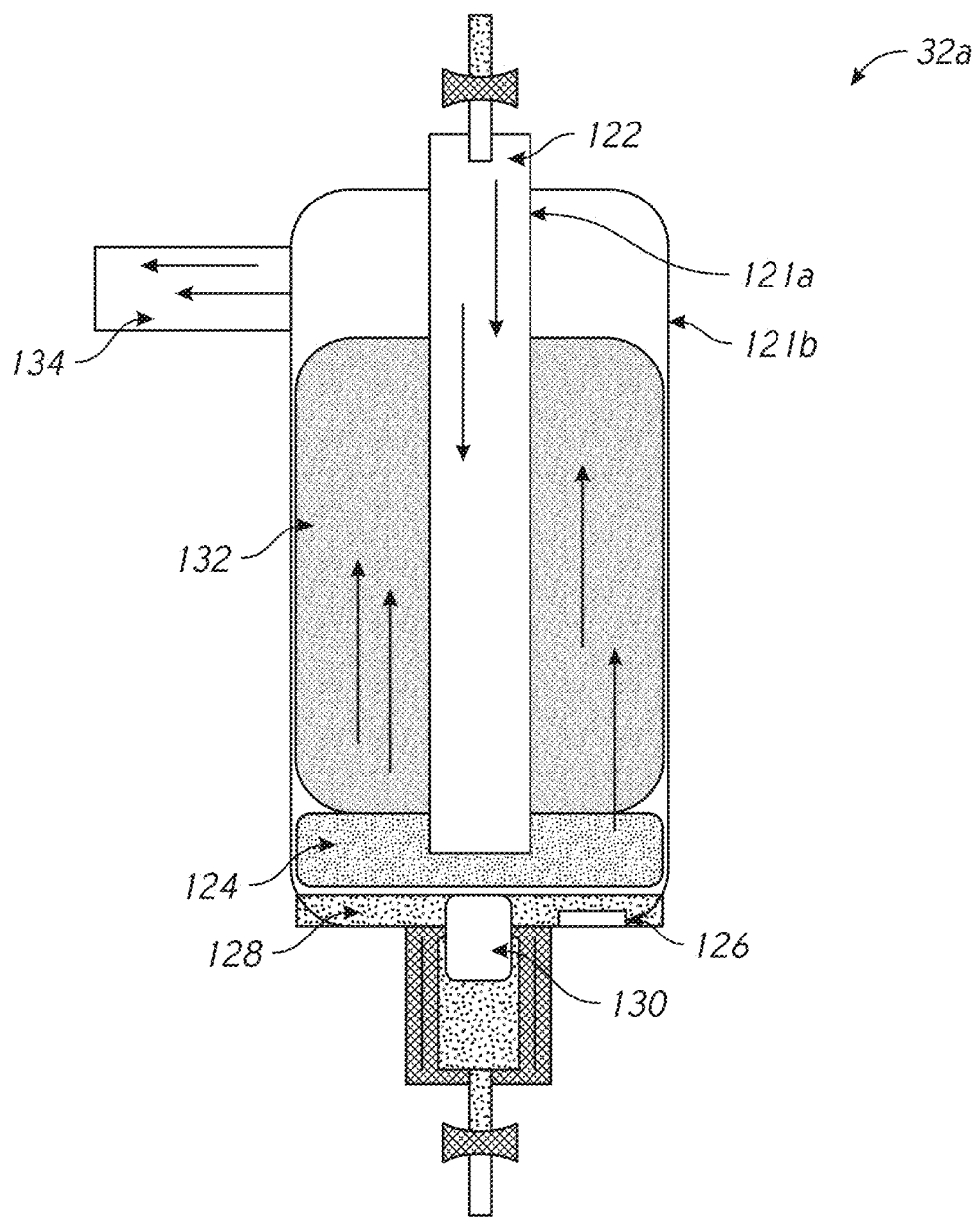
FIG. 1B shows an example evaporator configured to generate sterilant at vapor pressures at or below saturation levels and that may use a piezoelectric transducer to create a sterilant mist.
Figure 1C:
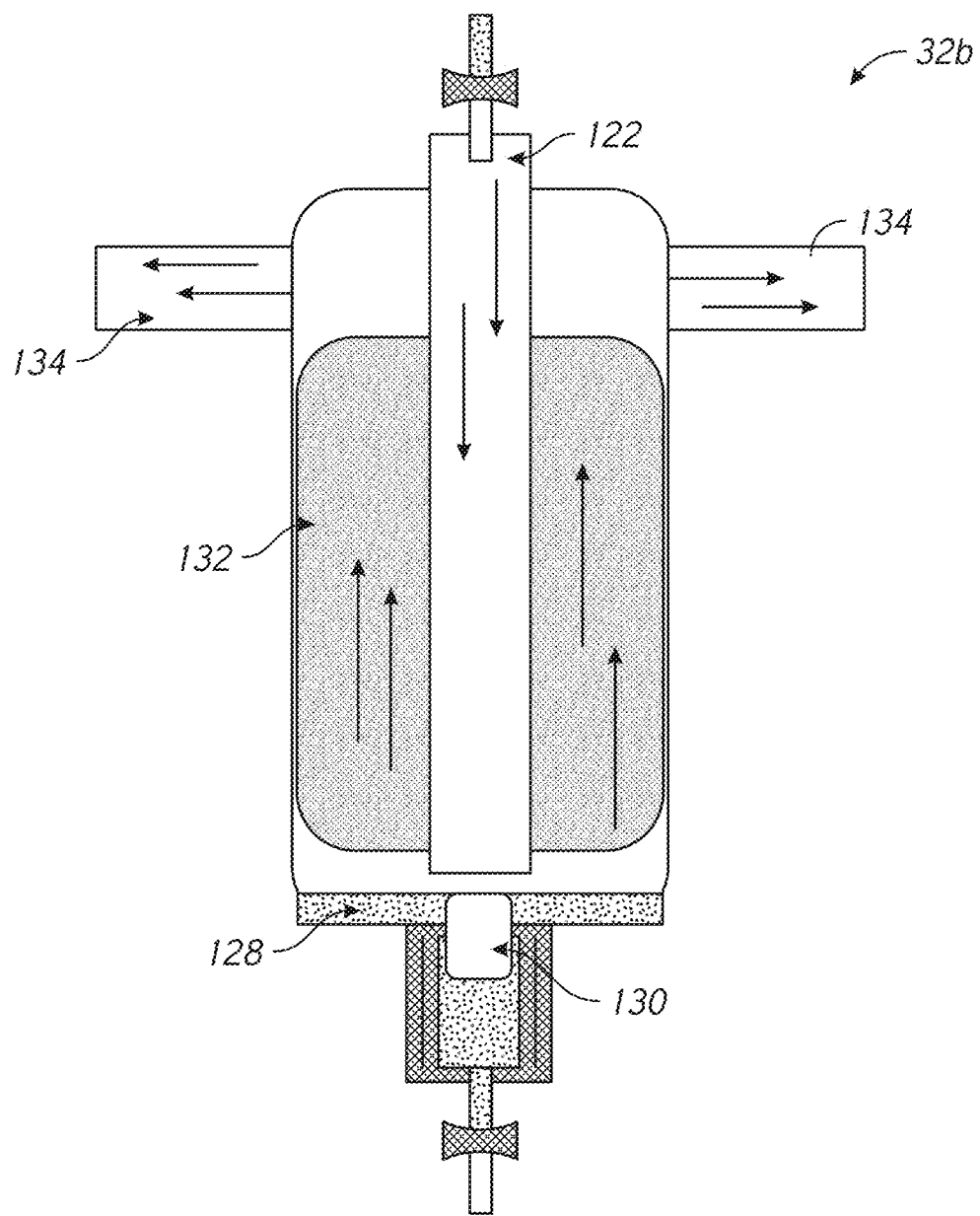
FIG. 1C shows an example evaporator configured to generate sterilant at vapor pressures at or below saturation levels and that may omit the piezoelectric transducer.
Figure 1D:
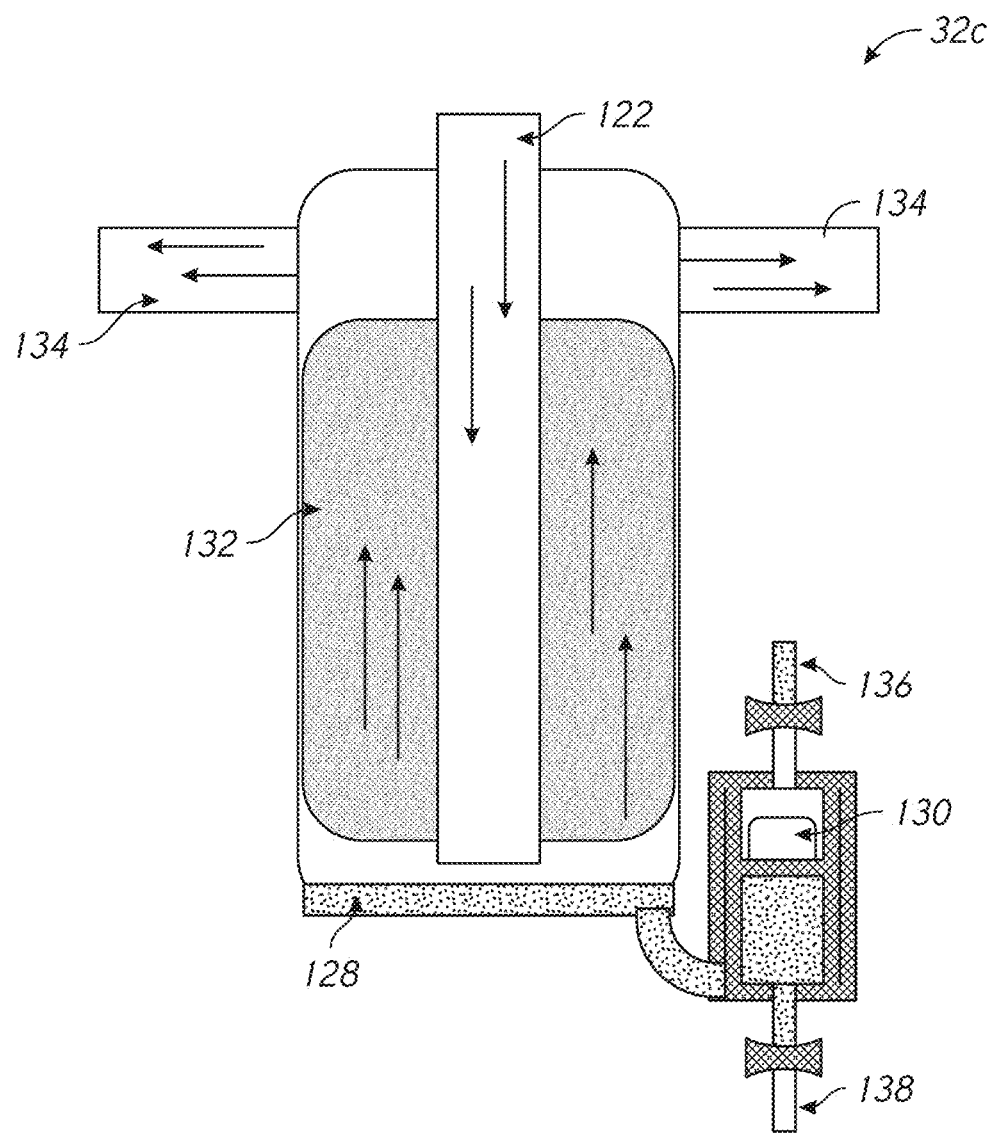
FIG. 1D shows an example evaporator configured to generate sterilant at vapor pressures at or below saturation levels and that may include a drain for removing sterilizing agent.

As shown in FIG. 1A, various embodiments include a sterilization chamber 10 configured to receive sterilant and the item to be sterilized. The sterilization chamber 10 can include any type of moving or stationary chamber, non-limiting examples of which are described herein. In FIG. 1A, the chamber 10 is shown as a tumbler-type chamber, which is rotated around a longitudinal axis 54 (e.g., rotate around the x-axis), for example by motor 51, in the manner of a conventional home clothes dryer. Items to be sterilized are placed in a chamber 10. Such a tumbler-type chamber 10 would be appropriate for fabric items 56 such as towels and cloths, surgical masks and gowns, gloves, etc. The tumbler design could also be used to sterilize shredded medical waste within the teachings of the disclosure.

In some embodiments, the chamber 10 may rotate around the longitudinal axis 54 in a clockwise direction, a counter clockwise direction, or alternating between clockwise and counter clockwise directions. In some embodiments, the chamber 10 may alternate between partial rotations about the longitudinal axis 54 in one direction and partial rotations about the longitudinal axis 54 in the opposite direction. In some other embodiments, the chamber 10 may alternate between partial and complete rotations about the longitudinal axis 54.

The chamber 10 is not limited to rotations about the longitudinal axis 54, but may move in other degrees of freedom. For example, in some embodiments, the chamber 10 may rotate partially or completely about a different longitudinal axis, such as one perpendicular to longitudinal axis 54 (e.g., rotate about the y-axis or the z-axis). As another example, the chamber 10 may move back and forth along a direction parallel the longitudinal axis 54 (e.g., along the x-axis) or a different longitudinal axis (e.g., along the y-axis or the z-axis). The chamber 10 may also move in a combination of the different degrees of freedom. For example, the chamber may be a shaker, agitator, or other type of device that moves in randomized or oscillating patterns.

The chamber 10 may be made of any type of material, yet in various embodiments, the chamber 10 is made of a non-conductive material to not interfere with certain reactive species of the sterilant. For example, the chamber 10 may be made of glass, plastic (e.g., polytetrafluoroethylene), or combinations thereof (e.g., partially glass and partially plastic). In some embodiments, the chamber 10 may be transparent or partially transparent such that the contents within the chamber 10 may be viewable during the sterilization process.

The size and shape of the chamber 10 are not particularly limited, but can be tailored to the application of use. For example, in some instances, the chamber 10 may be relatively small, light-weight, and portable. In other embodiments, the chamber may be dimensioned to accommodate larger items, such as control modules for IV stands, power units for various equipment in surgical suites, end piece apparatuses used in an operating room (such as eyepieces for surgical scopes). In some embodiments, inside chamber 10 there is a container of custom size and shape based on the device or devices to be placed inside the container for sterilization, disinfection, sanitation, and/or decontamination. In other embodiments the chamber 10 can be entire room, for example an Operating Room, where the sterilant source can be placed inside or outside the room.

In some embodiments, chamber 10 further contains a container of custom size and shape based on the device or devices to be sterilized, disinfected, sanitized, and/or decontaminated inside the container. In some embodiments, the custom sized container inside chamber 10 contains only one device and the container is custom sized to fit that individual device. In some embodiments, the container inside chamber 10 contains a set of devices and the container contains recesses shaped to hold each individual device. In embodiments where chamber 10 further includes a custom sized container, an adaptor attaches to the container and delivers sterilant to the container. In some embodiments the sterilization cycle for the device is decreased due to the direct, individualized exposure to the sterilant within the custom sized container. In some embodiments, a duck bill valve forms the attachment point between the adaptor and the container. In such embodiments, the valve is predisposed to be in a closed position such that the attachment and removal of the adapter does not allow air flow to disturb the sterility of the contents inside the container. Furthermore, in such embodiments the cracking pressure of the duck bill valve is high enough to prevent air flow in or out of the container. Additionally, in such embodiments, the airtight nature of the container is further maintained by a seal on the edges of the container. The custom sized container placed inside chamber 10 allows for more direct exposure of sterilant.

In some embodiments, a set of devices will be placed in the custom sized container to remain sterile for later use. For example, in some embodiments the custom sized container contains surgical equipment and the custom sized container is removed from the chamber and taken to an operating room. In this embodiment, the surgical equipment has remained sterile within the container and contains sterilized equipment for use by the medical staff. A custom sized container meant for surgical use could contain equipment including but not limited to retractors, clips, clamps, forceps, scissors, and needle holders. In some embodiments the container is coded to convey the contents. As a non-limited example, the container could be coded with the medical procedure for its intended use.

In some embodiments, the device to be sterilized within the custom sized container placed within chamber 10 is a FDA regulated device. In such embodiments, the FDA regulated device can include but is not limited to a pacemaker, a stent, a prosthetic heart valve, a bone screw, a retractor, surgical clips, surgical clamps, forceps, surgical scissors, or surgical needle holders. In some embodiments one item is sterilized, disinfected, sanitized, and/or decontaminated in the custom sized container within chamber 10 and another item is sanitized, and/or decontaminated in the remaining open space in chamber 10. In this embodiment, chamber 10 is dual purposed to sterilize two different devices, one within the custom sized container requiring a direct flow of sterilant and one outside the custom sized container. In such embodiments, the item placed inside the custom sized container requires more absolute sterilization than the item placed in the general space. In some embodiments of dual sterilization, the item placed inside the custom sized container is a FDA regulated device. In some embodiments of dual sterilization, the item placed in the open space of chamber 10 is an EPA regulated device such as an iPad or a phone. In some embodiments of dual sterilization, the item placed in the open space of chamber 10 is a low risk FDA regulated device such as a stethoscope or a blood pressure cuff. In some embodiments of dual sterilization, the item placed inside the custom sized container is a high risk FDA regulated device such as a stent or a pacemaker.

In some embodiments, chamber 10 is an entire room. In one embodiment of room decontamination, the room has sealed vents, such as AC vents and any other air vents, for example air heating vents. In some examples, the door must be sealed in order to prevent escape of the sterilant to other parts of the building. In some embodiments, a temporary airlock attaches to the door. The sterilant can be delivered to the room from the device/source that is located in the room or through the conduits, input and output, connected to the device that is outside of the room. In another embodiment of room decontamination, the room is sealed off from the outside to prevent the escape of the sterilant to other parts of the building. In one such embodiment a reversible sealing mechanism such as a tent is used to prevent the flow of air outside the room.

Some embodiments of the invention include an endoscope rack that sterilizes and disinfects endoscopes and similar devices including other lumen containing devices. For example the endoscope rack can be used with scopes related to the following fields, gastroenterology, endoscopic ultrasound scopes, pulmonology, ENT (ear, nose, and throat), speech, and urology. Additionally, in some embodiments scopes with working channels such as for biopsy or suction can be used with the endoscope rack. In some embodiments, a single endoscope rack can hold and process up to 40 endoscopes. In some embodiments the endoscopes are dried and stored in the endoscope rack and maintain sterility while inside the unit. In some embodiments the scopes will be hung lengthwise either proximal end up or distal end up in the endoscope rack. In some embodiments, the endoscope will be placed in the endoscope rack after they have gone through a disinfection cycle by another means such as an Olympus or Medivator liquid disinfection system. In such embodiments, the endoscope would be attached to a universal adapter, for example a clamshell that blows air into the working channel of the endoscope until it is dry. The drying process can be, for example, between 10 and 20 seconds. In some embodiments the dry cycle uses sterilant. In some embodiments the dryer will be a stand-alone unit. In some embodiments the endoscope will be placed in the endoscope rack as the first step in the disinfection process. In these embodiments, exposure of the endoscope to sterilant sterilizes the endoscope. In some embodiments, the sterility of the endoscope will be maintained through the placement of a single use, form fit barrier pouch (the endoscope pouch) that is placed over the endoscope in a loose fit and seals the endoscope off from the surrounding environment. The pouch is large enough to avoid tight contact between the scope and the pouch "wall".

In some embodiments, the inner wall of the pouch is made of a material such as TYVEK or a similar material to allow the effluent to penetrate the space where the endoscope touches the wall. The endoscope pouch is made of clear material to allow viewing of the endoscope make, model, and bar code while the endoscope is still inside the endoscope container. The endoscope pouch is impermeable to gas and retains effluent that is introduced into the pouch. Another advantage of the endoscope pouch is that once the endoscope sterilization cycle is completed, the endoscope can be transported to the exam room inside the pouch thereby remaining sterile. In some embodiments, the sterility of the endoscopes is further maintained through the use of chemical indicators built into the pouch to monitor the level of effluent. Additionally, biological indicators can be assessed in the morning and at night to determine if there is a proper level of biological kill. In some embodiments, continuous circulation of the effluent is achieved by having an inlet and outlet adapter whereby effluent is moved into and out of the pouch. In such embodiments, the inlet adapter will channel effluent directly into all lumens of the endoscope. In some embodiments, the adapter for the effluent inlet will have two ports, one with a direct connection to the lumen or lumens and one to direct effluent into the pouch. In this embodiment, the inputs will be decoupled in order to maintain proper pressure at each port. The lumen port will deliver the effluent to sterilize the lumens and the other port, the one directing effluent to the pouch, will deliver effluent to sterilize other parts of the endoscope. The outlet adapter will channel the old, used effluent back to the location of the evaporator and the plasma generator for re-processing. Unlike the input connectors, there will be only one common output. In a preferred embodiment, the output adapter is at the other end of the pouch from the input adapter. A similar process can be used to sterilize/disinfect an endoscope that does not have a lumen wherein the entire endoscope will still be exposed to effluent. In some embodiments the endoscope rack has multiple cycle settings. For example, cycles designed for sterilization, high level disinfection, and maintenance of sterility for endoscope storage. The sterilization and high level disinfection cycles vary by the length of the cycle time with a longer cycle used for the sterilization cycle. The maintenance cycle is designed to maintain the sterility/disinfection of the endoscope during storage and before use. For example, the endoscope could be placed in the endoscope rack and sterilized at night and stored for use in the morning. Use of the maintenance cycle on the endoscope rack would ensure that the endoscope is sterile/disinfected for use in morning procedures. The maintenance cycle could be run, for example, once every four hours while the endoscopes are stored overnight. A set timer could be used to initiate maintenance cycles throughout the night or the duration of storage in the endoscope rack. In some embodiments each endoscope rack would have light indications that coordinate with the current cycle of the endoscope rack. For example, a red light would indicate that the endoscope rack is currently undergoing a sterilization/disinfection cycle, a yellow light would mean that a maintenance cycle is underway, and a green light would mean that no cycles are currently processing and the endoscopes are ready for use. In some embodiments the endoscope drying rack is modular and it is possible to start and stop a cycle on a particular scope at different times. In some incidences, a single endoscope will be placed in and removed from the endoscope rack about 3 to 4 times per day under normal hospital use.

In some embodiments there is a controller unit that houses, the plasma generator, the evaporator, the hydrogen peroxide cartridge, fans, as well as the electronics and control boards for the device. In some embodiments, the controller unit would be small enough in size to be placed on a wall or counter. In some embodiments, the chamber and the control unit would be separate units that are connected by tubing. In these embodiments, tubing would carry sterilant both from the control unit to the chamber and then from the chamber back to the control unit to be reprocessed. The basic device of the control unit can be used to sterilize/decontaminate a variety of objects dependent on the chamber attached to the control unit. For example, in some embodiments the control unit is connected to an endoscope drying and treatment rack where endoscopes are sterilized. In some embodiments the same control unit is connected to a chamber designed to hold communication devices where iPad, cell phones, and pagers, for example, can be sterilized/decontaminated. In some embodiments the control unit is used to determine the sterilization cycle of the device based on the objects placed in the attached chamber. For example, in some embodiments the chamber holds endoscopes and the controller unit will be set to sterilization. In another example, the chamber will hold communication devices and the controller unit will be set to rapid disinfection.

An effluent generator 46 is used for production of effluent for sterilization or decontamination of the chamber and its contents and for powering the circulation of effluent in the closed loop, to be described later. The effluent generator 46 includes a flow generator (e.g., a circulating pump, a positive displacement pump, an air conveyor, a fan, or a blower with flow distributor 14), a free radical supply unit (e.g., a cold plasma generator such as a plasma electric free radical generator 30, ozone generator or any other type of system that generates free radicals, such as a dielectric barrier discharge system), and a vapor supply unit (e.g., an evaporator or vaporizer 32). The flow generator can include a controllable-speed type (e.g., variable speeds) or a single-speed type. Although various embodiments can be utilized in room pressures, in some instances, varying the speeds may allow use of slight negative or positive pressure. In some embodiments, a slight negative pressure may advantageously keep the effluent within the system as a safety precaution. In some embodiments, the pressure may be approximately 1 to 2 cm of $H_2O$ lower than ambient pressure.

The plasma free radical generator 30 can be any kind of dielectric barrier discharge device, electrical corona device, a glow discharge device, or a microwave generator. One non-limiting example of a device which can be used within the teachings of the disclosure is an ozone generator such as, for example, ozone generator cell SY-G20 manufactured by Longma Industrial Zone, Bao'an District, Shenzhen, 518108, P.R.C.

In several embodiments, the vaporizer 32 contains liquid sterilizing agent such as hydrogen peroxide solution, though other agents known to those of ordinary skill could be used, as discussed below. Additionally, in several embodiments, a solid agent could be used that is converted into a liquid during the sterilization cycle. The gas entering the vaporizer, comes into contact with the solution, and produces an effluent comprising reactive oxygen species (e.g., bactericidal effluent). While certain embodiments are described with particular reference to hydrogen peroxide as the sterilizing agent, it will be appreciated that the system is also applicable to other solutions and pure liquids, such as peracetic acid or formalin solution.

The vaporizer 32 can be in the form of a "bubbler", in which the gas passes through a container of liquid, or the vaporizer could use plates or wicks over which the gas passes. Preferably, the vaporizer 32 uses a measured amount of sterilizing agent, preferably in a pre-measured cartridge which can be inserted into the vaporizer, such that the agent is substantially or completely consumed in the course of a sterilizing run. The vaporizer can thus supply a specific small amount of hydrogen peroxide to the evaporator from a cartridge which is emptied and dried during the sterilization process. In some embodiments, the hydrogen peroxide concentration can be from about 30% to about 60% concentration, e.g., about 30%, about 35%, about 40%, about 45%, about 50%, about 55%, or about 60% concentration. In some examples, the hydrogen peroxide vapor concentration can be from about 100 ppm to about 10,000 ppm or any ranges in between such as about 100 ppm to about 600 ppm. At the end of the sterilization cycle, the final hydrogen peroxide vapor concentration can be about 600 ppm or less (e.g., about 550 ppm or less, about 525 ppm or less, about 500 ppm or less, about 475 ppm or less, about 450 ppm or less, about 425 ppm or less, or about 400 ppm or less) in some embodiments, allowing for less condensation and better material compatibility. The drying of the cartridge is accomplished by heating it using a small heater or dryer and a limited filtered air flow through the cartridge into the system. This way there is reduced or no danger that hydrogen peroxide liquid is present in the cartridge at the end of the cycle when a person/operator will insert a new cartridge for next cycle. In alternative embodiments, a cartridge is provided that contains enough sterilant for a certain number of cycles (e.g., 5 cycles, 10 cycles, etc.), for use in circumstances where there are a higher number of cycles used on a regular basis. In such embodiments, as above, the cartridge is optionally dried before a system lock allows the cartridge to be removed by a user. In still additional embodiments, akin to an "all in one" espresso machine, certain embodiments dispose of the cartridge internally to the machine, reducing the risk to users, and a new cartridge is inserted in its place when prompted by the system.

In some embodiments, the vaporizer 32 may be filled with hydrogen peroxide liquid before each cycle to a certain prescribed level so that there is enough liquid to last to the end of the cycle. In such embodiments, the cycle may be continuously in free radical saturation. The remaining liquid in the vaporizer 32 can be utilized in the next cycle because hydrogen peroxide does not decompose between cycles (e.g., if the time between cycles is not long such as more than two weeks, three weeks, four weeks, or months). In some embodiments, if the liquid (e.g. hydrogen peroxide) in the vaporizer decomposes below an acceptable level (e.g. 5% below the original level) the liquid is drained from the vaporizer and discarded.

The blower with the flow distributor 14 takes recirculated effluent from the chamber 10 via conduit 36, and distributes it proportionally through conduit 40, which is coupled, optionally through a filter 50, into the plasma generator 30, and through conduit 38, again through optional filter 50, into vaporizer 32. The recirculated effluent is preferably distributed in proportions of approximately 30% to conduit 40, and approximately 70% to conduit 38, although other proportions could be used within the teaching of the disclosure. For example, in some embodiments, the effluent can be distributed in portions of approximately ⅓ to the plasma generator 30 and approximately ⅔ to the vaporizer 32 by having a single conduit 40 leading to the plasma generator 30 and two conduits 38 leading to the vaporizer 32. Other embodiments employ ratios of about 10:90, 20:80, 40:60; 50:50, 60:40, 70:30, 80:20, and the like.

With the proportions noted above, most of the recirculated effluent bypasses the plasma generator 30, passing only through vaporizer 32. The lesser proportion of the effluent passes through plasma generator 30, picking up new free radicals, and is mixed back in the rest of the effluent from the vaporizer 32 at junction 48. Accordingly, the sterilant can be rejuvenated multiple times without filtering out the active species and/or free radicals resulting in a sterilization process comprising a single cycle of continuous flow. By rejuvenating the sterilant without filtering out the reactive species and free radicals, various embodiments can achieve constant peak efficiency. For example, various embodiments can maintain a peak free radical mixture in a relatively short cycle time, as opposed to other technologies that refresh the sterilant throughout the process, thereby requiring longer times to completion.

The effluent produced in the effluent generator 46 is then introduced into the chamber 10, completing the closed loop of the system. In FIG. 1A, the free radicals from the plasma generator 30 and the effluent from the vaporizer 32 are mixed from the sterilant prior to introduction into the chamber 10. In various embodiments, the sterilant includes substantially only free radicals and humidity such that there is no condensation of hydrogen peroxide and exposure to the item being sterilized. In other embodiments, the plasma generator 30 and the effluent from the vaporizer 32 may be mixed within the chamber 10, e.g., by use of a baffle. In such embodiments, the plasma may be advantageously generated within the chamber 10 without application of a radio frequency (RF) field into the chamber 10. In FIG. 1A, the plasma generator 30 and the vaporizer 32 are disposed in parallel. In other embodiments, the vaporizer 32 and the plasma generator 30 are disposed in series, e.g., with the vaporizer 32 placed prior or after the plasma generator 30. In some such embodiments, a dryer may be placed a prior to the plasma generator 30.

In various embodiments, the generated atmospheres in the chamber 10 has sterilizing (or disinfecting, sanitizing, decontaminating, and/or therapeutic aspects). Advantageously, the generated atmospheres in several embodiments undergo a relatively gentle process that is compatible with all natural and manmade materials. In some embodiments, the generated atmospheres are produced with a "green" process, e.g., utilizing relatively low power consumption and producing non-toxic products and by-products.

Quality control and/or regulatory compliance indicators (e.g., disposable after every cycle, semi-disposable for use after a number of cycles, or non-disposable) may be incorporated in many embodiments. For example, indicators can provide information to an operator of proper delivery, amount, and/or mix of sterilant to the chamber 10. An example includes a chemical strip in a holder within the chamber 10. For a semi-disposable strip for a certain number of cycles (e.g., 2, 3, 4, 5, 6, 7, 8, 9, 10, 12, 15, 20, etc.), in some embodiments, only a portion of the strip may be exposed for each cycle. As another example, a chemical strip may be incorporated into a label for a chamber such as for the case where the chamber is a plastic bag (e.g., a Tyvek® bag). In some such embodiments, the indicator may travel with the item (e.g., when placed or removed from the chamber). As yet another example, a sensor (e.g., a hydrogen peroxide sensor) may be incorporated in an automated fashion. Other examples are possible.

In addition to the closed loop system, an open loop system is also provided. In one embodiment, an open loop system is for the purpose of pre-heating (optionally) and drying the chamber 10 before and after the circulation of bactericidal effluent through the closed loop system. The open loop system uses a flow generator (e.g., an exhaust pump, an air conveyor, a fan, or a blower 16), exhausting to atmosphere 56, to draw air from an air input 58 through an input controller (e.g., an input valve 18) and an optional heater 26 into chamber 10. The input air may be filtered by filter 20, which is preferably of the high efficiency particulate air (HEPA) variety or a military grade filter.

The fresh (heated or not heated), filtered air is introduced into the chamber 10 through conduit 42.

In the open-loop operation mode, the output of the chamber 10 is drawn out by blower 16 and passes through conduit 44 and a Free Radical Destroyer (FRD) 24, which destroys any free radicals which might remain before the air is exhausted 56. A second filter 22, again preferably of the HEPA type, can be provided in conduit 44 to filter out any particles which would otherwise enter the FRD or be exhausted to the atmosphere. The presence of HEPA filters 20 and 22 at the input and exhaust ensures that there is substantially no microorganism transfer between the ambient air and the sterilization system and vice versa. The order of the filter 22, FRD 24, and blower 16 can be in any order.

The simplest FRD is an activated carbon filter, for example, the Vent Pure "D" from General Carbon Corp. of Paterson, N.J. Other examples include filters comprising a noble metal (e.g., platinum, silver, gold, etc.) or ceramic. In some embodiments, a catalytic converter might be used to convert harmful compounds to less harmful ones.

By opening valve 18 and turning on heater 26 and blower 16, the chamber 10, and items 56 within the chamber, can be dried and pre-heated before the closed loop operation is begun. Once the pre-heating and drying step is completed, valve 18 is closed and heater 26 is turned off Preferably, blower 16 is of a controllable-speed type, so that it may be operated at a reduced speed during closed-loop operation. In some embodiments, this will induce a slight negative pressure in the chamber 10, preventing leakage of effluent from the chamber. However, the blower could be a single-speed blower, in which case it would be turned off after the pre-heating step.

After optionally pre-heating, in several embodiments, the system is operated in closed-loop mode by starting blower/distributor 14 and plasma generator 30. The effluent mixture circulates continuously through the loop, from generator 46 through conduit 34, through chamber 10 and conduit 36, back to the generator 46.

When this cycle is finished plasma generator 30 is turned off, valve 18 is opened, and blower 16 is turned on full speed in order to remove the active free radicals from the effluent using FRD 24, and to dry the chamber 10 and the sterilized equipment 56 or 62.

The closed loop blower/distributor 14 may remain on, if desired, so as to circulate air through the closed loop to dry the free radical source 46 and vaporizer 32. Heater 26 may optionally be turned on at this stage, as well, so that heated air is circulated through the vaporizer in order to evaporate residual remains of liquid solution of hydrogen peroxide. Alternatively, blower/distributor 14 may be turned off if it is not desired to circulate air through the closed loop portion of the system during this drying step.

A controller 12 is provided in order to control the operation of the various parts of the system.

As described herein, various embodiments may be operated at ambient conditions (e.g., room temperature). Such embodiments may be advantageous in hospital settings where air conditions and humidity are controlled. However, some embodiments may adjust the conditions within the chamber 10 to a more effective environment. For example, if the ambient temperature were too cool or too warm, some embodiments are configured to self-regulate or control the temperature in the chamber 10 to a desired temperature (e.g., within an operating range for sterilant effectiveness). Another aspect of the sterilizing cycle is to control Relative Humidity in the chamber. The humidity can be varied during the cycle from lower humidity at the beginning of the cycle to higher humidity toward the end of the cycle depending on the initial conditions of the items to be sterilized. For example, some items may contain residual moisture from washing or were stored in moist environment. In such case it is necessary to remove the residual moisture from the items in order to accomplish full sterilization.

In general, a lower ambient temperature may slow the sterilization process, while a higher ambient temperature may speed up the process. As will be described herein, various embodiments may self-regulate or control humidity such that the humidity of incoming air does not adversely affect the humidity in the chamber 10. Hydrogen peroxide can replace water in the atmosphere and water can condense out. Under many anticipated environmental conditions (e.g., hospital conditions), self-regulation and control measures can be incorporated. In more severe environment conditions (e.g., jungle environments), additional purge valves and methods may be incorporated, such as to purge the vaporizer 32 at various intervals and to bled out hydrogen peroxide (e.g., in case of shipping or transport or when the hydrogen peroxide decomposes below the desired w/w % level)).

In various applications, moisture control (e.g., self-regulation or control) may be important to reduce or avoid unwanted condensation. Absent adequate moisture control, there may be the potential of water vapor and/or hydrogen peroxide vapor condensation forming on the walls of the chamber 10 as well as on articles in the chamber 10. The resulting layer of water and hydrogen peroxide condensation can cause adverse effects on the articles being sterilized in some instances. As one example, when electronic devices are being sterilized, excessive condensation could potentially create electrical shorts and otherwise damage the electronic devices.

Moisture control is also important in the sterilization process when items or their parts to be sterilized are wet and pathogens are "hiding" under a layer of moisture preventing the access of free radicals in the sterilant to the pathogens. In such conditions part of the sterilization cycle is to maintain the circulating sterilant at much lower relative humidity level in order to remove the remnants of the moisture from the article. In some embodiments where there is a layer of moisture preventing access of free radicals in the sterilant to the pathogens, the target relative humidity level is maintained at 20-30% for some amount of time before the sterilization process is started.

In some embodiments, the vapor pressure of the sterilant may be maintained at or below the saturation level in the sterilization chamber (e.g., for the pressure and/or temperature inside of chamber 10). By doing so, various embodiments can reduce or eliminate condensation buildup on the items being sterilized, on the walls of the chamber 10, and on other components exposed to the sterilant, such as hoses and fittings described herein. FIGS. 1B-1D illustrate some examples of evaporators 32a, 32b, and 32c configured to control the vapor pressure of the sterilant. Each of evaporators 32a, 32b, and 32c is usable as the vaporizer 32 in all of the embodiments described herein and may produce, in many instances, a substantially non-condensing output.

As shown in FIG. 1B, evaporator 32a may comprise two concentric tubes 121a, 121b with a wicking material 132 disposed between the tubes 121a, 121b. In operation, the evaporator 32a can receive sterilizing agent 128 (e.g., hydrogen peroxide solution or other suitable sterilizing agent liquid) for example, forming a pool of liquid near the bottom of the evaporator 32a. The evaporator 32a may include a float 130 to regulate the level of the sterilizing agent 128. For example, a controller (e.g., controller 12 shown in FIG. 1) can electronically monitor the position of the float 130. The float 130 can include a magnetic switch float such as, for example, 9FS01-0112 manufactured by Strain Measurement Devices, Inc. 55 Barnes Park North, Wallingford, Conn. 06492. Based on the position of the float 130, the controller 12 can open or close an intake valve to maintain the desired level of sterilizing agent 128.

In some embodiments, the evaporator 32a may comprise a piezoelectric transducer 126 (or other suitable vibration element). The piezoelectric transducer 126 may be configured to create a mist 124 of the sterilizing agent 128, which may be absorbed by wicking material 132.

As indicated by the arrows in FIG. 1B, the evaporator 32a may take in gas (e.g., air or other medium) at intake 122. If desired, the intake 122 may extend below the level of the sterilizing agent 128, such that the incoming gas bubbles through the sterilizing agent 128, encouraging evaporation and misting. The gas may then pass through mist 124. In at least some arrangements, the flow of the gas may assist in the formation of mist 124. In other words, the flow of the gas may cause some of the sterilizing agent 128 to move into the lower regions of the wicking material 132. Evaporation of the sterilizing agent 128 may occur primarily within the wicking material 132, which is at least partially saturated with sterilizing agent 128. In other words, the wicking material 132 may be formed from a porous material that, due to its porous nature, has a large internal surface area which enhances evaporation.

In at least some arrangements, by saturating the lower portions of wicking material 132, the upper portions of wicking material 132 (e.g., the portions further from the pool of sterilizing agent 128) may remain relatively dry. As such, the wicking material 132 may serve to both encourage evaporation and to reduce/avoid producing vapor that is over-saturated (e.g., to avoid or minimize formation of droplets or mists of the sterilizing agent 128 at the output 134 of the evaporator 32a). Put another way, even if the evaporator 32a were to produce over-saturated sterilant vapor in the lower regions of the wicking material 132, the upper portions of the wicking material 132 would drive formation of condensation and then absorb the condensation, such that the final output would be merely saturated or below saturation levels.

As another example, the float 130 may include a level control float sensor/switch 130 configured to regulate the level of sterilizing agent 128. In operation, sterilizing agent 128 may be received through the float switch 130. As sterilizing agent 128 is evaporated into the gas flow, float sensor/switch 130 may sense a drop in the level of the sterilizing agent 128 and open an intake valve to refill the sterilizing agent 128 in the evaporator 32a.

Alternatives for maintaining the level of sterilizing agent 128 may be used. As one example, a sensor may be provided that measures the level of sterilizing agent 128 and a controller (e.g., controller 12 shown in FIG. 1A) may open or close an intake valve in response to measurements from the sensor at the beginning of each cycle. Other examples of liquid level measurement devices include using a laser or a mechanical switch.

In various embodiments, the wicking material 132 and other components of the evaporator 32a that may come into contact with the sterilizing agent 128 may comprise materials that are resistant to the sterilizing agent 128 (e.g., hydrogen peroxide). In arrangements also including a plasma generator 30 (e.g., an ozone generator) and in which the sterilant is recirculated, the wicking material 132 and other components of the evaporator 32a that may come into contact with the recirculated sterilant may comprise materials that are also resistant to the sterilant (e.g., which may include ozone).

FIG. 1C illustrates an evaporator 32b in which the piezoelectric transducer 126 is omitted. In some such arrangements, the liquid sterilizing agent 128 may be transferred to the wicking material 132 by the gas flowing through the evaporator 32b (e.g., by bubbling, by direct liquid surface deformation, etc.). If desired, wicking material 132 may be extended into sterilizing agent 128 (e.g., the sterilizing agent 128 may be maintained at a level that is in contact with wicking material 132) such that no bubbling or misting is required to draw the sterilizing agent 128 into the wicking material 132. In other embodiments, multiple layers of wicking material may be used, e.g., a first wicking material that contacts the sterilant directly and is interwoven or overlaid (optionally reversibly) with another wicking material (optionally of the same type as the first) that is relatively permanent to the device (though it is optionally replaceable). Such techniques may also be utilized in embodiments including piezoelectric transducer 126. FIG. 1C also illustrates that the output 134 may be arranged in a different way.

FIG. 1D illustrates an evaporator 32c that may include an input 136 and/or a drain 138 for the sterilizing agent 128. During operation, float switch 130 or other suitable mechanism may maintain the level of the sterilizing agent 128 in the evaporator 32c by adding sterilizing agent 128 from input 136 and/or by removing sterilizing agent 128 from drain 128. In addition, when the evaporator 32c is shut off or during desired portions of a sterilizing process, the evaporator 32c may be drained through drain 138. By draining the sterilizing agent 128 through drain 138, the evaporator 32c can, if desired, be quickly dried out (e.g., to reduce any danger of any remaining hydrogen peroxide). Drying out the evaporator 32c may include passing air through the wicking material 132 to absorb any remaining sterilizing agent 128. Additionally, maintaining a particular level of sterilant, in several embodiments, optimizes the overall process, as too much or too little sterilant being incorporated into the effluent can lead to inefficient sterilization, while too much may damage the items to be sterilized.

In various embodiments described herein, evaporation can occur passively (e.g., without heat) by the flow of air through the wet wicking material. In some instances, equilibrium between liquid and vapor can be reached at or below the saturation level. Accordingly, various embodiments may simply adjust the saturation level of the sterilizing agent 128, but need not adjust the concentration of the sterilizing agent 128. Also, by controlling the level of moisture, certain embodiments do not require the use of heat in the vaporizer 32.

Figure 1E:
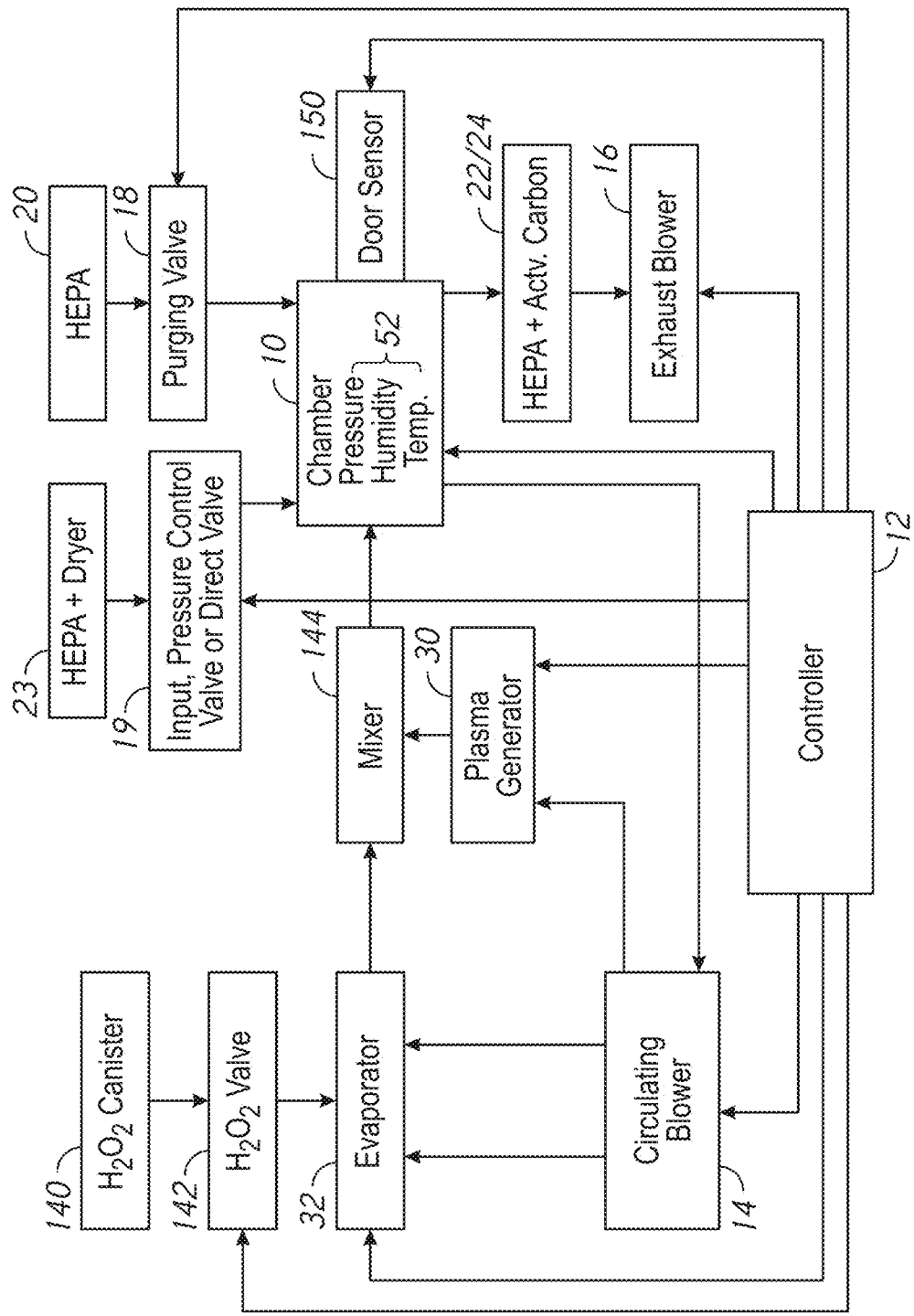
FIG. 1E shows a block diagram of an example embodiment using a regulated input of fresh, dry air and associated exhausting of circulating effluent to reduce or prevent buildup of condensation in the chamber.

FIG. 1E illustrates an example embodiment that may be used to regulate the water vapor saturation level as well as the sterilant vapor saturation level within the sterilization chamber 10. Some embodiments include other features as described herein such as a hydrogen peroxide canister 140, a hydrogen peroxide valve 142 that feeds hydrogen peroxide into evaporator 32, and a door sensor 150 that determines when chamber 10 is open and/or closed. Some embodiments may also include a mixer 144 in which the sterilant vapor and plasma effluent are mixed before entering chamber 10.

As shown in the example of FIG. 1E, various embodiments may include a sensor 52 in the chamber 10. The sensor 52 may include one or more humidity sensors (sometimes referred to as hygrometers), one or more temperature sensors, and/or one or more pressure sensors. Some embodiments may also include an input pressure control valve 19. In operation, controller 12 may use sensor 52 to determine when the vapor saturation level within chamber 10 is approaching a threshold level likely to produce undesired condensation (e.g., when the vapor level is approaching saturation). For example, when the pressure difference between the chamber 10 and the outside environment reaches a set value (e.g., the threshold level), controller 12 may send an appropriate control signal to increase the power of the exhaust blower 16. This opens the input pressure control valve 19 to allow fresh, dry air (e.g., air dried by dryer 23) into the chamber 10 to reinstate the pressure in the chamber 10.

Alternatively, some embodiments may include a direct valve 19 instead of the input pressure control valve. When the pressure difference between the chamber 10 and the outside environment reaches a set value (e.g., the threshold level), controller 12 may send an appropriate control signal to open the direct valve 19 to allow fresh, dry air (e.g., air dried by dryer 23) into the chamber 10. The exhaust blower 16 removes effluent from the chamber 10 to maintain the prescribed pressure difference between the chamber 10 and ambient environment.

In some other arrangements, controller 12 may activate or increase (or decrease) the speed of exhaust blower 16, may activate or increase (or decrease) the speed of an intake blower such as dryer 23, may activate or increase (or decrease) the heating power of a drying unit attached to the air intake such as dryer 23, may partially or fully open the purging valve 18, may take other suitable steps, or may take any combinations of these and other steps. As additional fresh, dry air enters chamber 10 and is recirculated by blower 14, the vapor saturation will be reduced. In some arrangements, controller 12 may cycle the introduction of fresh air (e.g., stop adding fresh after the vapor levels fall to a second and lower threshold). In other arrangements, controller 12 may modulate the amount of fresh air introduced into the system in real time in order to maintain the vapor levels at a desired level or within a desired range.

Figure 1F:
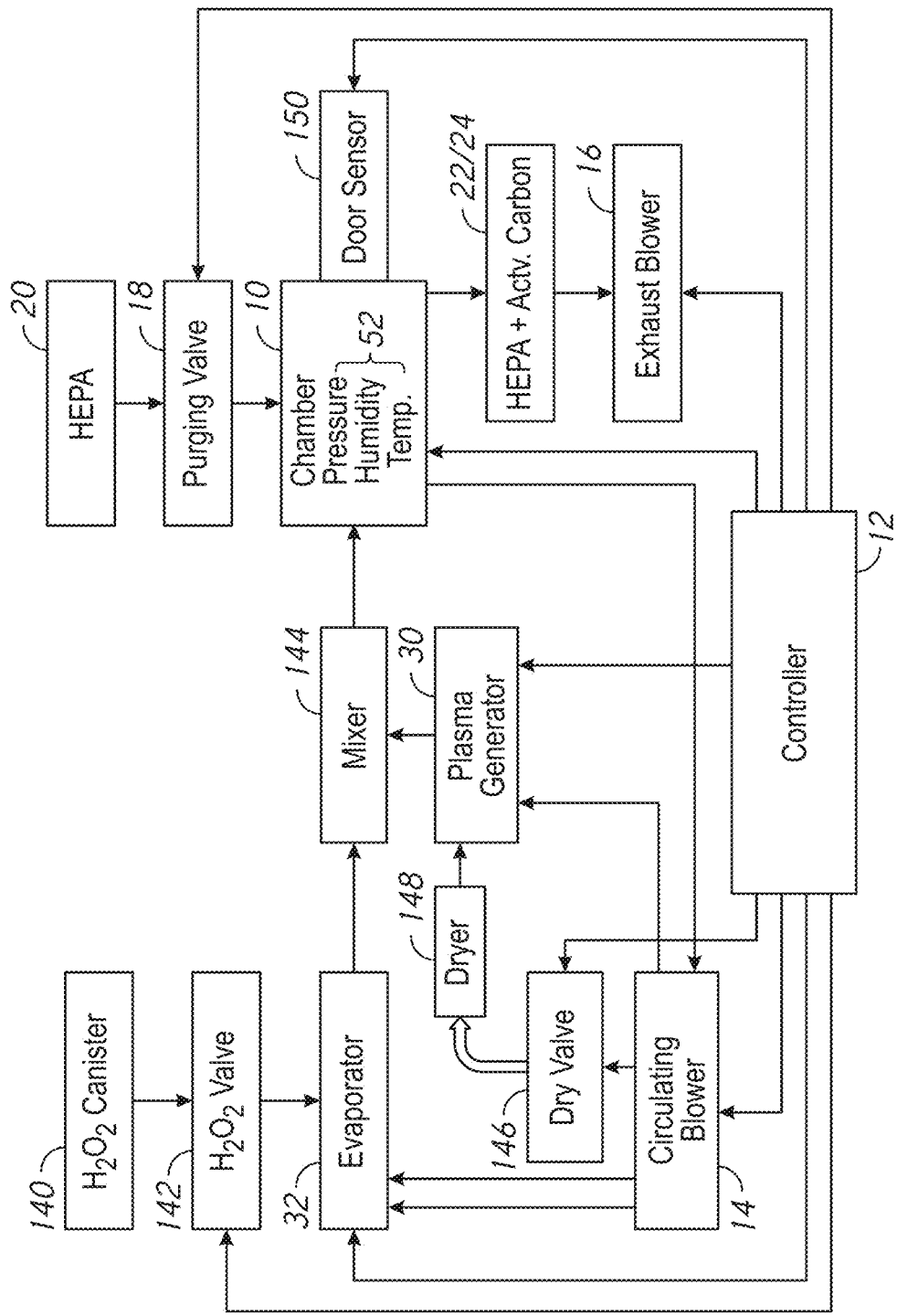
FIG. 1F shows a block diagram of an example embodiment using a dryer in a partial bypass of the effluent supply to the plasma generator to prevent or reduce condensation in the chamber.
Figure 1G:
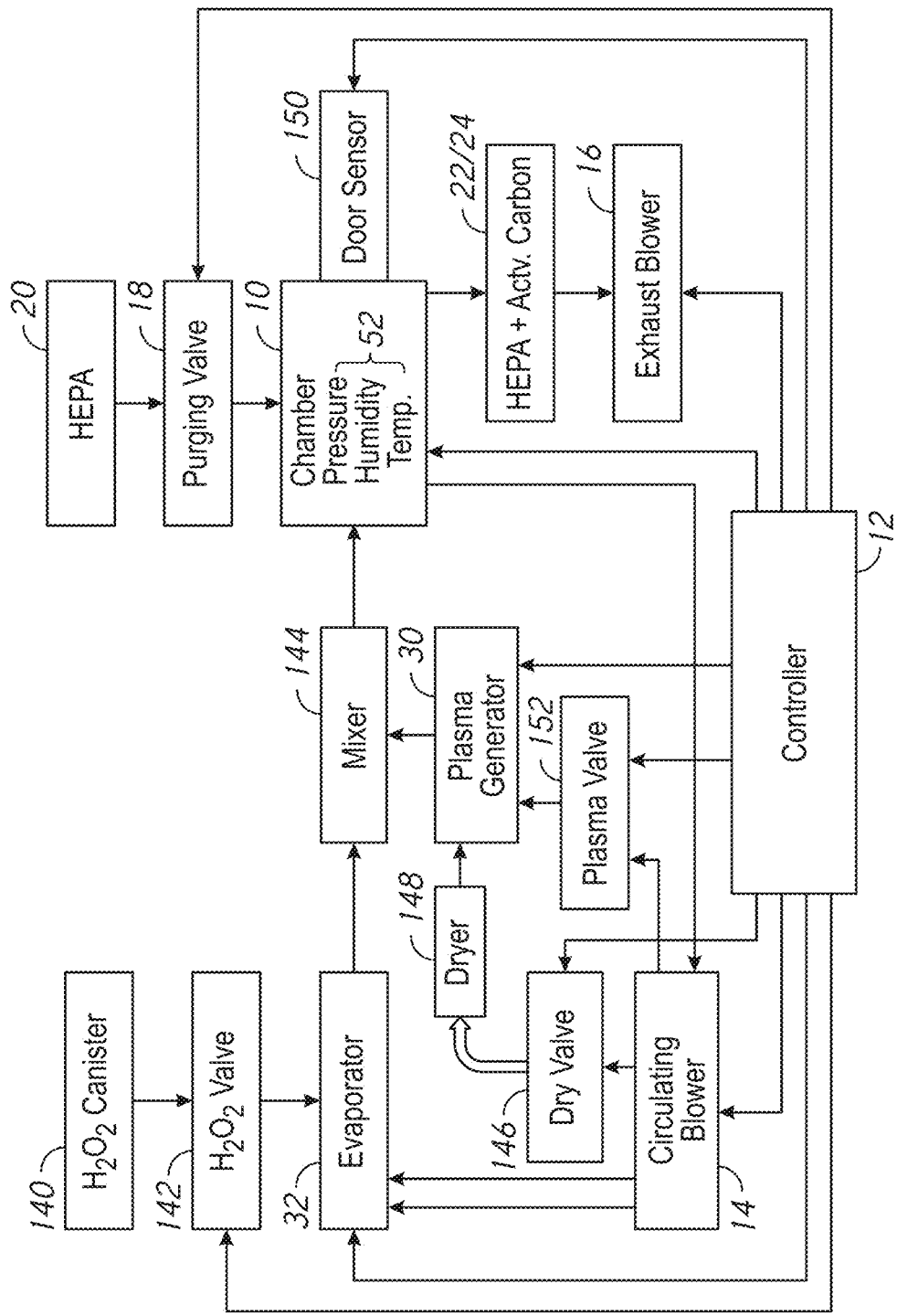
FIG. 1G shows a block diagram of an example embodiment using a dryer in a full bypass of the effluent supply to the plasma generator to prevent or reduce condensation in the chamber.

FIGS. 1F and 1G illustrate additional example embodiments configured to help maintain desired vapor saturation levels to reduce or avoid undesired condensation. Such embodiments may control the vapor saturation level within the sterilization chamber 10 by incorporating a dryer 148 in the recirculating loop of sterilant, e.g., prior to the plasma generator 30. In such examples, the circulating vapor that exits the plasma generator 30 may be slightly dryer than the vapor exiting the evaporator 32 resulting in a dilution of the vapors in the mixer 144 and lowering the saturation level to below the set level (e.g., the condensation level). Dryer 148 may be any suitable dryer. As examples, dryer 148 may be a desiccant dryer or a dehumidifier utilizing a refrigeration system.

As shown in FIG. 1F, dryer 148 may be disposed in a partial bypass of the intake to the plasma generator 30. In other words, a portion of the recirculating gas may be routed directly from the circulating blower 14 to plasma generator 30, while a second portion may be selectively routed from blower 14, through dryer 148, and then to generator 30. In the manner discussed in connection with FIG. 1R, controller 12 may use a sensor 52 to monitor the humidity levels and other factors (e.g., to determine the risk of unwanted condensation) and may control dryer 148 and bypass valve 146 in response. In particular, when humidity levels reach saturation (or some other desired threshold), controller 12 may open bypass valve 146 enabling the flow of gas through dryer 148 and controller 12 may also activate dryer 148. In some arrangements, controller 12 may maintain a desired humidity level by regulating the amount of bypass through valve 146 (e.g., by varying the amount or time that valve 146 is open), by regulating the drying effect of dyer 148 (e.g., by varying the drying power of dryer 148), by other methods such as those described in FIG. 1E, or by some combination of these and other techniques.

As shown in FIG. 1G, some embodiments may be capable of having dryer 148 in a full bypass arrangement. In particular, the system may include plasma valve 152. In response to the humidity levels in chamber 10 and other suitable criteria, controller 12 may partially or fully shut plasma valve 152 while partially or fully opening dry valve 146. In other words, controller 12 may have some or even all of the gas fed to plasma generator 30 pass first through dryer 148. In the manner noted above, controller 12 may then regulate dryer 148 to maintain desired humidity levels in chamber 10 and thereby avoid undesired condensation. In some embodiments, another option to regulate humidity in the chamber is to introduce controlled amount of fresh air that is drawn to the chamber through a desiccant/dryer. A non-limiting example of this is illustrated in FIG. 1E.

Systems Employing a Residual Coating Device

Figure 1H:
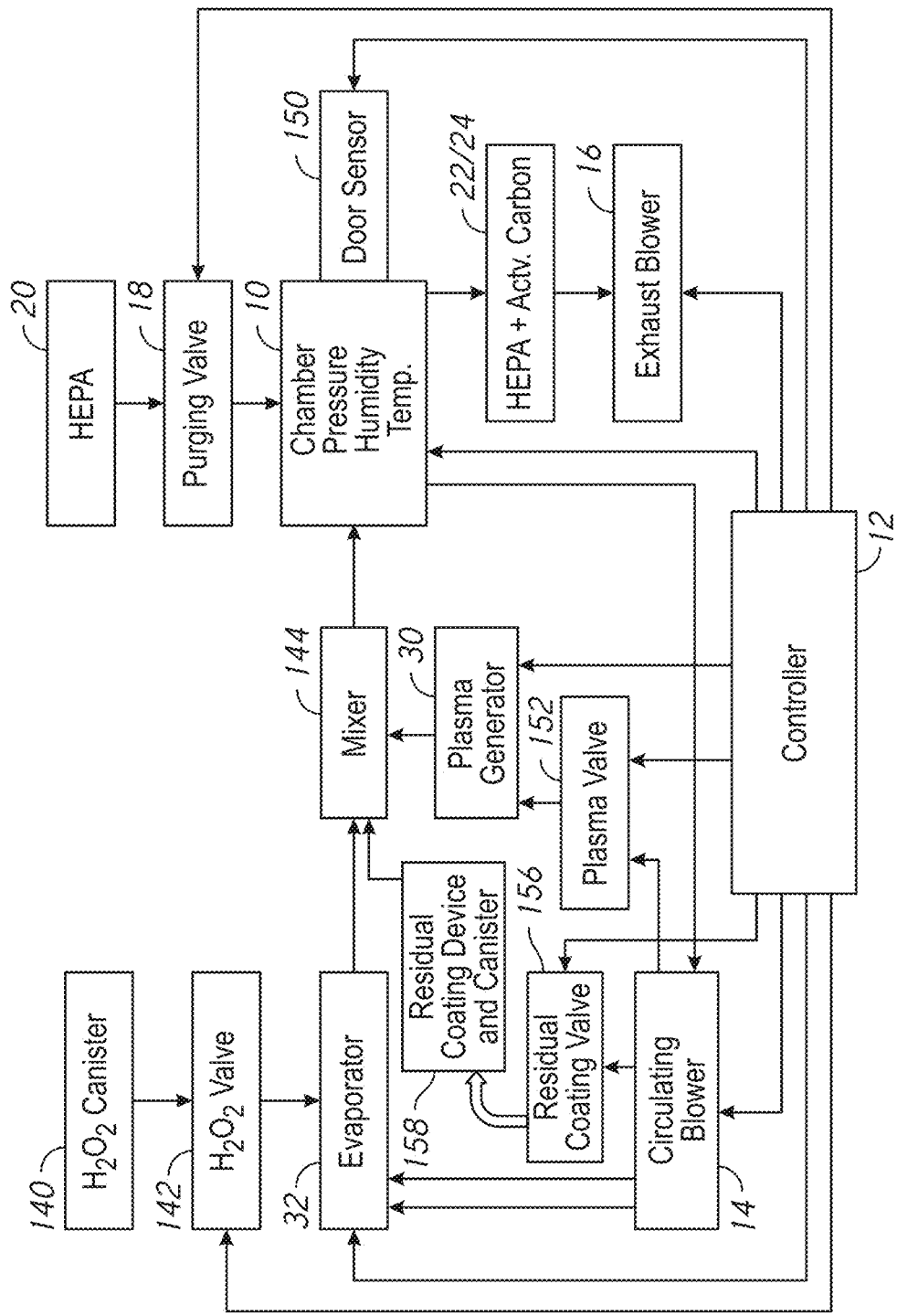
FIG. 1H shows a block diagram of an example embodiment using a residual coating deposition device to deposit a protective coating on items in the chamber.

FIG. 1H illustrates an additional embodiment including a residual coating device 158 that deposits a residual coating on items in chamber 10. In particular, the system may include a residual coating device and canister 158 and an optional residual coating valve 156. The residual coating device 158 may be used to deposit a residual coating on items in chamber 10. As an example, the residual coating device 158 may form a residual coating that is bactericidal, that is sacrificial and removable after potential contamination, etc.

In several embodiments, the residual coating device 158 generates a residual coating liquid or vapor that is conveyed to chamber 10 and deposited on items within chamber 10. The residual coating may be a material that has bactericidal properties such as silver, copper, or a combination of bactericidal materials. The residual coating may be formed from materials that are compatible with the items the coating is deposited on and may also be biocompatible with human subjects, especially in arrangements in which the items the coating is deposited on are items that come into contact with patients or other persons (e.g., surgical tools, endoscopes, dental products, infant care products, etc.). The residual coating material contained in canister 158 may be a gas, a liquid, a solid agent that is converted into a liquid during the coating cycle, or other suitable material. Gas entering the coating device 158 may come into contact with the residual coating material and the device 158 may then produce an effluent including coating material. In at least some arrangements, coating material may be aerosolized, sprayed or painted onto items in chamber 10 by device 158. While shown in FIG. 1H as being in a closed loop path of the type described herein, residual coating device 158 may also be integrated into chamber 10 or disposed in an open and non-recirculating path.

The residual coating device 158 may apply residual coatings to various products in chamber 10 including, but not limited to, cosmetics, eye ware, dental products, home use products for a medical condition (e.g., CPAP masks), infant care products, and pet care products. In general, the present disclosure applies to various industries that include but are not limited to, health care, sports medicine, veterinary care, dental care, agriculture, food processing, research, packaging, pharmaceuticals, packaging of pharmaceuticals, home health, day care, senior care, private and public services, and military/emergency field care. The process of residual coating, along with the other processes described herein, may be utilized in any field in which sanitization, disinfection, and/or sterilization is desirable.

The residual coating may serve to inhibit or prevent future growth of mold, bacteria, or other contaminants on items (which may be items that have been or will be sterilized in chamber 10). The residual coating may also include a sacrificial material that forms a barrier between the items in chamber 10 and external contaminants. The residual coating may be a layer that lasts for multiple sterilization cycles through chamber 10, or may be a layer that lasts as few as a single sterilization cycle, depending at least in part upon the material contained in canister 158 and deposited by device 158 and the sterilization process details (e.g., duration of sterilization, use of evaporated sterilant, use of a plasma generator, etc.).

Residual coating device 158 may include a canister containing coating material (i.e., a consumable canister). While FIG. 1H illustrates the canister and coating device schematically as one unit, the residual coating canister may be provided separately. In at least some embodiments, the residual coating canister, the hydrogen peroxide canister 140, and any other consumable canisters in the system may be provided in a combined canister system (i.e., replaceable as a whole) or may be provided as individually-replaceable canisters.

As shown in FIG. 1H, some embodiments may include a residual coating valve such as valve 156. Controller 12 may selectively open valve 156 during coating operations (e.g., when the system is coating objects in chamber 10 with a residual protective coating).

Systems Employing Plasma or Vaporizer Only and No Pre-Heater

Figure 4:
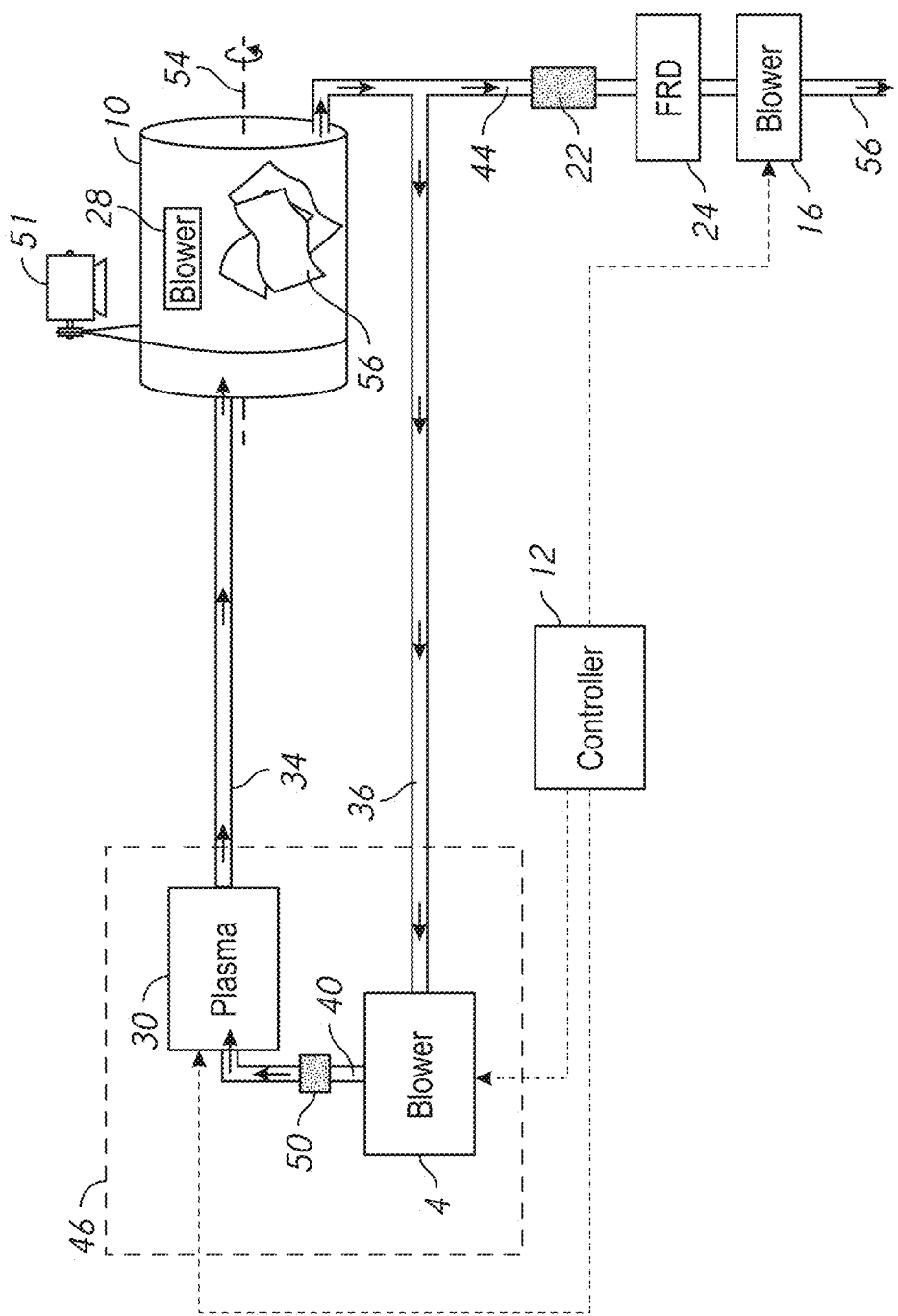
FIG. 4 shows a block diagram of a variation on the embodiment of FIG. 1, omitting the preheater, distributor and vaporizer.
Figure 5:
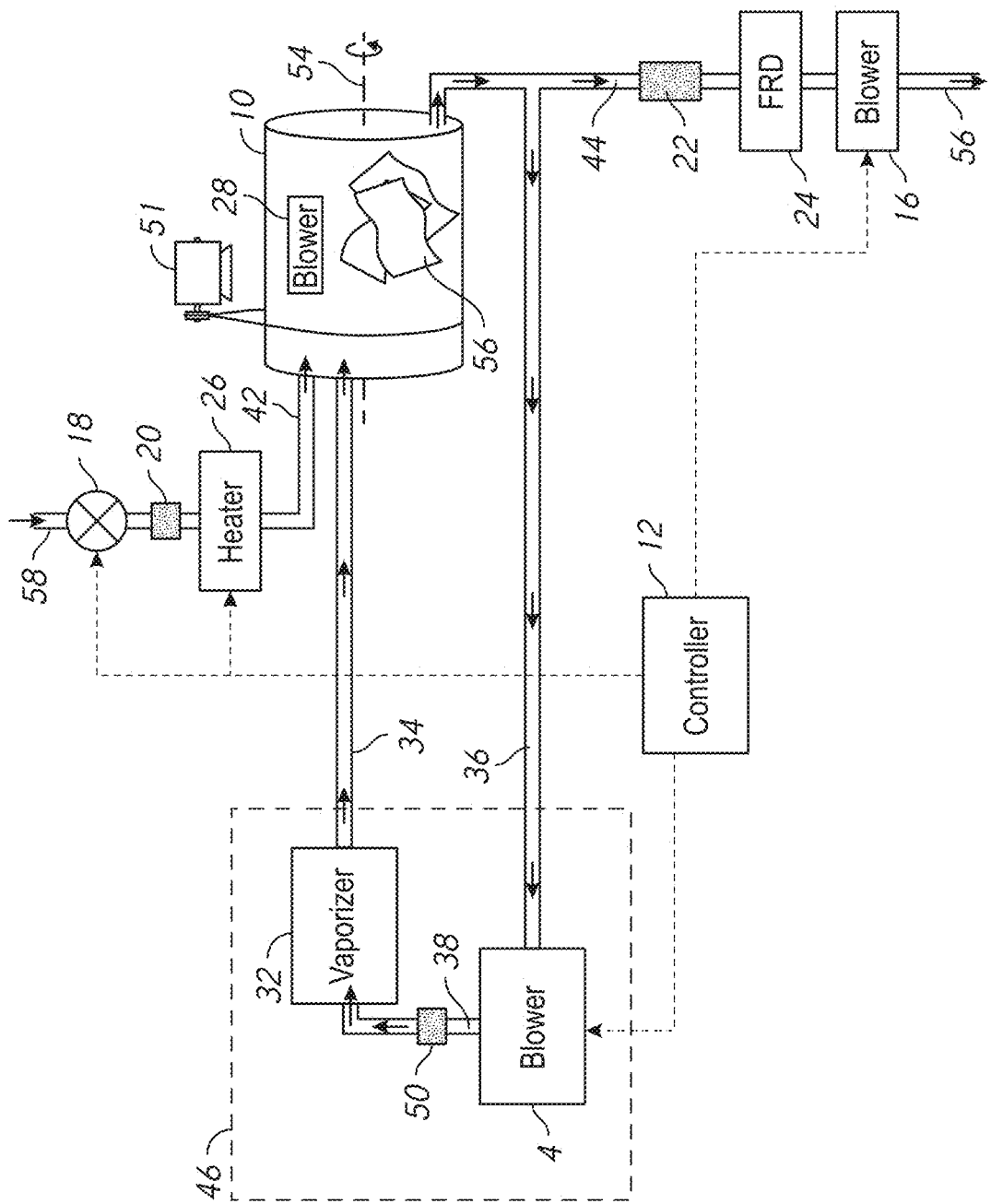
FIG. 5 shows a block diagram of a variation on the embodiment of FIG. 1, omitting the distributor and plasma generator.

As shown in FIGS. 4 and 5, in two additional embodiments, the effluent generator 46 could be made with only one of the sources—either a plasma generator 30 (FIG. 4) or a vaporizer (FIG. 5). In these variations, the blower/distributor 14 from FIG. 1A is replaced by a blower 4, since with only one source there is no need for distribution. However, in several embodiments, a blower distributor may still be used, in order to generate modular systems that can be varied between use of plasma or vapor at one point, and plasma and vapor at another point.

In the embodiment depicted in FIG. 4, the open loop pre-heater system with its heater 26, filter 20 and valve 18 is omitted as well, to illustrate a variation where there is no pre-heat capability.

It will be understood that these variations could also be applied to any of the other embodiments disclosed herein, although this is not explicitly illustrated in a figure.

In either of the variations, and in many of the embodiments, the sterilizer of certain embodiments operates in the closed-loop mode by recirculating the effluent through the chamber and the effluent generator without passing the effluent through a free-radical destroyer in the closed loop. In addition, the variations can control moisture levels as described herein with respect to FIG. 1A. In addition, regarding the embodiment shown in FIG. 5, as described herein with respect to FIG. 1A, evaporation can occur passively (e.g., without heat) by the flow of air through a wet wicking material.

Alternative Embodiment—Another Chamber with Both Plasma and Vapor

Figure 2:
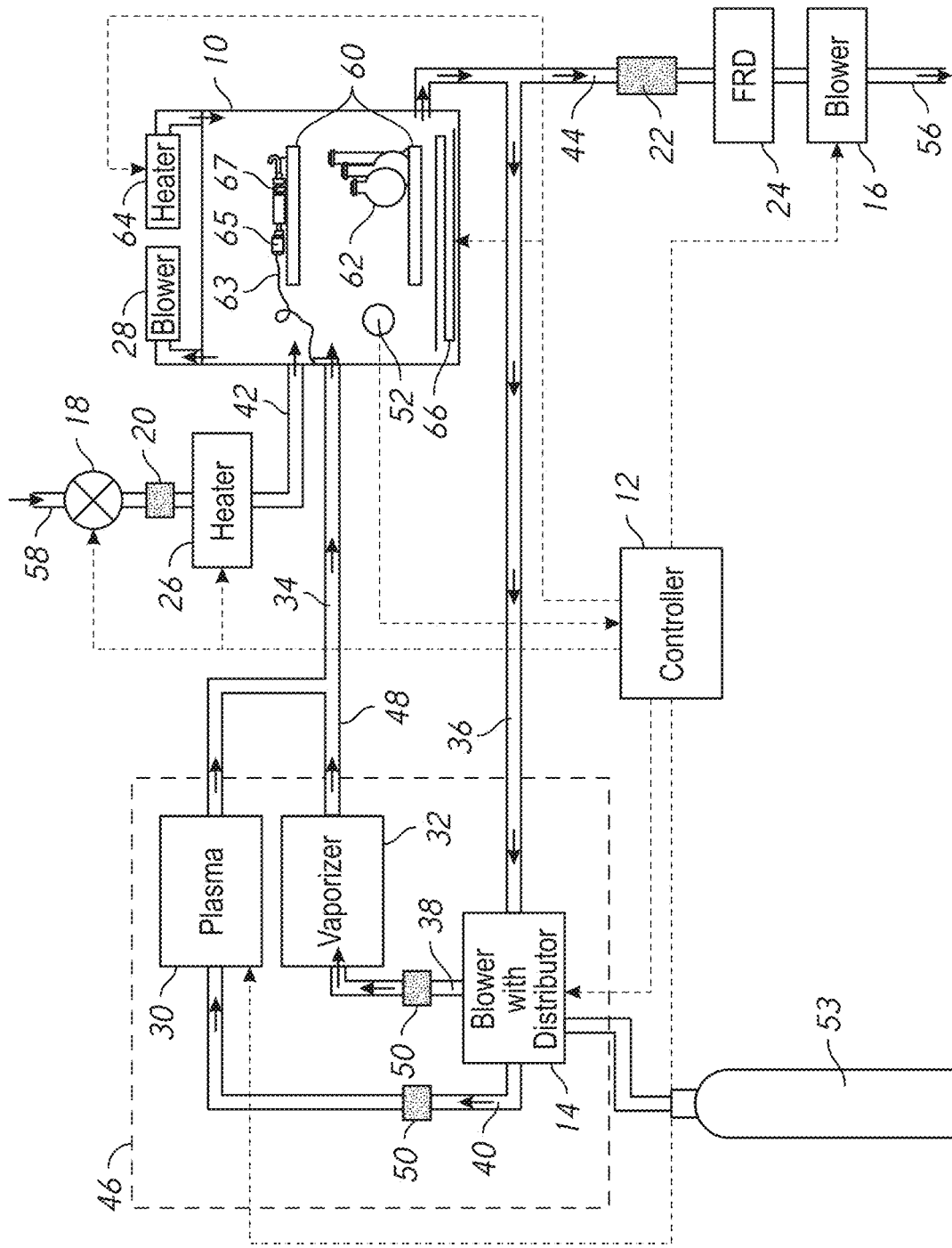
FIG. 2 shows a block diagram of a second embodiment of the disclosure with a stationary chamber with heating.

FIG. 2 illustrates an embodiment appropriate for more rigid items 62, such as laboratory glassware, surgical implements, dental tools, etc. The items 62 may be put on shelves 60, the shelves preferably being made of wire or perforated to allow free circulation of effluent around the items 62.

For the sterilization of instruments with internal conduits or lumens such as endoscopes, catheters, or dental handpieces 67, a portion of the sterilant gas can be forced through the instruments 67, while the outer surfaces of the instruments 67 are sterilized by the effluent in the chamber, as discussed below. To do this, one or more additional conduits can be supplied with sterilant gas from the effluent input conduit 34—this is shown in FIG. 2 as tubing (e.g., a flexible hose 63). The hose 63 is equipped with one or more appropriate adapters and/or connectors 65 to plug into the handpiece 67. The tubing can be made of any material, e.g., a material that is resistant to free radicals and/or reactive species (e.g., of hydrogen peroxide). For example, in some embodiments, the tubing can be made of Tygon®, Teflon®, and or polyvinyl chloride. In some other embodiments, the tubing can be made of any material having an inner coating or sleeve of such resistant material.

Additionally a circulating blower 28 can be used to increase effluent turbulence in the chamber. The blower 28 can be placed in the chamber 10, as shown in FIG. 1A, or outside, connected to the chamber by ducts, as shown in FIG. 2. As described herein, various embodiments can be used at ambient temperature. Optionally, a heater 64 can be put in the ducts to heat the air circulated by the blower 28, or, alternatively, the chamber may be directly heated by elements 66 either in the chamber or attached to the walls of the chamber. A heater can be used in any of the embodiments described herein although not shown in the figures.

In the embodiment of FIG. 2, a sensor (e.g., a temperature sensor 52) is provided in the chamber 10. The controller 12 can then maintain a selected temperature in the chamber 10 by reading the temperature through sensor 52 and controlling chamber heaters 64 and/or 66 as needed. Other sensors (e.g., pressure, humidity, etc.) can also be used.

Optionally, a carrier gas 53, such as air, oxygen, nitrogen, carbon dioxide, helium, argon, or a combination of carrier gases, can be introduced into the effluent generator 46 to be mixed with the effluent in the closed system. This can be done as an additional input to blower/distributor 14, as shown in FIG. 2.

Additional Systems and Devices Using Centrifugal Multiple-Outlet Blower

Figure 6:
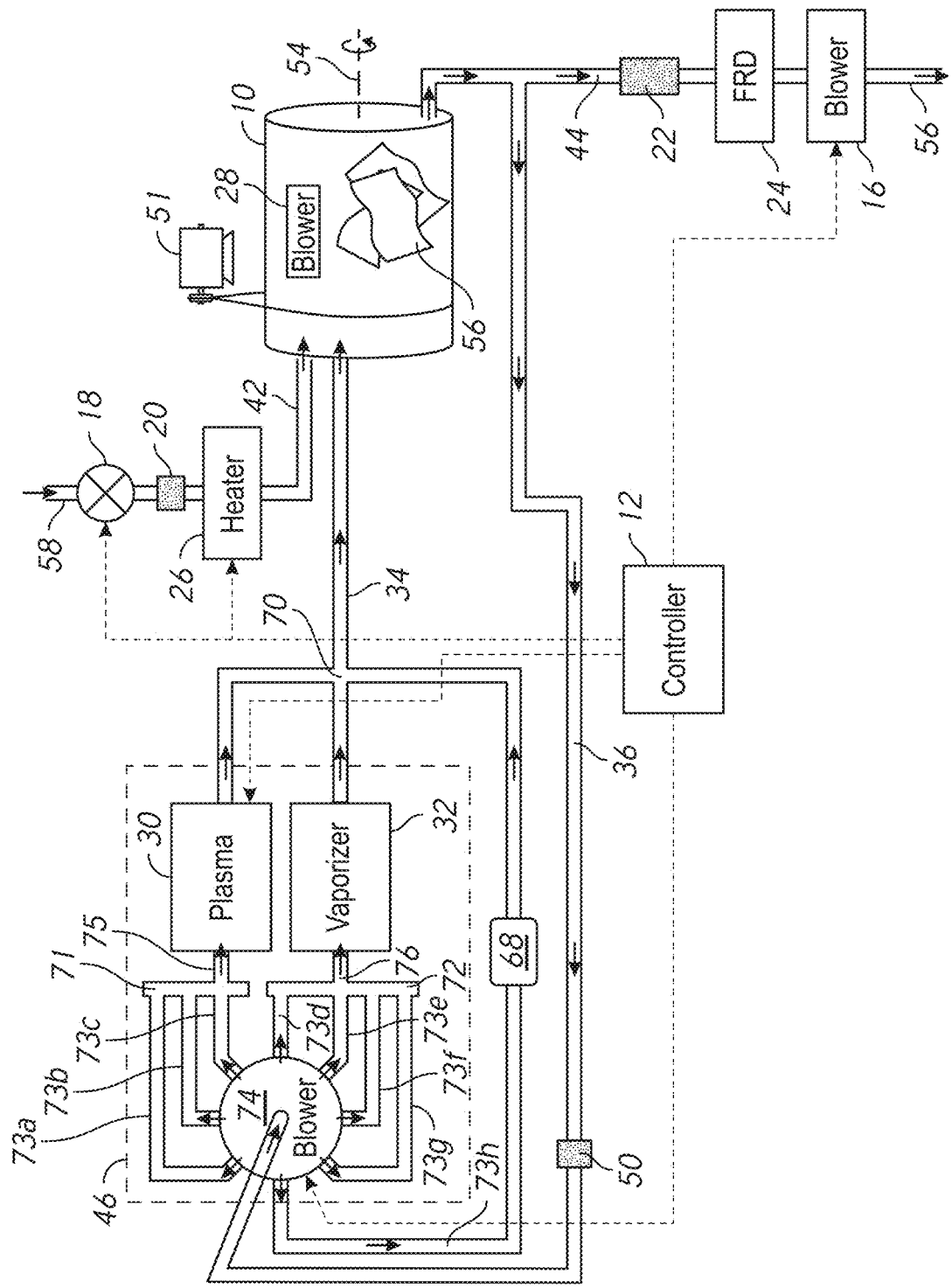
FIG. 6 shows a block diagram of a third embodiment of the disclosure, using a centrifugal multiple-outlet blower in place of the blower-distributor and adding a bypass heater.
Figure 7:
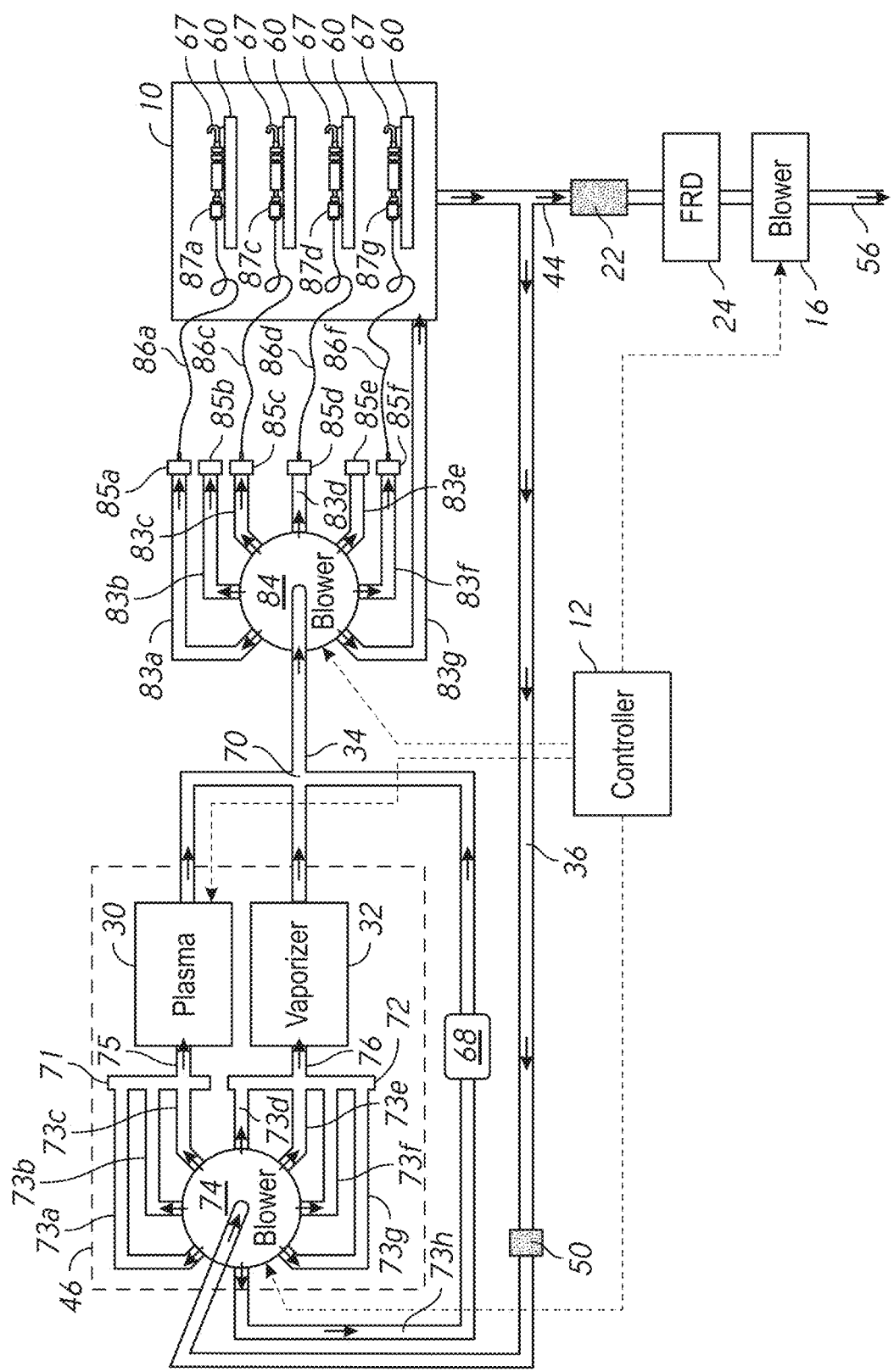
FIG. 7 shows a variation on the embodiment of FIG. 6, using two centrifugal multiple-outlet blowers to provide multiple outlets for recirculation.
Figure 8:
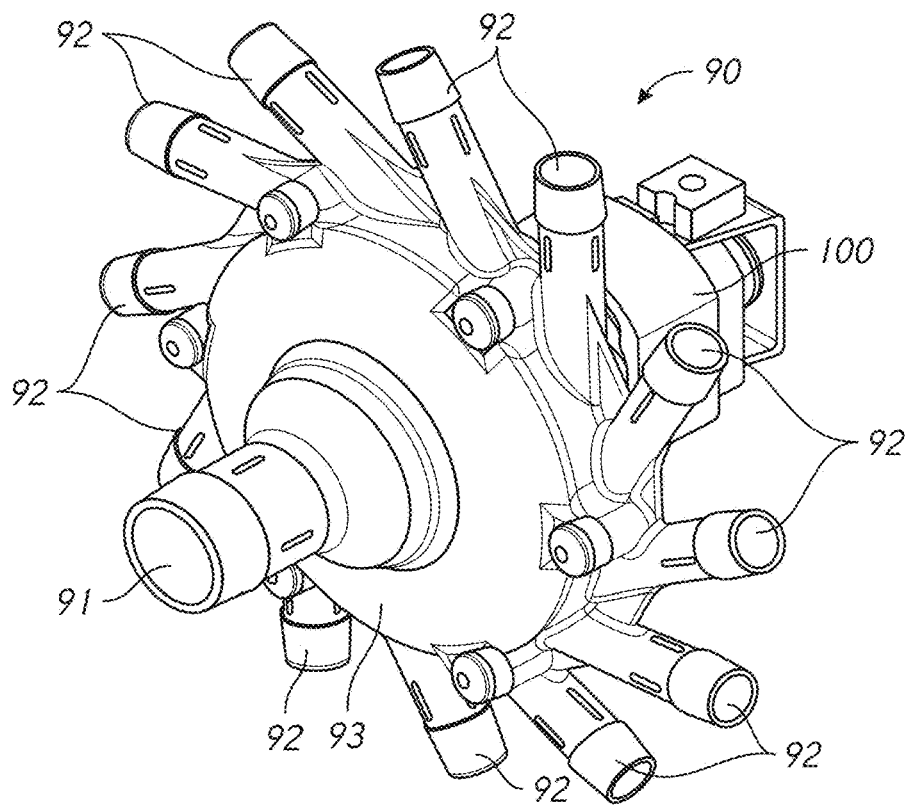
FIG. 8 shows a centrifugal multiple outlet blower as used in the embodiment of FIGS. 6 and 7.
Figure 9:
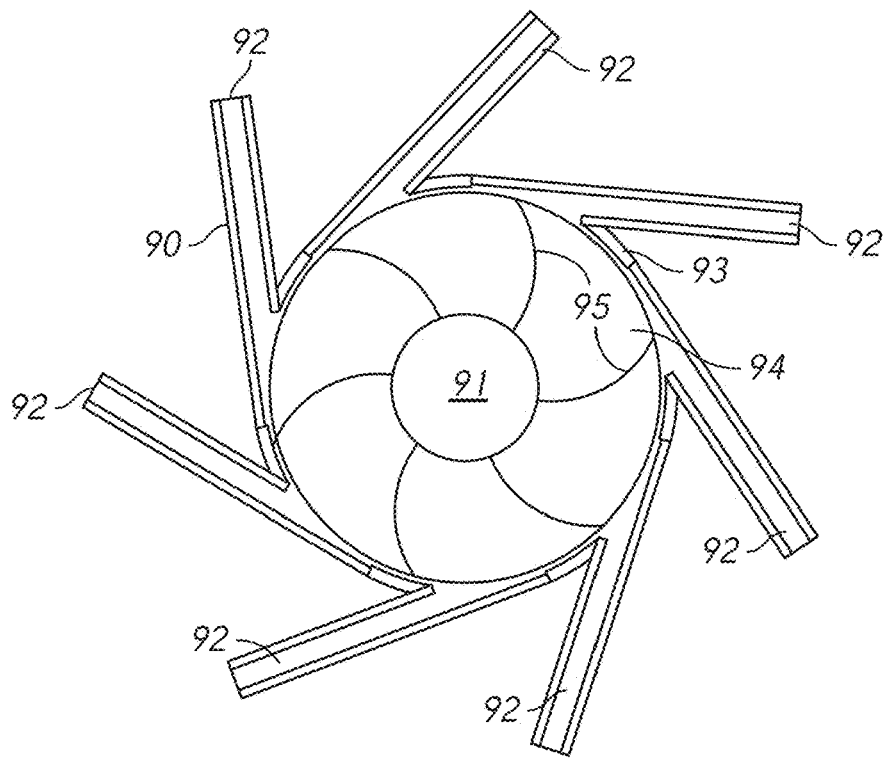
FIG. 9 shows a cut-away diagram of the blower of FIG. 8.

FIGS. 8 and 9 show a multiple-output centrifugal blower which is used with the embodiments as shown in FIGS. 6 and 7. The centrifugal blower used in this embodiment is a novel development on the centrifugal blowers and "squirrel-cage" type blowers.

As can be seen in FIGS. 8 and 9, the blower 90 has a central input 91 for drawing gas to be distributed by the blower 90 into the blower housing 93. A plurality of tangential outputs 92 are provided, each output providing a stream of gas in approximately equal amounts. The number of outputs 92 can vary within the teachings of the disclosure, depending on the requirements of the design. As examples, twelve outputs are shown in FIG. 8 and seven in FIG. 9, while blower 74 in FIGS. 6 and 7 has eight outputs and blower 84 has seven outputs. Other embodiments can employ alternative numbers of inputs and/or outputs.

A central impeller 94 inside the housing 93 is rotated by a conventional motor 100. The motor can be electric, or powered by hydraulic fluid or compressed air, or any other motive force known to the art. The impeller 94 is here shown as centrifugal impeller" type, which has a plurality of curved blades 95. As the impeller 94 is rotated at high speed, air from input 91 is flung outward by centrifugal force and the action of the blades 95, and is expelled through tangential outputs 92. In some embodiments, the impeller 94 may be designed with plastic, but other materials may be used, e.g., non-reactive metals, etc.

FIG. 6 shows how a multiple-output blower can be used within the teachings of the disclosure as the blower-distributor 14 of FIG. 1A.

In this embodiment, the effluent generator 46 uses multiple-output blower 74 to apportion the effluent returning from chamber 10 through conduit 36 between the plasma generator 30, the vaporizer 32, and an optional bypass heater 68. The outputs of the plasma generator 30, vaporizer 32 and bypass heater 68 are combined together at a junction 70, the combined effluent streams flowing into the chamber 10 through conduit 34 as in previous figures.

The outputs 73a-73h of the blower 74 each carry an output flow which is a fraction of the total output flow of the blower approximately equal to the total flow divided by the number of outlets. Therefore a desired portion of the effluent can be chosen by combining an appropriate choice of the number of outputs, with the output of the manifold being approximately equal to the number of blower outputs being combined divided by the total number of outlets available. Multiple outputs can be combined using manifolds, such as manifold 71 to which outputs 73a-73c are input, or manifold 72 which combines the flow from outputs 73d-73g. Output 73h is connected directly to the bypass heater 68.

In the example of FIG. 6, blower 74 has eight outputs 73a-73h, so each output carries approximately one eighth or 12.5% of the total output of the blower. Therefore, in the arrangement of this example, manifold 71 receives three eighths (37.5%) of the flow, and the output of the manifold feeds this flow to plasma generator 30 through conduit 75. Similarly, manifold 72 receives four eighths (or one half) (50%) of the flow through conduit 76, the output of which is connected to vaporizer 32. Bypass heater 68 receives one eighth (12.5%) of the flow directly from a single output 73h, which could be thought of as a manifold with a single input. Other proportions between the plasma generator 30, vaporizer 32, and/or bypass heater 68 are possible.

FIG. 7 shows the third embodiment used with a fixed chamber for sterilizing items such as endoscopes, catheters, or dental handpieces 67 (or other medical tools having lumens or other interior conduits or spaces which should be sterilized), as in the second embodiment of FIG. 2. Shelves 60 can be provided to support the tools 67, as needed.

In FIG. 7, rather than feeding the chamber 10 directly, the effluent conduit 34 is used to feed a second multiple-outlet centrifugal blower 84. In this variation, the multiple outputs 83a-83g of blower 84 are used individually to feed multiple users of the effluent, rather than being combined to apportion flow as with outputs 73a-73h of blower 74.

The outputs 83a-83f of blower 84 are fitted with shut-off valves or quick-disconnect fittings 85a-85f, of any kind known to the art. Flexible hoses 86a-86f are plugged into fittings 85a-85f to conveys effluent from the fittings 85a-85f to connectors or adaptors 87a-87f, into which the handpieces 67 can be plugged to sterilize the insides of the handpieces. Output 83g of blower 84 is routed directly to chamber 10, to supply effluent to the chamber for sterilizing the outside of the handpieces 67, as well as any other contents of the chamber.

In other embodiments, the outputs 83a-83f of blower 84 can be fed directly into the chamber 10 with the hoses 86a-86f connected inside the chamber 10. In some such instances, the chamber 10 may be separated into multiple chambers such that it may be possible to adjust and/or remove one item from within the chamber 10 without affecting another item within the chamber 10. As another example, some embodiments may include a separate exiting rigid or flexible chamber such that one of the items can be conveyed to the exiting chamber prior to removal without affecting another item within the chamber 10.

Some embodiments may incorporate quality control and/or regulatory compliance indicators. For example, some embodiments may provide an indicator (e.g., disposable, semi-disposable, or non-disposable) on the shelf 60 for each item (e.g., instrument 67). As another example, some embodiments may provide a removable holder for each separate item with the indicator place within or on the holder. The holder can be placed within the chamber 10 and connected accordingly. In some such embodiments, each item can have its own indicator and traveling container. Other examples are possible.

Systems and Devices Employing a Wound Chamber

Figure 10:
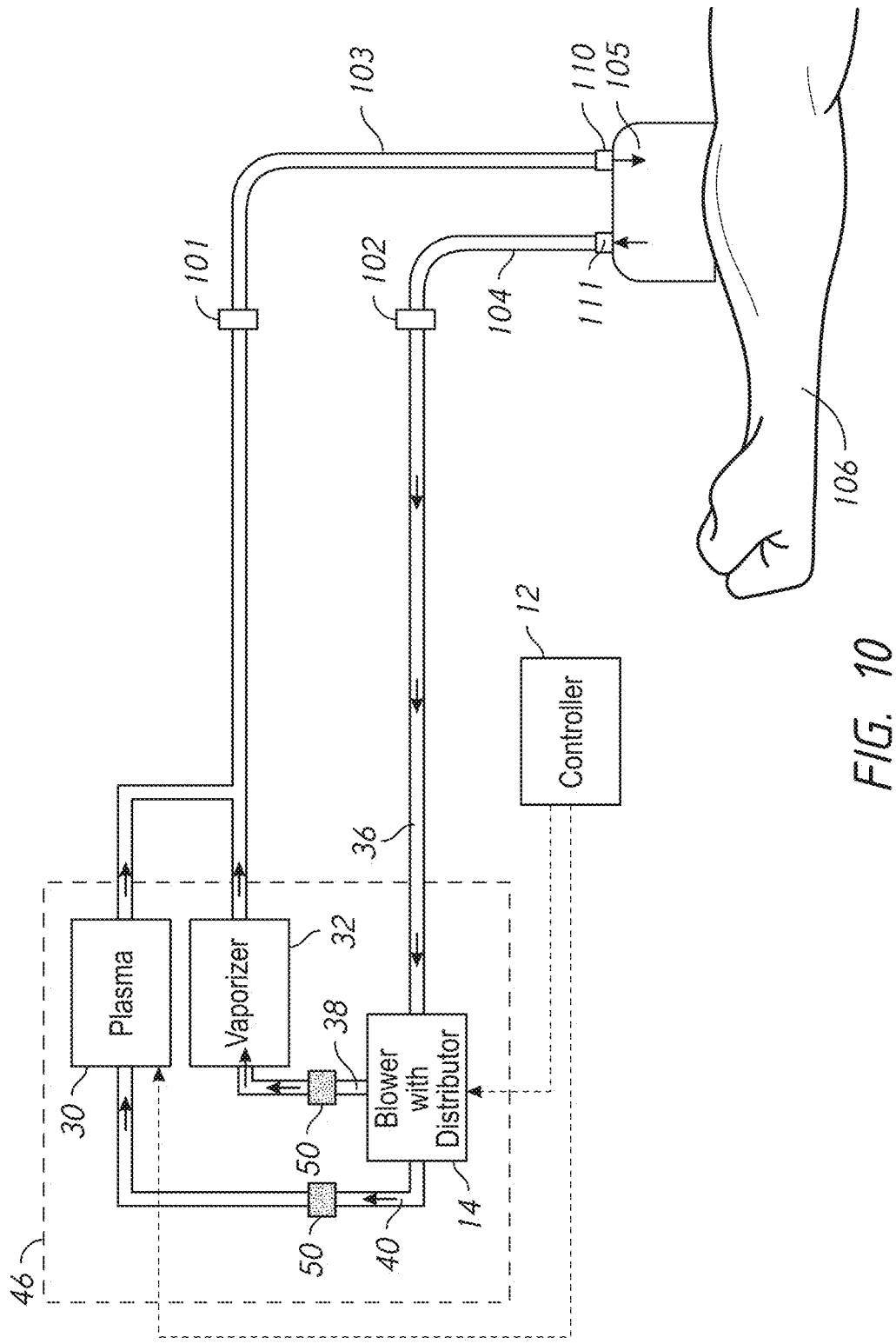
FIG. 10 shows a fourth embodiment of the disclosure, showing use with a wound chamber.
Figure 11:
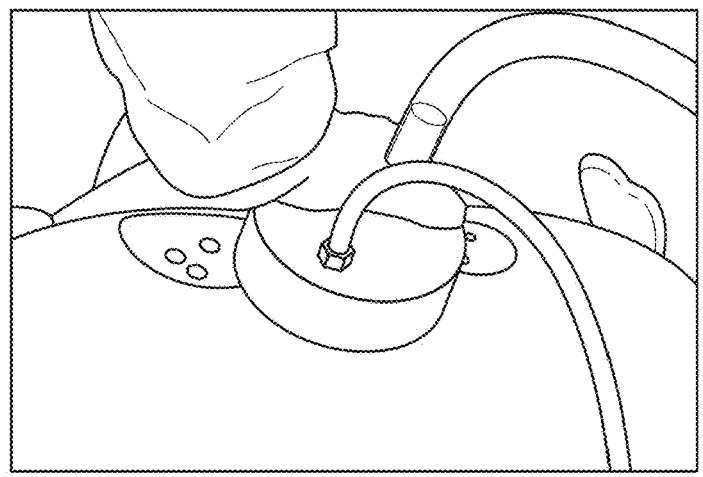
FIG. 11 shows a picture of a wound chamber in use.
Figure 12:
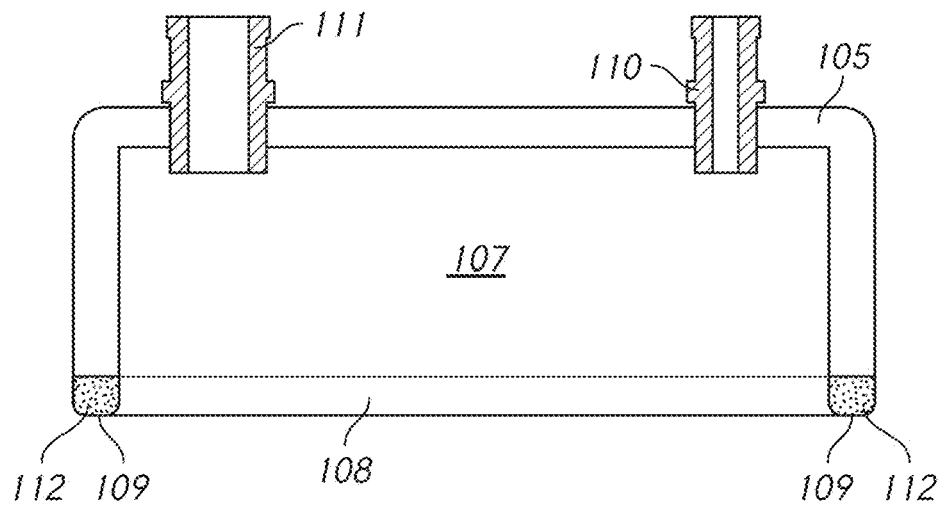
FIG. 12 shows a cut-through side view of a wound chamber.

FIGS. 10-12 show how certain embodiments can be used with an open-sided portable wound chamber 105 to apply effluent to an open wound on a patient. Such application has been shown in experiments to promote healing.

FIG. 10 shows how the system of some embodiments is used in this application. Effluent generator 46 recirculates effluent from conduit 36 to conduit 34, as described in the preceding embodiments. It will be understood that while the effluent generator 46 is shown in FIG. 10 in the version used in FIGS. 1A and 2, the effluent generator 46 could also be any of the other versions described herein or in application Ser. No. 12/510,341 (now U.S. Pat. No. 8,221,679), incorporated herein by reference. If desired, plasma generator 30 or vaporizer 32 may be omitted. In various arrangements, medication or other treatment may be added to the circulating sterilant.

The wound chamber 105 is shown in FIG. 12 in a sectional view. The chamber 105 has a body 107 with an open bottom 108. The edges 109 around the open bottom 108 can be simply rounded off, or could be provided with flexible or resilient sealing material 112 to facilitate a tight seal against a surface. Connectors 110 and 111 provide mechanisms for connecting input and output hoses, respectively, to route the flow of effluent to and from the chamber. The connectors could be the same size, or, as shown in FIG. 12, the input connector 110 could be of smaller diameter than the output connector 111.

In this embodiment, the output conduit 34 of the effluent generator feeds a wound chamber 105 through a flexible hose 103 which connects to appropriate connectors 101 and 110 at each end. Return effluent from the wound chamber 105 passes through flexible hose 104 with connectors 102 and 111 into return conduit 36, to be recirculated back through the effluent generator 46. In use, the chamber 105 is placed upon the body of the patient (here shown as an arm 106), over the wound to be treated. The chamber 105 is pressed firmly against the body 106, and the sterilizer is operated for a selected period of time.

Figure 14:
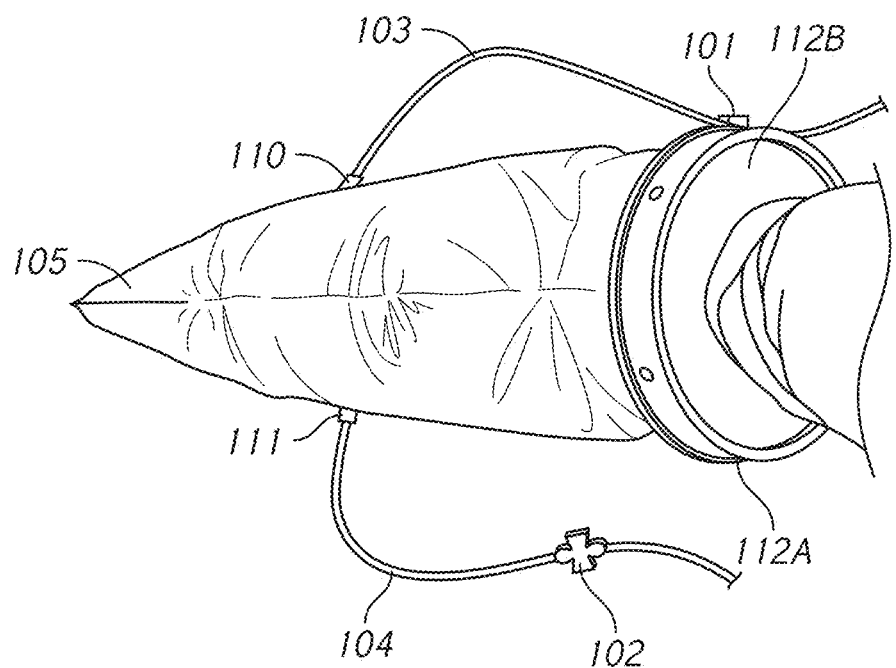
FIG. 14 shows a picture of an example inflatable wound chamber in use.
Figure 15:
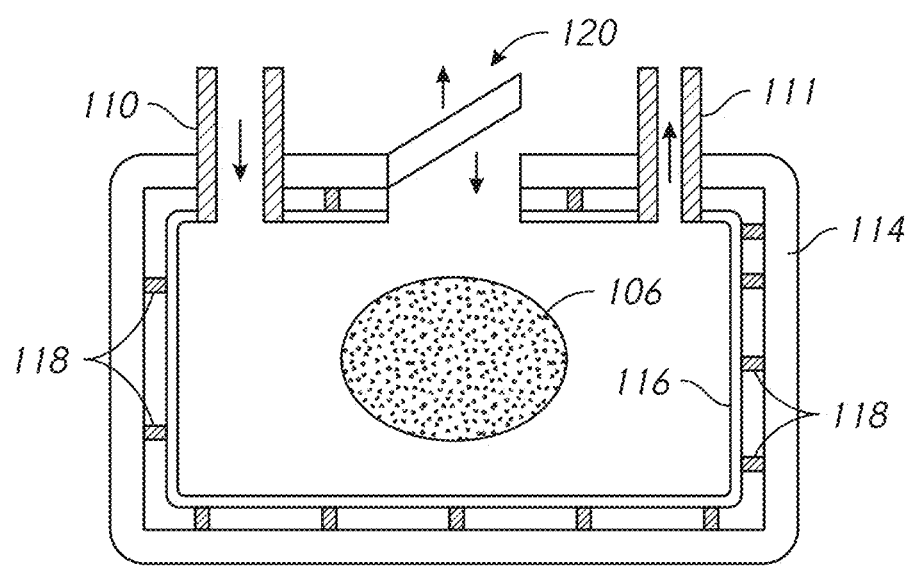
FIG. 15 shows a cross-sectional view of an example wound chamber that includes structures configured to maintain separation between the wound chamber and the patient.

As shown in FIGS. 14 and 15, the wound chamber 105 may be designed to maintain separation from the patient's wound(s). In a first arrangement, the wound chamber 105 may be filled with circulating sterilant at a positive pressure, thereby inflating the wound chamber 105. Wound chamber 105 may include structures as collar 112A and cuff 112B that enable chamber 105 to be placed over a limb and sealed to the limb. In general, any suitable mechanisms for sealing the wound chamber 105 to a patient may be used. Examples of such suitable mechanisms include flexible cuffs, tape, straps, zippers, snaps, clips, buttons, and other mechanical implementations. Similar mechanisms may also be used to provide access to the patient's wound during, before, or after treatment, as shown by access port 120 in FIG. 15. Access ports such as access port 120 may be provided for the placement of a sensor inside of chamber 105 (e.g., to provide sealed pathways for cabling to and from such sensor) and to provide medical providers with access to the patient's wounds for any purpose.

The wound chamber, sealing mechanism, and associated hoses, couplings, and accessories may be formed from any suitable materials. In general, materials that come into contact with the sterilant should be safe to contain the sterilant and materials that come into contact with patients should be biocompatible. While FIG. 14 illustrates wound chamber 105 sized for a patient's arm, wound chamber 105 may be provided in alternative forms sized for patients of different sizes and ages, a patient's leg, a chest, or even an entire body (with an opening enabling the patient to breathe).

As shown in FIG. 14, wound chamber 105 may include structures that provide rigidity to the wound chamber. Such structures may, in some arrangements, enable wound chamber to be operated at a slightly negative pressure, while still maintaining separation from the patient's wound and enabling the free circulation of sterilant. Operating chamber 105 at a slightly negative pressure has an added benefit of reducing the likelihood of the circulating sterilant escaping into the surrounding atmosphere, which may, as an example, increase the safety of chamber 105 in situations in which the sterilant is hazardous, perhaps when inhaled. These structures may include, as a first example, ribs 118 which may be rigid or inflatable. As a second example, these structures may include a two-chamber design including outer wall 114 and inner wall 116 where the space between the walls may be pressurized to form a rigid shell. Even when wound chamber 105 is operated at a positive pressure, wound chamber 105 may include any of the features described herein that provide rigidity.

Figure 21:
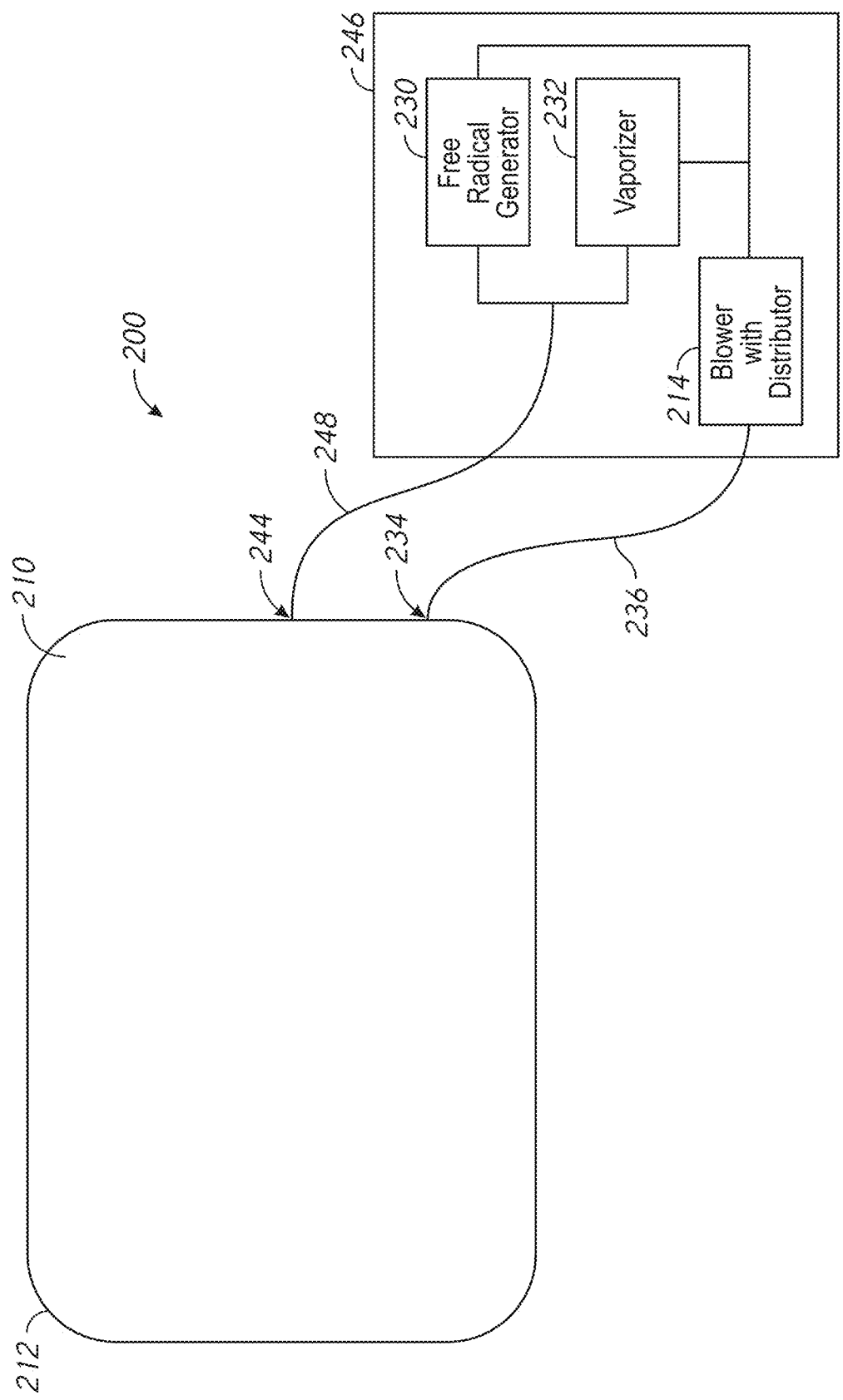
FIG. 21 shows another embodiment of the system for sterilization and disinfection.

FIG. 21 illustrates another embodiment of the system for sterilization and disinfection 200. As with the examples provided above, the system for sterilization and disinfection 200 can include a chamber 210 that is fluidly connected to an effluent generator 246. In some embodiments, the chamber 210 can have an inlet 244 and an outlet 234 that are connected to the effluent generator 246 through an inlet conduit 248 and an outlet conduit 236 respectively to form a closed system. As discussed above, the effluent generator 246 can include a free radical generator 230, a vaporizer 232, and a blower with distributor 214.

Figure 22:
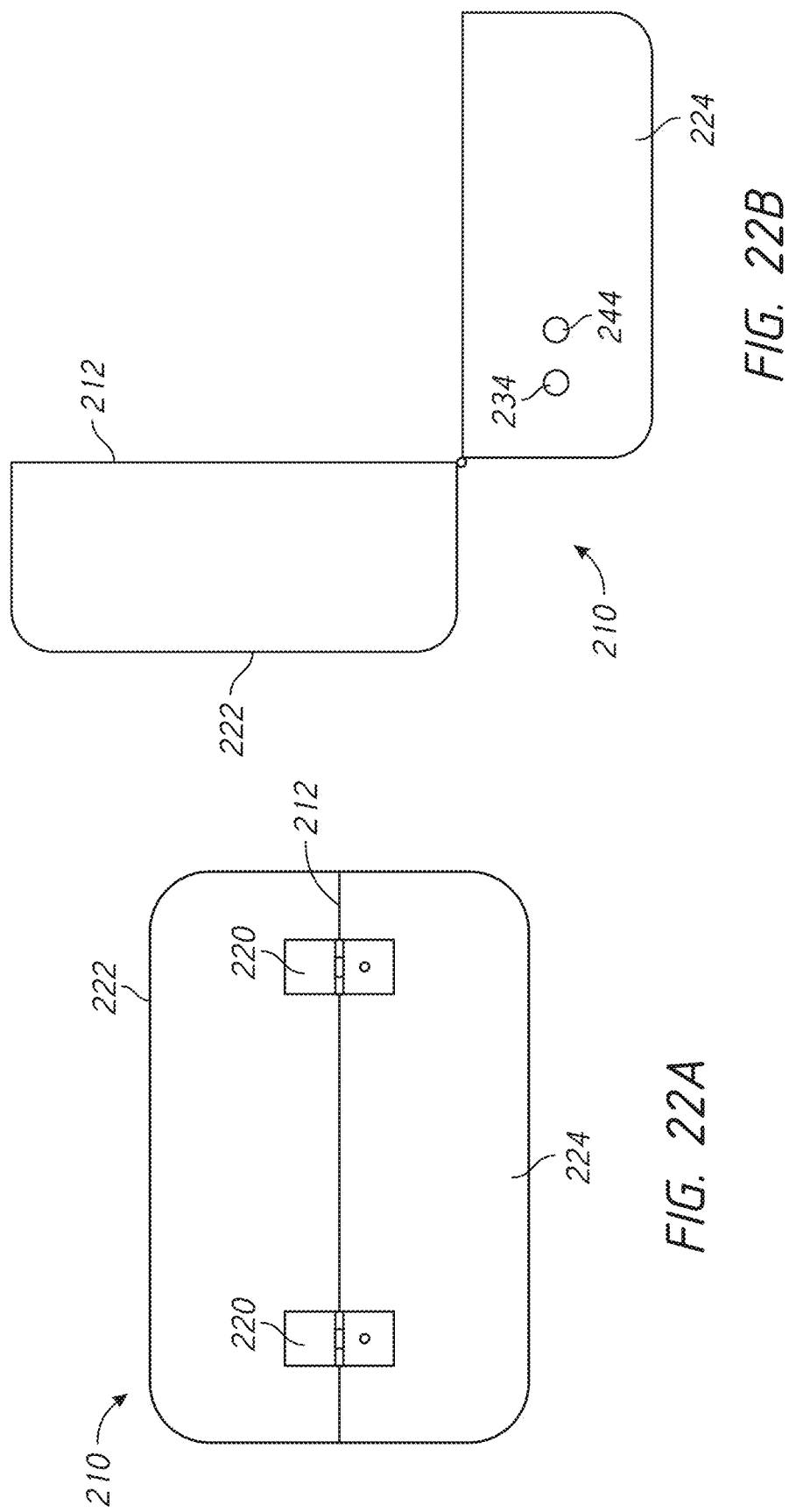
FIGS. 22A-22B shows a plurality of views of an embodiment of a chamber that can be used in a system for sterilization and disinfection.

The chamber 210 can be configured to receive sterilant and the item to be sterilized. As illustrated in FIG. 22A-B, the chamber 210 can be configured to receive and store an item before and after sterilization. In some examples, the chamber 210 can include a top portion 222 and a bottom portion 224 that can be opened and closed to secure an item to be sterilized within. In some embodiments, the top portion 222 and the bottom portion 224 are configured to form a seal 212 when closed. As well, the chamber 210 can include engagement structures 220 that are configured to secure the top portion 222 with the bottom portion 224 such that the interior of the chamber 210 remains sterilized and disinfected. In some embodiments, the engagement structure 220 can be a clasp, a lock, or any other structure that can secure the two halves of the chamber 210. In some examples, the inlet 244 and the outlet 234 are located on the exterior of the chamber 210 to allow sterilant to be received and circulated into and out of the chamber 210.

The chamber 210 may be made of any type of material, such as a non-conductive material to prevent interference with certain reactive species of the sterilant. For example, the chamber 210 can be made of glass, plastic (e.g., polytetrafluoroethylene), or combinations thereof (e.g., partially glass and partially plastic). In some embodiments, the chamber 210 may be transparent or partially transparent such that the contents within the chamber 210 may be viewable during the sterilization process.

As illustrated, the size and shape of the chamber 210 are not particularly limited, but can be tailored to the application of use. For example, in some instances, the chamber 210 may be relatively small, light-weight, and portable. In other embodiments, the chamber may be dimensioned to accommodate larger items, such as control modules for IV stands, power units for various equipment in surgical suites, end piece apparatuses used in an operating room (such as eyepieces for surgical scopes).

Figure 23:
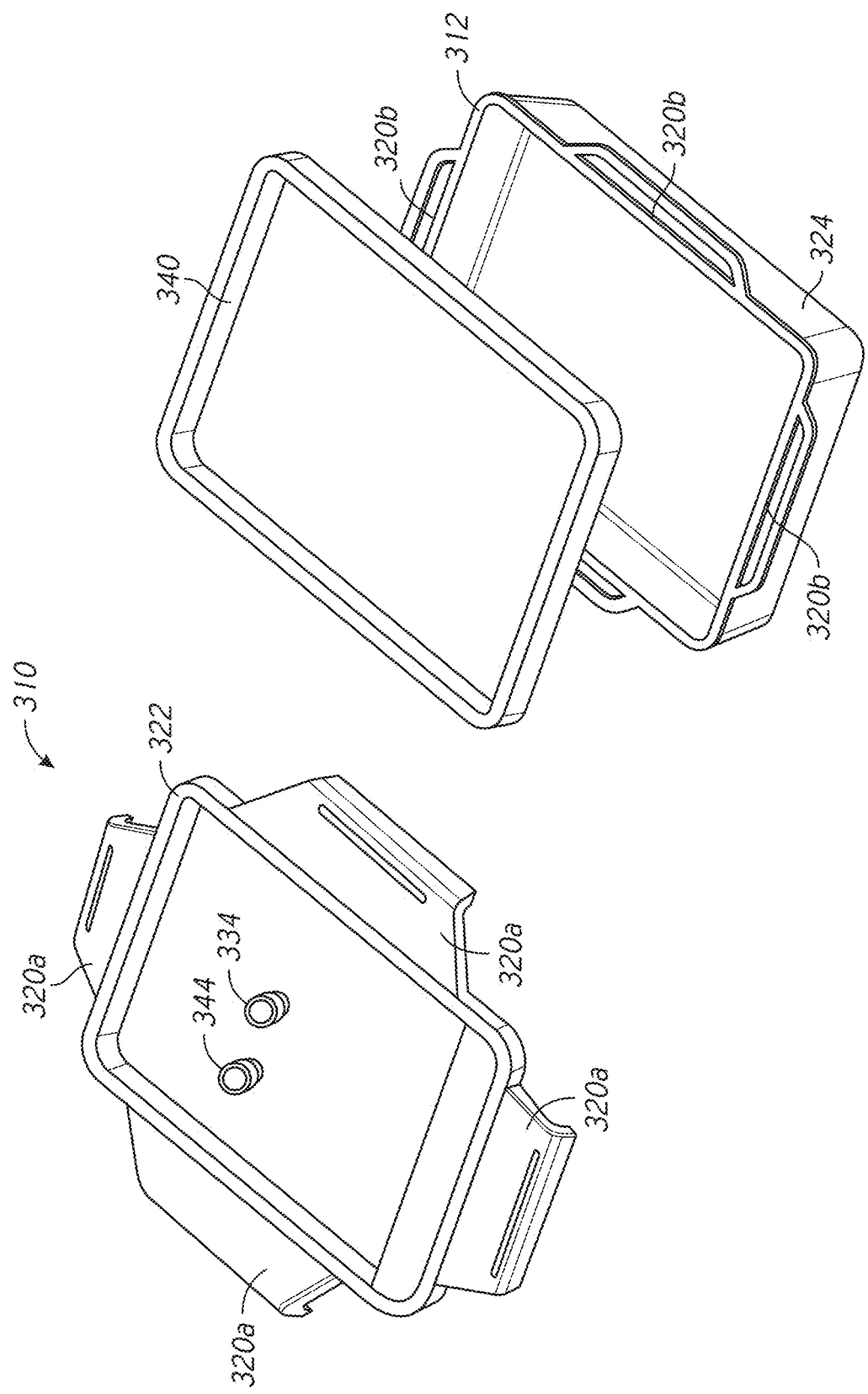
FIG. 23 shows an exploded view of an embodiment of a chamber including an insert that can be used in a system for sterilization and disinfection.

In some embodiments, the chamber can include a container of custom size and shape based on the device or devices to be placed inside the container for sterilization, disinfection, sanitation, and/or decontamination. FIG. 23 illustrates an embodiment of the chamber 310 further including an insert 340. The disclosed insert 340 can be used in any of the chambers disclosed above. The chamber 310 can include a top portion 322 and a bottom portion 324 that are configured to receive the insert 340. The top portion 322 of the chamber 310 can include a plurality of engagement structures 320a that are configured to engage with the plurality of engagement structures 320b of the bottom portion 324. In some examples, when the plurality of engagement structures 320a are secured with the plurality of engagement structures 320b, a seal 312 can be formed between the top portion 322, bottom portion 324 to secure and seal the insert 340 located within. In some embodiments the top portion 322 further includes an inlet 344 and an outlet 334. The outlet 334 and the inlet 344 are located on the top portion 322 such that sterilant can be circulated about the devices placed in the insert 340. However, the outlet 334 and the inlet 344 can be located anywhere on the chamber 310—whether on the top portion 322 or the bottom portion 324.

Figure 24:
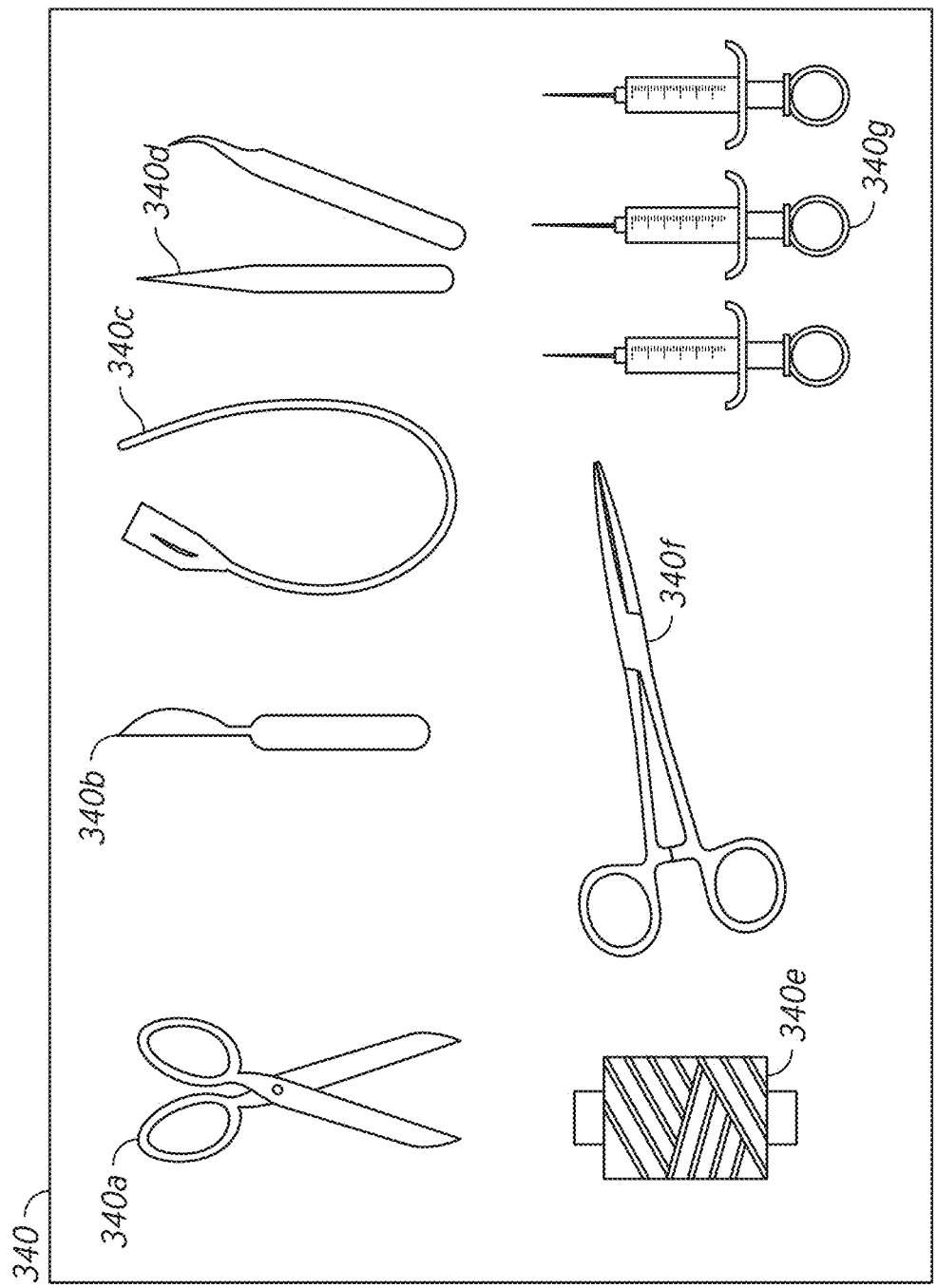
FIG. 24 shows an embodiment of an inset to be used in a chamber.

In some embodiments, the insert 340 can be configured to provide a custom sized fit for receiving a plurality of devices. For example, the insert 340 inside chamber 310 can contain recesses shaped to hold each of a plurality of devices. FIG. 24 illustrates an example of an insert 340 configured to receive and secure a plurality of devices for sterilization/disinfection. This can include, for example, a sterile kit that includes a plurality of items such as a first item 340a (e.g. scissors), a second item 340b (e.g. scalpel), a third item 340c (e.g. catheter), a fourth item 340d (e.g. forceps), a fifth item 340e (e.g. suture), a sixth item 340f (e.g. hemostat), and a seventh item 340g (e.g. syringes).

The insert 340 can allow an item to be packaged, sterilized and/or disinfected and then transported, all the while remaining sterilized and/or disinfected prior to use. Particularly in the field of medical devices, the configuration of the system for sterilization and disinfection 300 with insert 340 can provide for easy packaging of an item to be used during a surgical procedure (e.g. a medical device or a medical kit) and easy sterilization/disinfection thereafter. Once packaged, the item, through the inlet 344 and the outlet 334, can be sterilized and/or disinfected and subsequently stored until ready for use. The seal 312 of the chamber 310 can ensure that the item within the chamber 310 remains sterilized and/or disinfected during storage and transportation. In this way, when the item is brought out for use in a sterile environment, the item does not need to be sterilized and/or disinfected again.

Figure 25A:
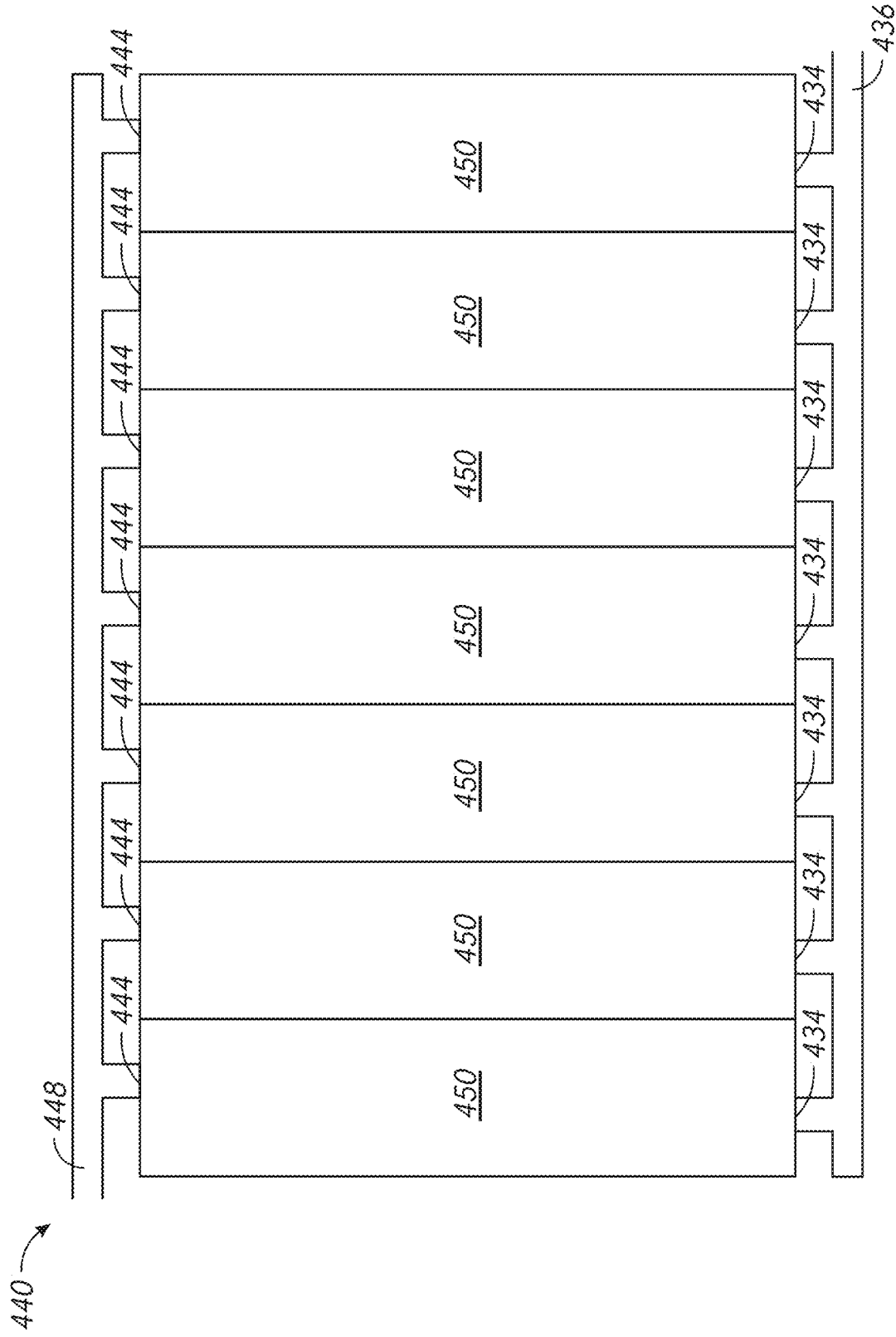
FIG. 25A-25B shows another embodiment of a chamber that can be used in a system for sterilization and disinfection.
Figure 25B:
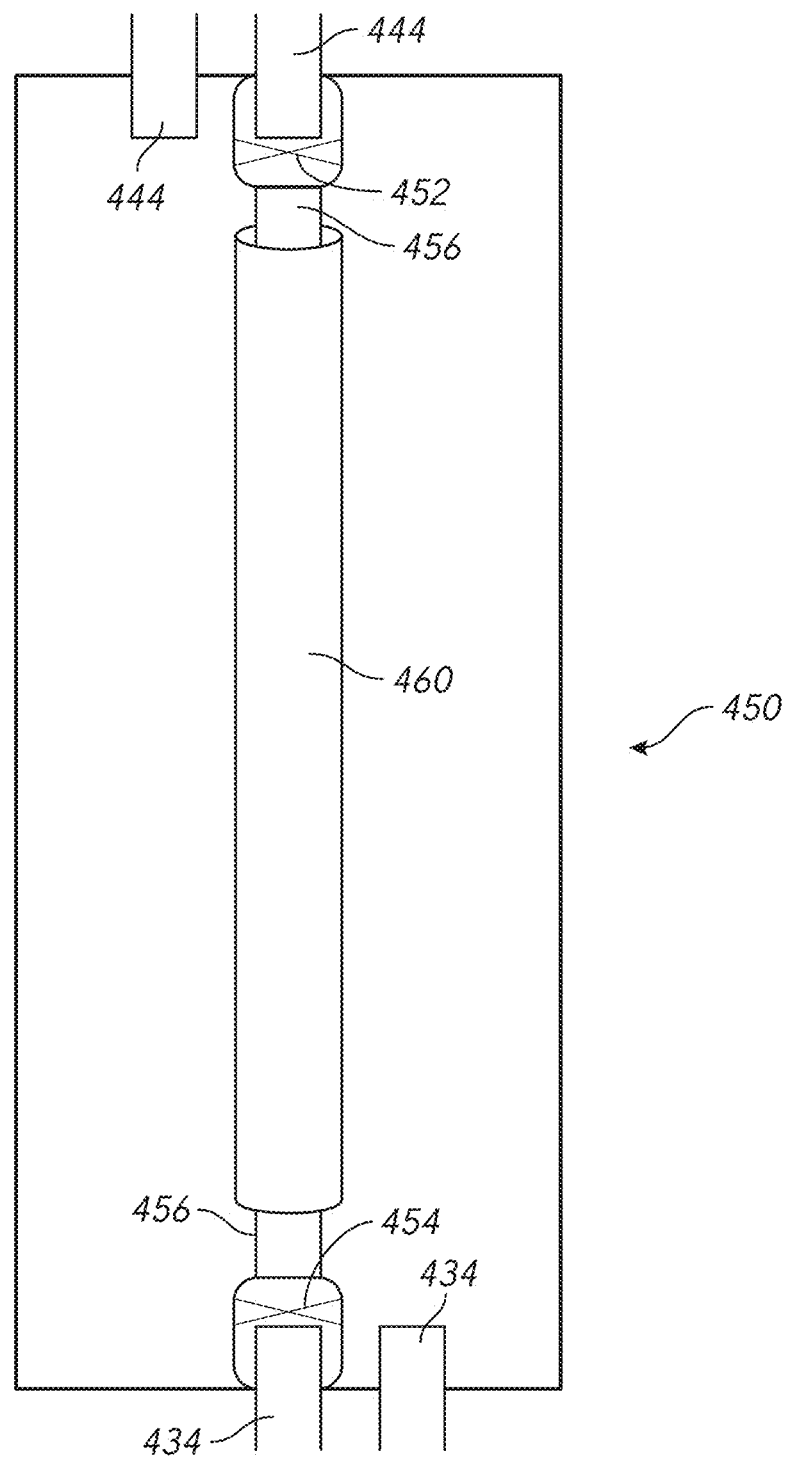

FIGS. 25A-25B illustrate another embodiment of the system for sterilization and disinfection 400 wherein the interior of the chamber 410 (not illustrated) includes a plurality of compartments 450. In some embodiments, each of the plurality of compartments 450 includes a plurality of inlets 444 and outlets 434. The plurality of inlets 444 can be fluidly connected by an inlet conduit 448 such that sterilant can be provided to all of the plurality of compartments 450 at the same time. Similarly, in some examples, the plurality of outlets 434 can be fluidly connected by an outlet conduit 436 such that sterilant can be circulated out of the plurality of compartments 450 at the same time. In other embodiments, the flow of sterilant into and out of each of the plurality of compartments 450 can occur independently of the remaining plurality of compartments 450. In some examples, each of the plurality of compartments 450 are removable and/or insertable and includes individual seals such that each of the plurality of compartments 450 remains sterilized/disinfected even when removed from the chamber 410 of the system for sterilization and disinfection 400.

FIG. 25B illustrates a cross-section of an embodiment of an individual compartment of the plurality of compartments 450. In some embodiments, the plurality of compartments 450 is configured with a plurality of inlets 444 and a plurality of outlets 434. This configuration can allow each of the plurality of compartments 450 to be dual purposed. For example, each of the plurality of compartments 450 can be configured to sterilize an interior of an item placed within the compartment 450 and anything located external to the item (e.g. the exterior of the item or a separate item placed in the compartment 450).

In some examples, the dual purposed sterilization/disinfection can be accomplished by including a sterilization lumen 456 having an inlet valve 452 and an outlet valve 454 that are attached with the inlet 444 and the outlet 434 respectively. In some embodiments the inlet valve 452 and the outlet valve 454 are duck bill valves that form attachment points between the inlet 444 and the outlet 434 and the sterilization lumen 456 disposed therein. In some examples, the inlet valve 452 and the outlet valve 454 are predisposed to be in a closed position such that attachment and removal of each of the plurality of compartments 450 from the system for sterilization and disinfection 400 does not allow air flow to disturb the sterility of the contents inside the container. Furthermore, in such embodiments the cracking pressure of the inlet valve 452 and the outlet valve 454 are high enough to prevent air flow in or out of the container.

As shown in FIG. 25B, the inlet valve 452, the outlet valve 454, and the sterilization lumen 456 allow for a device having a lumen 460 to be sterilized. The sterilization lumen 456 is configured to sterilize devices having tubular configurations (e.g. catheters) that have interior surfaces that are difficult to reach, clean, or sterilize/disinfect. In some embodiments, the sterilization lumen 456 can have a plurality of openings along the length of the sterilization lumen 456 such that sterilant can be circulated through the interior of the lumen of the device 460. In some embodiments the sterilization lumen 456 comprises a first half adjacent to the inlet valve 452 and a second half adjacent to the outlet valve 454. The first half of the sterilization lumen 456 can be received within a first end of the lumen of the device 460, while the second half of the sterilization lumen 456 can be received within a second end of the lumen of the device 460. Sterilant can therefore be received through the first end of the device having a lumen 460 and circulated out through the second half of the sterilization lumen 456.

In some embodiments, each of the plurality of compartments 450 are sterilized/disinfected by circulating sterilant through each of the inlets 444—sterilant is therefore circulated into the interior of the plurality of compartments 450 to both sterilize/disinfect the exterior of the device having a lumen 460 and the interior of the lumen of the device having a lumen 460. At the end of the cycle, the sterilant is circulated out of the plurality of compartments 450 through the outlet 434 and the outlet 434 adjacent to the outlet valve 454. Each of the plurality of compartments 450 can then be transported and stored—wherein the item located within each of the plurality of compartments 450 remains sterile/disinfected until use.

Use of the Sterilizer and Wound Chamber

FIG. 11 shows a photograph of the wound chamber in use in an experiment on a pig. In the example, multiple deep dermal partial thickness burn injuries were induced in Yorkshire pigs weighing 40-45 kilograms. After the burn wounds were produced, the wounds were inoculated with both *Staphylococcus aureus* and *Pseudomonas aeruginosa* to create a polymicrobial wound infection. These microorganisms were chosen as these two organisms are commonly found in infected burn wounds in humans.

Figure 13:
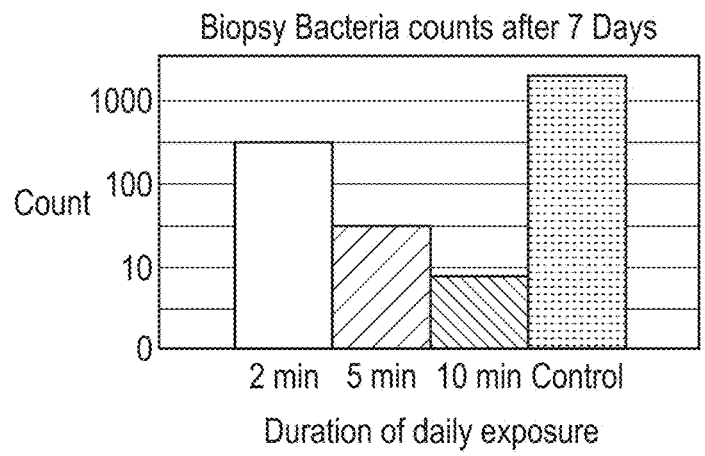
FIG. 13 shows a bar graph of results from a method of wound treatment using the fourth embodiment of the disclosure.

Burn wounds were exposed to disinfecting effluent produced by the sterilizer of the disclosure by placing the wound chamber over the wounds and operating the sterilizer for 2, 5 and 10 minutes each day for seven days. The wounds were examined on a daily basis. The results of the seventh day bacterial count compared with the control (not treated) are shown in FIG. 13, which has a logarithmic scale of bacteria count on the vertical axis, and bars along the horizontal axis showing counts in areas exposed for 2 minutes, 5 minutes and 10 minutes, as well as a bar showing counts in an untreated (control) area. As can be seen in this figure, the bacteria counts are significantly lower in areas treated using certain embodiments described herein—the ten-minute treatment count being more than 100 times smaller than the control.

Example Method of Operation

Figure 3A:
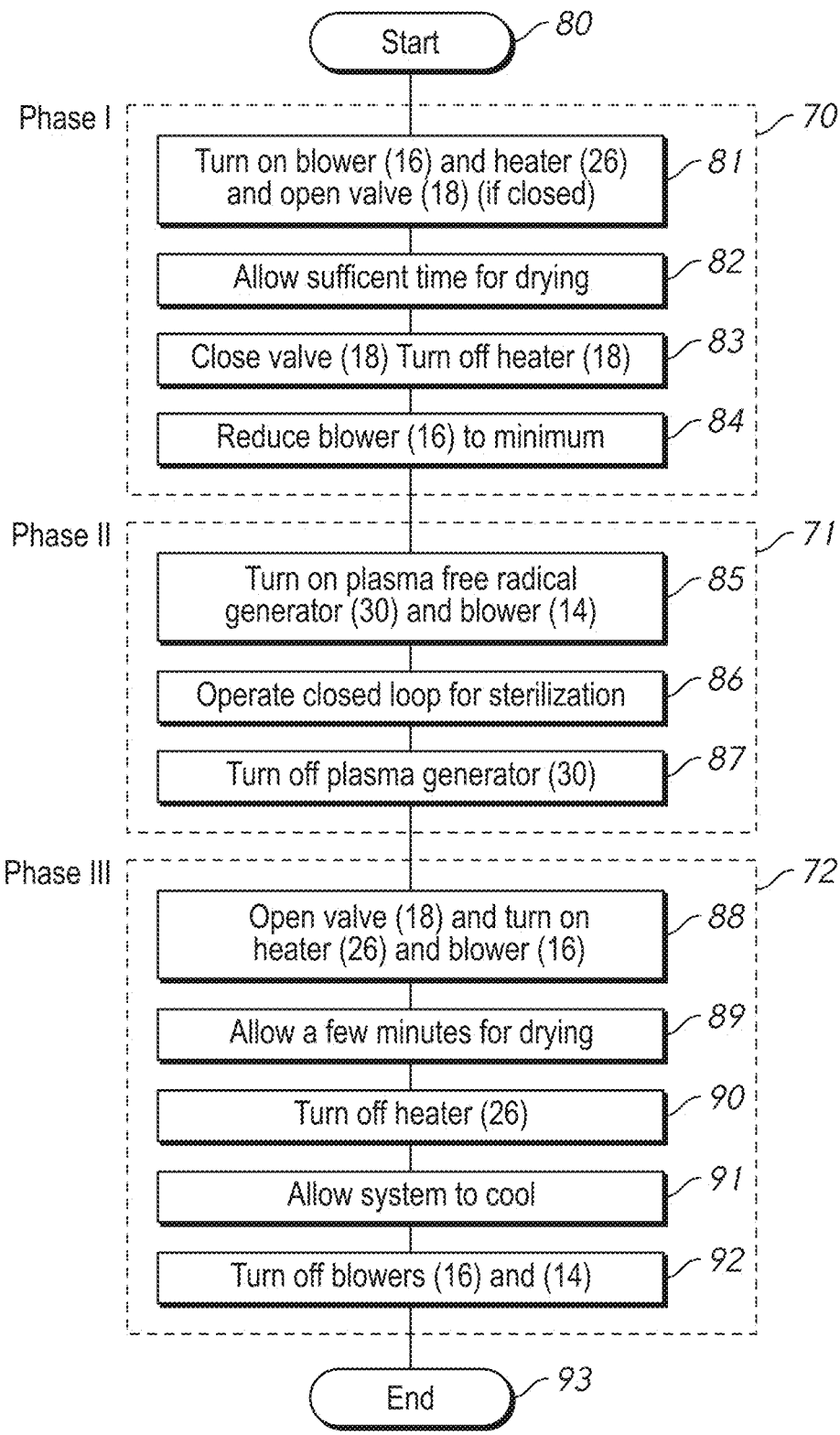
FIG. 3A shows a flowchart of an example method of the disclosure.

As shown in FIG. 3A, the sterilization process using the embodiments of the disclosure which have pre-heaters and/or exhaust systems, may include three phases:

80—Start the method

70—Phase I—Pre-sterilization drying and optionally heating (Open Loop)

81—During this phase the exhaust blower 16 is turned on, the valve 18 is opened (if closed) and the heater 26 is turned on. This causes fresh air from the inlet 58 to flow through valve 18, optional HEPA filter 20, and heater 26 into chamber 10 via conduit 42. The heated air dries and heats the sterilized items and is expelled through conduit 42 via optional filter 22, free radical destroyer 24 and exhaust blower 16.

82—The drying and heating is continued for a sufficient time, for example approximately 5 minutes. If desired, a heat sensor or humidity sensor (not shown) could be provided at the exhaust 56 or in conduit 44, coupled to the controller 12, so that the duration of the pre-heating could be controlled based on empirical data rather than an arbitrary elapsed time. Optionally, if a chamber temperature sensor 52 is provided, the controller 12 may operate heater 26 and, if provided, chamber heaters 64 and/or 66 to maintain a desired pre-heat temperature in the chamber.

83—After the chamber and the sterilized items are dried and heated the input valve 18 is closed.

84—The exhaust blower 16 is turned off (or reduced to minimum speed, if this ability is available)

71—Phase II—Sterilization (Closed Loop)

85—The plasma generator 30 and/or the vaporizer 32, and the closed loop blower/distributor 14 are turned on. This causes the air to circulate in the closed loop through the effluent generator 46 and the chamber 10, as described in the description of the apparatus, above.

86—The closed loop system produces continuously free radical rich effluent that sterilizes items in the chamber 10. The closed loop operation continues for a time sufficient for sterilization. As an example, a duration of approximately 20-30 minutes should be sufficient for adequate sterilization of most items. If provided, the controller 12 will activate chamber heaters 64 and/or 66 to maintain a desired temperature in chamber 10, as measured by sensor 52.

87—At the end of the sterilization period, the plasma generator 30 and/or vaporizer 32 is turned off.

72—Phase III—Post-sterilization drying and clearing (Open Loop)

88—Input valve 18 is opened, heater 26 is turned on and the exhaust blower 16 is turned on. The closed loop blower/distributor 14 may remain on during this Phase III in order to dry free radical source 46, or, if desired, blower/distributor may be turned off in step 87. The air flows from the input 58 via conduit 42 into the chamber 10 drying the items and, if blower 14 remains on, the free radical source 46. The moist air is expelled into the atmosphere via filter 22 and free radical destroyer 24.

89—The open loop operation is maintained for a time sufficient to dry and clear the chamber 10. The drying operation may be maintained for a sufficient period to warm and/or dry the items 56/62 in chamber 10, thereby limiting or preventing bacterial growth on the items. If desired, a closed loop drying operation may be utilized (e.g., in which a desiccant or other dryer and/or heater are provided in a closed loop path). A period of, for example, five minutes should suffice.

90—Heater 26 is turned off, with blower 16 (and blower 14, if desired) remaining on.

91—Fresh air is passed through the system for a sufficient time to cool down to the ambient temperature. For example, a few minutes operation would suffice for cooling. Optionally, if sensor 52 is provided in the chamber, the controller 12 could be programmed to continue this cooling until a desired temperature is reached.

92—Blower 16 is turned off, as well as blower 14 if it is still on. Valve 18 may be closed at this time, or left open for the next run.

93—The method ends. The chamber 10 may now be opened and the items 56/62 removed. New items may be put in the chamber, if desired, and the process repeated again from 80. Additional filters, blowers, sensors (e.g., temperature, pressure, humidity, etc.), and/or controls may be incorporated into various embodiments. Furthermore, various embodiments may incorporate a bar code reader, a print out, and/or other accessories and/or methods, e.g., to enhance quality control and/or regulatory compliance.

[Another Example Method of Operation—without Heating

The sterilization cycle has varied humidity; during the initial part of the cycle the sterilant has low humidity, for example about 50%. During this part of the cycle the excessive residual moisture on the sterilized items is removed. The later part of the cycle delivers the circulating sterilant to the items at much higher humidity, for example about 80% to 90%, that speeds up the sterilization process.

Additional Example Method of Operation—Residual Coating Device

Figure 3B:
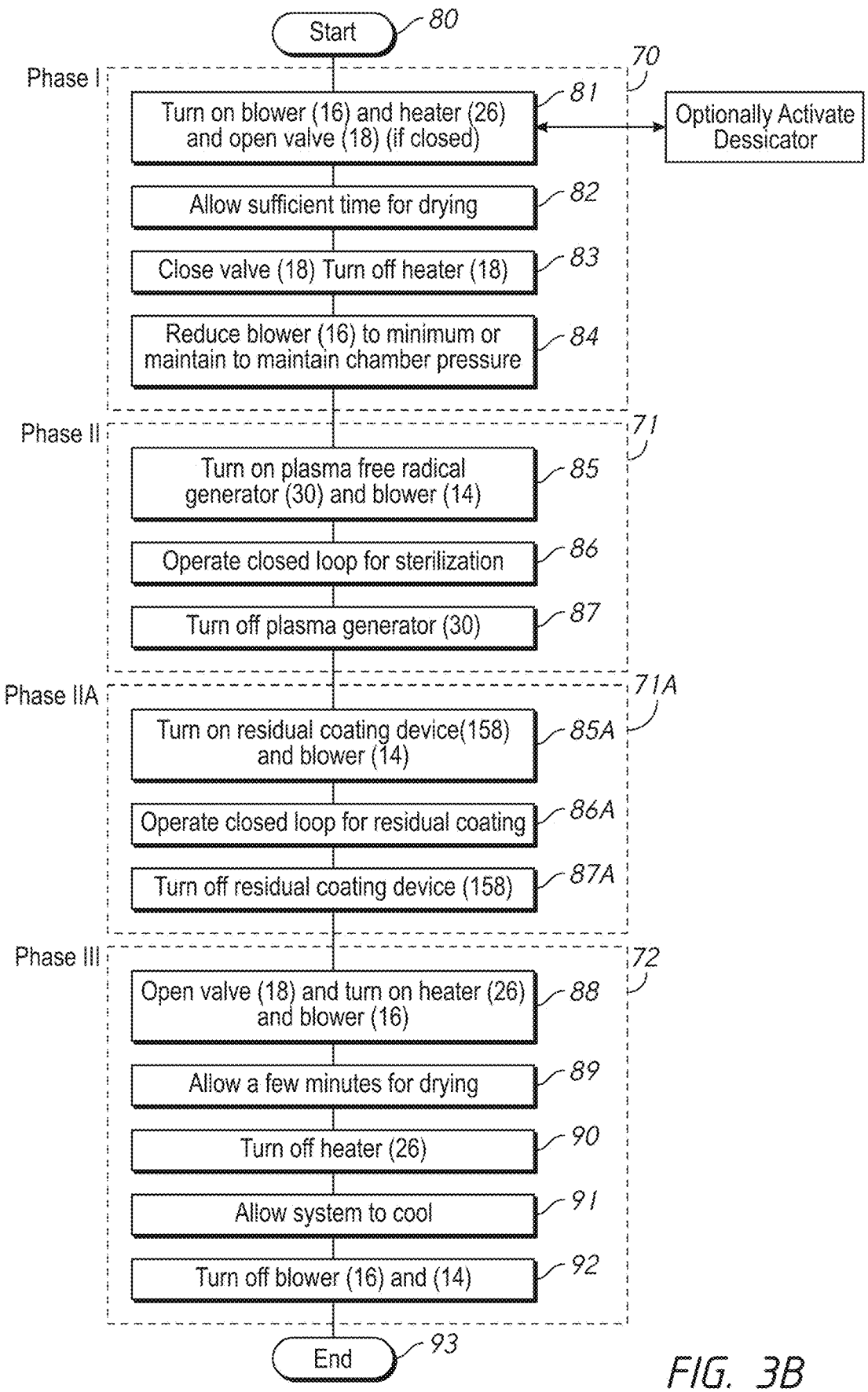
FIG. 3B shows a flowchart of an example method of the disclosure with an optional step of extended drying of items in the chamber and with an optional step of depositing a protective coating on items in the chamber.

As shown in FIG. 3B, processes using the embodiments of the disclosure, may include a residual coating phase:

71A—Phase IIA—Residual Coating

85A—The residual coating device 158 and the closed loop blower/distributor 14 are turned on and the residual coating valve 156 is opened. This causes gas to circulate, in a closed loop, through the residual coating device 158 and the chamber 10, as described in the description of the apparatus, above.

86A—The closed loop system produces continuously residual coating rich effluent that coats items in the chamber 10. The closed loop operation continues for a time sufficient for coating. As an example, a duration of approximately 1-5, 5-10, 10-15, 15-20, or 20-30 minutes should be sufficient for adequate coating of most items. If provided, the controller 12 will activate chamber heaters 64 and/or 66 to maintain a desired temperature in chamber 10, as measured by sensor 52.

87A—At the end of the residual coating period, the residual coating device 158 is turned off.

The residual coating process may be performed in addition to or instead of the sterilization phase and other phases described herein. For example, in arrangements in which previously-sterilized items are available, the residual coating process may be performed without a sterilization phase to deposit the additional residual coating on those items.

Additional Example Method of Operation—Device for Relative Humidity Cycling

Figure 3C:
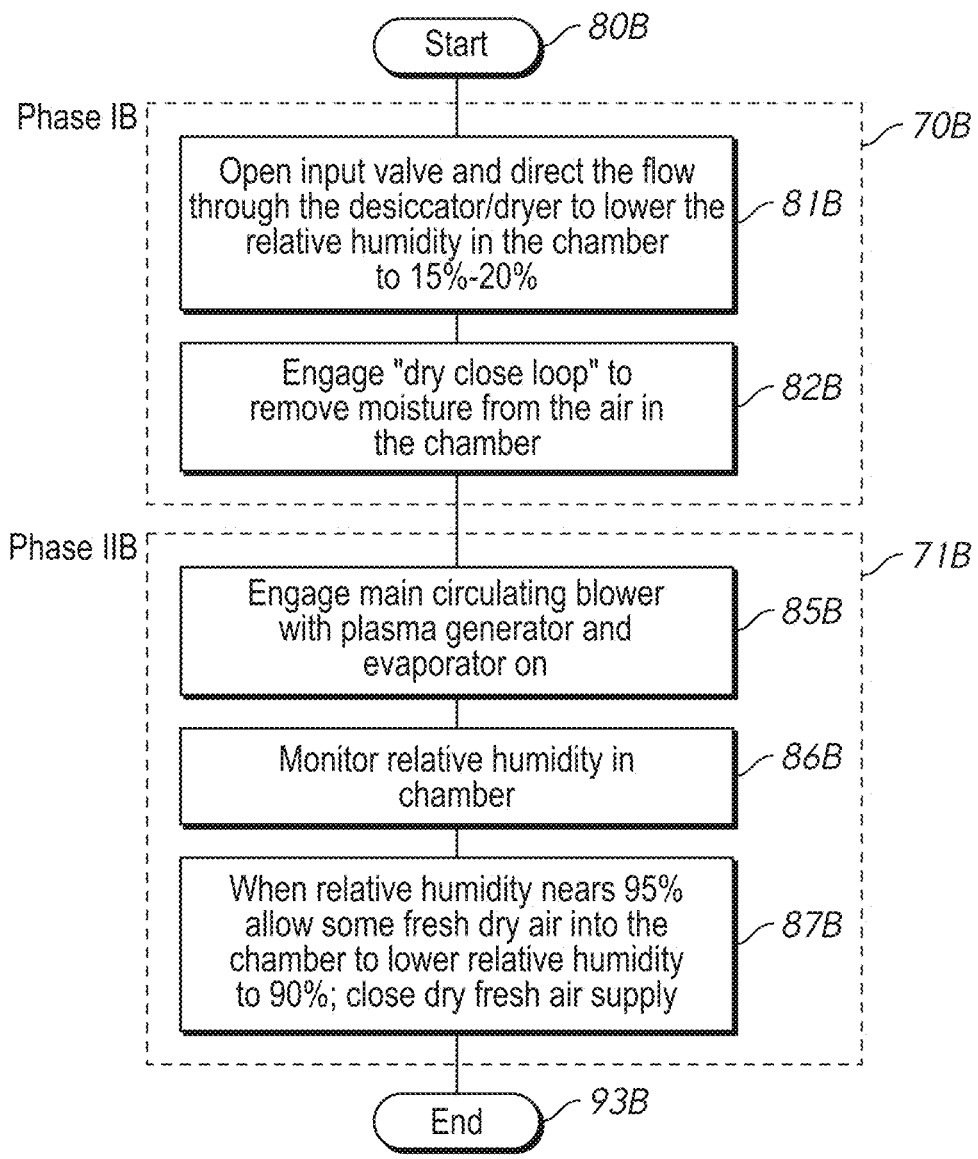
FIG. 3C shows a flowchart of another example method of the disclosure.

As shown in FIG. 3C, processes using the embodiments of the disclosure, may be used to obtain a desired relative humidity:

80B—Start the method

70B—Phase IB—Obtaining the desired initial low relative humidity

81B—Open the input valve and direct the flow through the desiccator/dryer to lower the relative humidity in the chamber to 15%-20% level.

82B—Engage the "dry close loop" to remove moisture from the air in the chamber. In some embodiments, this can be a separate closed loop that circulates the air between the chamber and the desiccator/dryer.

71B—Phase IIB—Proper Sterilization Cycle
   85B—Engage a main circulating blower with plasma generator and evaporator on
   86B—Monitor relative humidity in the chamber
   87B—When the relative humidity nears 95%, allow some fresh dry air (through the desiccator/dryer) into the chamber to lower the relative humidity to 90%. Subsequently close the dry fresh air supply.

Figure 3D:
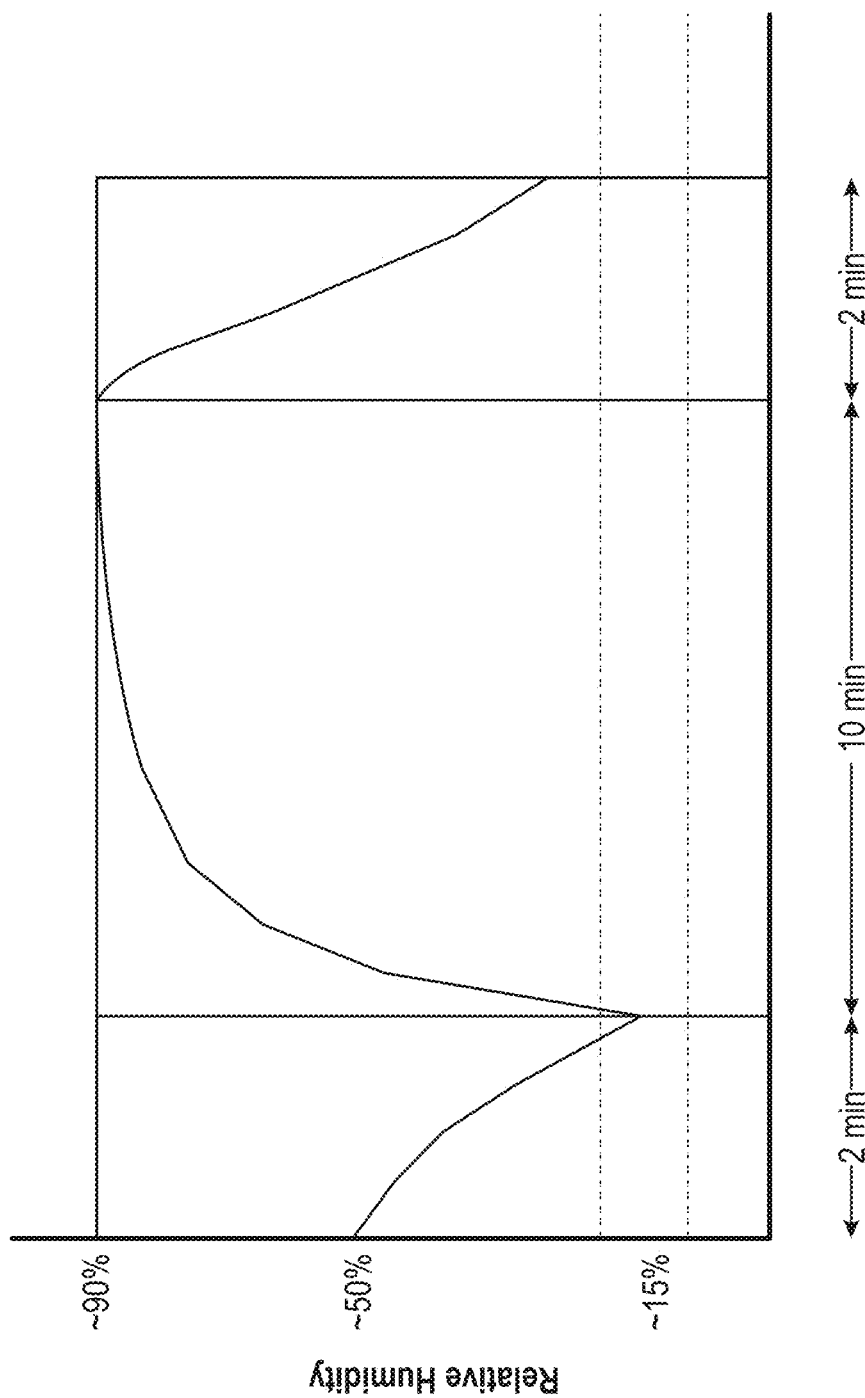
FIG. 3D shows a chart illustrated the proposed relative humidity levels in the chamber during one embodiments of the disclosed sterilization/disinfection cycle.

FIG. 3D illustrates an example of the proposed relative humidity levels in the chamber during the sterilization/disinfection cycle. Please note that the 2 minute and 10 minute marks are arbitrary.

Incorporation into an Appliance Having a Closed Space

Certain appliances may harbor various sorts of fungi or pathogens (e.g., microbes). Growth of such fungi and pathogens may be from moisture or other enabling process conditions. Accordingly, various embodiments described herein can be incorporated into an appliance having a closed space. For example, in washing machines, especially front loading washing machines, there is a potential for undesirable growth of mold, fungus, mildew, slime, or some combination thereof (collectively and/or individually referred to herein as "mold" for brevity purposes). Most front loading washing machines require a water-tight seal when the door is shut, in order to prevent water leakage during the wash cycle. Many front loading washing machines also include a gasket assembly between the door and the wash drum, primarily to keep clothing within the drum. Due to these features, front loading washing machines often are not completely drained of detergent, wash water, and/or rinse water after a wash cycle. Some liquid remains pooled in various areas of the washer, often in and around the gasket and the drum, door, and gasket interfaces. This pooled liquid has a high probability of becoming polluted and contaminated over time, resulting in the growth of mold and odors, which are unpleasant, unsightly, and unsanitary. Various mold-preventative remedies have been suggested or implemented such as drying the gasket assemblies after use, running a hot water cleaning cycle with bleach, leaving the washer door open to dry out the interior, and running a dehumidifier in the space the washer is being used. However, such remedies have not fully addressed the problem and mold remains and continues to present a problem in front loading washing machines.

As illustrated in FIG. 16, some embodiments as described herein may be incorporated into a washing machine. Although various aspects are described in the washing machine, it would be appreciated that such features can apply to other appliances with a closed space, such as dishwashers, dryers, or refrigerators (e.g., in the fruit and vegetable containment compartments). When incorporated into a front loading washing machine, the sterilization system (or disinfection, sanitization, or decontamination system) can substantially reduce or eliminate the mold problem typically found in front loading washing machines or other system with a closed space. In such arrangements, the sterilization chamber 10 of the systems described herein becomes the washing machine chamber 154, including the washing drum, gasket assembly, interior of the front door, other components exposed to the wash environment, as well as potentially other components in the washing machine such as the detergent loading equipment (which may be a tray or other device).

In operation, the gaseous sterilant produced by evaporator 32 and plasma generator 30, individually or in combination, is circulated by blower 14 through the washing machine chamber 154. Due to the gaseous nature of the sterilant, the sterilant is easily spread to substantially all of the exposed surfaces of the washing machine chamber 154 and substantially all surfaces that can harbor mold or other pathogens in crevices, including difficult to reach spaces through diffusion of the gaseous sterilant. In this manner, the problem of mold in front loading washing machines and other systems with closed spaces can be reduced or even eliminated. Moreover, since front loading washing machines are generally water-tight, the recirculating sterilant can be substantially contained within the chamber, especially when operating at a slightly negative pressure.

When incorporated into a washing machine, the evaporator 32 (and associated components) and plasma generator 30 may both be included or, if desired, one of the evaporator 32 and the plasma generator 30 may be omitted. For example, similar to FIG. 5, FIG. 17 illustrates an example embodiment in which the sterilant is generated by an evaporator 32 and without a plasma generator 30. The sterilant may include hydrogen peroxide vapor. The vapor can interact with surfaces within the chamber 154 killing pathogens it encounters. Even if a surface in the chamber is wet, some of the sterilant vapor may penetrate the surface to kill the pathogens because it is in equilibrium with the liquid solution in the evaporator 32 and thus the vapor may attempt to be in similar equilibrium with the surface.

Similar to FIG. 4, some embodiments may utilize sterilant generated by a plasma generator 30 and without an evaporator 32. The sterilant may include active species produced in the plasma generator 30, such as excited oxygen species (e.g., $O_2$, $O_3$, and/or O) and nitrogen oxide ($N_2O$ or $NO_2$).

The preferred embodiment may depend on factors such as the time devoted for sanitization and/or the recommended cycle to be utilized. For example, in some embodiments, using both a plasma generator 30 and an evaporator 32 may produce the more potent sterilant than using the plasma generator 30 or evaporator 32 alone. As another example, using less sterilizing agent solution (e.g., hydrogen peroxide) in the evaporator 32 may in some cases result in longer operation times.

In various embodiments, the moisture control features described in connection with FIGS. 1E-1G may be included or omitted, as desired. Omitting the dryer of FIGS. 1F-1G might reduce the cost of the system; while incorporating the dryer might help in enabling a drying component of the sterilization cycle (e.g., drying can further reduce the risks of mold developing). FIG. 18 illustrates the input 154a and output 154b of the chamber 154 in some embodiments. It may be desirable to arrange the sterilant recirculation lines, particularly the lines of the input 154a and output connected to chamber 154, such that water is not stored in the lines as a result of the washing cycle (such water could tend to decrease the efficacy of the sanitization system). It may also be desirable to activate the tumbling of the washing drum during sanitization to create turbulence with the chamber.

A sterilization cycle may be performed whenever the door is closed, as determined by door sensor 150. If desired, the washing machine may also include a sensor such as a pressure sensor, which determines if the washing drum is empty or full of clothing or other materials. In such an arrangement, the washing machine may prevent activation of the sterilization cycle unless empty. The sterilization cycle may be user initiated or may be automatically initiated based on programmed criteria (e.g., once a day, once a week, once a month, at the end of a wash cycle, after a certain number of wash cycles, if a time between wash cycles exceeds a threshold, some combination of these and other criteria, etc.).

A sterilization cycle may, as an example, include some or all of the following steps (in any order). First, controller 12 may open hydrogen peroxide valve 142 and activate evaporator 32 (unless evaporator 32 and its associated components are omitted). Then, controller 12 may activate exhaust blower 16 to establish a negative pressure within washing machine chamber 154 and may activate circulating blower 14. (Controller 12 may continuously adjust exhaust blower 16 based on readings from sensors 52 to maintain the desired negative pressure.) A few seconds (e.g., 5 seconds) after turning on the circulating blower 14, controller 12 may activate plasma generator 30 (unless plasma generator 30 is omitted). Controller 12 may then wait for the primary duration of the cycle (the duration may be adjustable by controller 12 or by a user). As the end of the cycle nears, controller 12 may turn off the plasma generator 30, if present. A few seconds (e.g., 3 seconds) after the plasma generator 30 is turned off, controller 12 may turn up the exhaust blower 16 (perhaps to full power) and open input purging valve 18 in order to purge the sterilant from the washing chamber 154. The controller 12 may continue purging the chamber for any desired length of time (e.g., 5 seconds, 10 seconds, 20 seconds, etc.).

If desired, the controller 12 may monitor the door sensor 150 and, if the door is opened at any point in the cycle, close the hydrogen peroxide valve 142, deactivate plasma generator 30, and activate the exhaust blower 16 at full power for a desired amount of time (e.g., 5 seconds, 10 seconds, 20 seconds, etc.). Controller 12 may also, in such situations, close the intake purging valve 18. By closing purging valve 18, the exhaust blower will draw the circulating sterilant away from the opened door, further reducing any potential safety risks associated with the sterilant escaping through the opened door.

Implementation Mechanisms

According to some embodiments, the methods described herein can be implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, server computer systems, portable computer systems, handheld devices, networking devices or any other device or combination of devices that incorporate hard-wired and/or program logic to implement the techniques.

Computing device(s) are generally controlled and coordinated by operating system software, such as iOS, Android, Chrome OS, Windows XP, Windows Vista, Windows 7, Windows 8, Windows Server, Windows CE, Unix, Linux, SunOS, Solaris, iOS, Blackberry OS, VxWorks, or other compatible operating systems. In other embodiments, the computing device may be controlled by a proprietary operating system. Conventional operating systems control and schedule computer processes for execution, perform memory management, provide file system, networking, I/O services, and provide a user interface functionality, such as a graphical user interface ("GUI"), among other things.

In some embodiments, the computer system includes a bus or other communication mechanism for communicating information, and a hardware processor, or multiple processors, coupled with the bus for processing information. Hardware processor(s) may be, for example, one or more general purpose microprocessors.

In some embodiments, the computer system may also include a main memory, such as a random access memory (RAM), cache and/or other dynamic storage devices, coupled to a bus for storing information and instructions to be executed by a processor. Main memory also may be used for storing temporary variables or other intermediate information during execution of instructions to be executed by the processor. Such instructions, when stored in storage media accessible to the processor, render the computer system into a special-purpose machine that is customized to perform the operations specified in the instructions.

In some embodiments, the computer system further includes a read only memory (ROM) or other static storage device coupled to bus for storing static information and instructions for the processor. A storage device, such as a magnetic disk, optical disk, or USB thumb drive (Flash drive), etc., may be provided and coupled to the bus for storing information and instructions.

In some embodiments, the computer system may be coupled via a bus to a display, such as a cathode ray tube (CRT) or LCD display (or touch screen), for displaying information to a computer user. An input device, including alphanumeric and other keys, is coupled to the bus for communicating information and command selections to the processor. Another type of user input device is cursor control, such as a mouse, a trackball, or cursor direction keys for communicating direction information and command selections to the processor and for controlling cursor movement on display. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

In some embodiments, the computing system may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "module," as used herein, refers to logic embodied in hardware or firmware, or to a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software modules configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware modules may be comprised of connected logic units, such as gates and flip-flops, and/or may be comprised of programmable units, such as programmable gate arrays or processors. The modules or computing device functionality described herein are preferably implemented as software modules, but may be represented in hardware or firmware. Generally, the modules described herein refer to logical modules that may be combined with other modules or divided into sub-modules despite their physical organization or storage In some embodiments, a computer system may implement the methods described herein using customized hard-wired logic, one or more ASICs or FPGAs, firmware and/or program logic which in combination with the computer system causes or programs the computer system to be a special-purpose machine. According to one embodiment, the methods herein are performed by the computer system in response to hardware processor(s) executing one or more sequences of one or more instructions contained in main memory. Such instructions may be read into main memory from another storage medium, such as a storage device. Execution of the sequences of instructions contained in main memory causes processor(s) to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, or other types of storage devices. Volatile media includes dynamic memory, such as a main memory. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between nontransitory media. For example, transmission media includes coaxial cables, copper wire and fiber optics, including the wires that comprise a bus. Transmission media can also take the form of acoustic or light waves, such as those generated during radio-wave and infra-red data communications.

Various forms of media may be involved in carrying one or more sequences of one or more instructions to a processor for execution. For example, the instructions may initially be carried on a magnetic disk or solid state drive of a remote computer. The remote computer can load the instructions into its dynamic memory and send the instructions over a telephone line using a modem or other network interface, such as a WAN or LAN interface. A modem local to a computer system can receive the data on the telephone line and use an infra-red transmitter to convert the data to an infra-red signal. An infra-red detector can receive the data carried in the infra-red signal and appropriate circuitry can place the data on a bus. The bus carries the data to the main memory, from which the processor retrieves and executes the instructions. The instructions received by the main memory may retrieve and execute the instructions. The instructions received by the main memory may optionally be stored on a storage device either before or after execution by the processor.

In some embodiments, the computer system may also include a communication interface coupled to a bus. The communication interface may provide a two-way data communication coupling to a network link that is connected to a local network. For example, a communication interface may be an integrated services digital network (ISDN) card, cable modem, satellite modem, or a modem to provide a data communication connection to a corresponding type of telephone line. As another example, a communication interface may be a local area network (LAN) card to provide a data communication connection to a compatible LAN (or WAN component to communicate with a WAN). Wireless links may also be implemented. In any such implementation, a communication interface sends and receives electrical, electromagnetic or optical signals that carry digital data streams representing various types of information.

A network link may typically provide data communication through one or more networks to other data devices. For example, a network link may provide a connection through a local network to a host computer or to data equipment operated by an Internet Service Provider (ISP). The ISP in turn provides data communication services through the world wide packet data communication network now commonly referred to as the "Internet." The local network and Internet both use electrical, electromagnetic or optical signals that carry digital data streams. The signals through the various networks and the signals on the network link and through a communication interface, which carry the digital data to and from the computer system, are example forms of transmission media.

In some embodiments, the computer system can send messages and receive data, including program code, through the network(s), the network link, and the communication interface. In the Internet example, a server might transmit a requested code for an application program through the Internet, ISP, local network, and communication interface.

The received code may be executed by a processor as it is received, and/or stored in a storage device, or other non-volatile storage for later execution.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention. The drawings are for the purpose of illustrating embodiments of the invention only, and not for the purpose of limiting it.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "deploying an instrument sterilized using the systems herein" include "instructing the deployment of an instrument sterilized using the systems herein." In addition, where features or aspects of the disclosure are described in terms of Markush groups, those skilled in the art will recognize that the disclosure is also thereby described in terms of any individual member or subgroup of members of the Markush group.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers."

What is claimed is:

1. A system for treating at least one item, comprising:
a first unit comprising a disinfectant generator, wherein the disinfectant generator comprises:
  a free radical generator wherein the free radical generator generates ozone;
  a vaporizer unit in fluidic communication with a reservoir of disinfectant media, wherein the vaporizer unit is configured to generate a vapor of said disinfectant media;
  a gas distribution unit, wherein the unit conducts a gas from at least one outlet of the gas distribution unit to an inlet of the free radical generator and to the reservoir of disinfectant media or the vaporizer unit, wherein the disinfectant generator is configured to generate an effluent capable of disinfection or sanitization of the at least one item; and
  a first chamber configured to mix the ozone and the disinfectant media;
a second unit comprising:
  a second chamber for containing an item or items to be treated, wherein the second chamber is configured to form a sealed and enclosed area which can receive the at least one item, and wherein the second chamber comprises a single inlet for receiving effluent from the disinfectant generator; and
  at least one conduit in fluidic communication with the first unit and the second unit, wherein the conduit is configured to convey the disinfecting effluent from the first unit to the second unit; and wherein the system operates at a humidity within an interior of the second chamber of between about 20% and 90% relative humidity;
wherein the system is configured to operate at a temperature between 60 to about 80 degrees Fahrenheit during disinfection or sanitization of the item or items to be treated;
wherein the first chamber is stationary within the system;
wherein the ozone and the disinfectant media are configured to mix in the first chamber before entering the second chamber; and
wherein the system for treating at least one item does not include a heating unit for disinfection or sanitization of the item or items.

2. The system of claim 1 wherein the system is configured for sanitization of the at least one item.

3. The system of claim 1, wherein the system is configured for treatment of a plurality of items, each of the plurality of items having an internal lumen.

4. The system of claim 1, wherein the system further comprises an insert configured to be placed within the sealed and enclosed area, the insert configured to contain the at least one item to be treated.

5. The system of claim 1, wherein said disinfectant media comprises a liquid and the vaporizer comprises an evaporator and a wicking material that is configured to absorb mist.

6. The system of claim 1, wherein the chamber further comprises an additional conduit that fluidically connects an interior of the chamber with an exterior environment and the additional conduit comprises one or more of a filter, a free radical destroyer and a blower.

7. The system of claim 1, wherein the second unit is configured to store the at least one item until a subsequent use of the at least one item.

8. The system of claim 1, wherein the second unit is rigid.

9. The system of claim 1, wherein the free radical generator is a cold plasma generator.

10. The system of claim 1, wherein the reservoir of disinfectant media comprises a liquid or solid source of hydrogen peroxide.

11. The system of claim 10, wherein the reservoir of disinfectant media is removable.

12. The system of claim 1, wherein the system operates at a pressure not significantly different from an ambient environmental pressure.

13. The system of claim 1, wherein the system is configured to operate at a pressure between 600 mm Hg and 800 mm Hg and at a temperature ranging from 15 degrees Celsius to 50 degrees Celsius.

14. The system of claim 1, wherein the maintained relative humidity enables the system to achieve disinfection of electronic devices.

15. The system of claim 1, wherein the system further comprises at least one desiccant depot configured to assist in maintaining the humidity.

16. The system of claim 1, wherein the disinfectant generator generates an effluent capable of disinfection and said disinfection is achieved in a cycle time of between 120 seconds to 10 minutes.

17. The system of claim 1, wherein the system further comprises a HEPA configured to flush the second unit.

18. The system of claim 1, wherein the system further comprises an activated carbon filter configured to ensure only clean air leaves the system.

19. A method for disinfecting at least one item at ambient temperatures, comprising:
receiving the at least one item in a chamber that forms a sealed and enclosed area around the at least one item;
receiving input from a graphical user interface to run one of the pre-programmed cycles;
receiving a cartridge configured to engage with a cartridge valve, wherein the cartridge is in fluid communication with a vaporizer unit;

activating a disinfectant generator, wherein the disinfectant generator comprises:
a free radical generator, and
the cartridge comprising a reservoir of disinfectant media in fluid communication with a vaporizer unit;
circulating disinfectant media within the chamber for a period of between 120 seconds to 10 minutes, wherein activation of the disinfectant generator causes disinfecting effluent to enter the chamber and disinfect the at least one item;
maintaining the interior of the chamber at a temperature ranging between 60 degrees Fahrenheit to 80 degrees Fahrenheit during disinfection of the at least one item;
storing the at least one item in the chamber; and
wherein the disinfectant generator is configured to generate a disinfecting effluent capable of destruction of vegetative microorganisms, mycobacterium, small or nonlipid viruses, medium or lipid viruses, fungal spores, and bacterial spores on the at least one item, and
wherein the disinfectant generator does not comprise a heating unit.

20. The method of claim 19, wherein an interior of the chamber is maintained at a humidity of between about 20% and 60% relative humidity.

21. The method of claim 19, wherein the disinfectant effluent is hydrogen peroxide, wherein the hydrogen peroxide is introduced into the chamber through the vaporizer unit, and further comprising continuously supplying ozone into the chamber through a closed loop flow after the disinfecting effluent enters the chamber, wherein the ozone is configured to neutralize the disinfecting effluent.

22. The method of claim 19, further comprising introducing air into the system through a filter to flush the chamber after the at least one item has been disinfected, wherein the filter is a HEPA filter.

23. The method of claim 22, further comprising exhausting the air in the chamber through a filter system to ensure no disinfectant leaves the chamber, wherein the filter system comprises a HEPA filter and an activated carbon filter.

24. The method of claim 19, wherein the disinfectant generator does not comprise a dehumidifier.

25. A method for disinfecting at least one item at ambient temperatures, comprising:
placing the at least one item in a chamber that forms a sealed and enclosed area around the at least one item;
activating a graphical user interface;
selecting a disinfection cycle, wherein the disinfection cycle is configured to:
activate a disinfectant generator, wherein the disinfectant generator comprises:
a free radical generator, and
a reservoir of disinfectant media in fluid communication with a vaporizer unit,
wherein the disinfectant generator is configured to generate a disinfecting effluent capable of destruction of vegetative microorganisms, mycobacterium, small or nonlipid viruses, medium or lipid viruses, fungal spores, and bacterial spores on the at least one item, and
wherein the disinfectant generator does not comprise a heating unit;
circulate disinfectant media within the chamber for a period of between 120 seconds to 10 minutes, wherein activation of the disinfectant generator causes disinfecting effluent to enter the chamber and disinfect the at least one item; and
maintain the interior of the chamber at a temperature ranging between 60 degrees Fahrenheit to 80 degrees Fahrenheit during disinfection of the at least one item; and
removing the at least one item from the chamber.

* * * * *